United States Patent
Sugimoto et al.

(10) Patent No.: US 10,538,528 B2
(45) Date of Patent: Jan. 21, 2020

(54) 5H-PYRROLO[2,3-D]PYRIMIDIN-6(7H)-ONE DERIVATIVE

(71) Applicant: Taiho Pharmaceutical Co., Ltd., Chiyoda-ku, Tokyo (JP)

(72) Inventors: Tetsuya Sugimoto, Ibaraki (JP); Toshihiro Sakamoto, Ibaraki (JP); Fuyuki Yamamoto, Ibaraki (JP); Yu Kobayakawa, Ibaraki (JP); Naoki Egashira, Ibaraki (JP); Koji Ichikawa, Ibaraki (JP); Takumitsu Machida, Ibaraki (JP)

(73) Assignee: Taiho Pahrmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/302,829

(22) PCT Filed: May 19, 2017

(86) PCT No.: PCT/JP2017/018825
§ 371 (c)(1),
(2) Date: Nov. 19, 2018

(87) PCT Pub. No.: WO2017/200087
PCT Pub. Date: Nov. 23, 2017

(65) Prior Publication Data
US 2019/0292190 A1    Sep. 26, 2019

(30) Foreign Application Priority Data

May 20, 2016 (JP) ................................. 2016-101599

(51) Int. Cl.
*C07D 487/04* (2006.01)
*A61P 35/00* (2006.01)
*A61K 31/519* (2006.01)

(52) U.S. Cl.
CPC .......... *C07D 487/04* (2013.01); *A61K 31/519* (2013.01); *A61P 35/00* (2018.01)

(58) Field of Classification Search
CPC ............................ C07D 487/04; A61K 31/519
See application file for complete search history.

(56) References Cited

FOREIGN PATENT DOCUMENTS

| JP | 2007-534687 A | 11/2007 |
| JP | 2012-508274 A | 4/2012 |
| WO | WO 2005/117909 A2 | 12/2005 |
| WO | WO 2010/056563 A1 | 5/2010 |

OTHER PUBLICATIONS

International Search Report dated Aug. 1, 2017, in PCT/JP2017/018825.

Aronchik et al., "Novel Potent and Selective Inhibitors of p90 Ribosomal S6 Kinase Reveal the Heterogeneity of RSK Function in MAPK-Driven Cancers," Molecular Cancer Research, 2014, 12(5)1303-812.

Caroten et al., "A transforming mutation in the pleckstrin homology domain of AKT1 in cancer," Nature, Jul. 26, 2007, 448(7152):439-444.

Fenton et al., "Functions and regulation of the 70 kDa ribosomal S6 kinases," The International Journal of Biochemistry and Cell Biology, 2011, 43(1):47-59.

(Continued)

*Primary Examiner* — Susanna Moore
(74) *Attorney, Agent, or Firm* — Foley & Lardner LLP

(57) ABSTRACT

The invention of the present application provides a compound represented by Formula (I) or a salt thereof, which exhibits an inhibitory activity against at least one kinase selected from the group consisting of Akt kinase, Rsk kinase, and S6K kinase and/or a cell proliferation inhibiting effect and is useful as a prophylactic and/or therapeutic agent for diseases associated with the above-mentioned kinases, particularly cancer. [In the formula, $R_1$ represents a 4- to 6-membered monocyclic unsaturated heterocyclic group which has 1 to 3 hetero atoms independently selected from N, S and O and may have a substituent; $R_2$ represents a hydrogen atom or the like; $R_3$, $R_4$, and $R_5$, may be the same as or different from one another and independently represent a hydrogen atom or the like; $R_6$ represents a hydrogen atom or the like; $R_7$ and $R_8$, may be the same as or different from each other and independently represent a hydrogen atom or the like; $X_1$ and $X_2$ may be the same as or different from each other and independently represent N or $CR_9$; $R_9$ represents a hydrogen atom or the like; and $X_3$ represents N or CH when the broken line ( ---- ) represents a single bond, and represents C when a broken line indicates a double bond, wherein at least one of $X_1$ or $X_2$ represents N.]

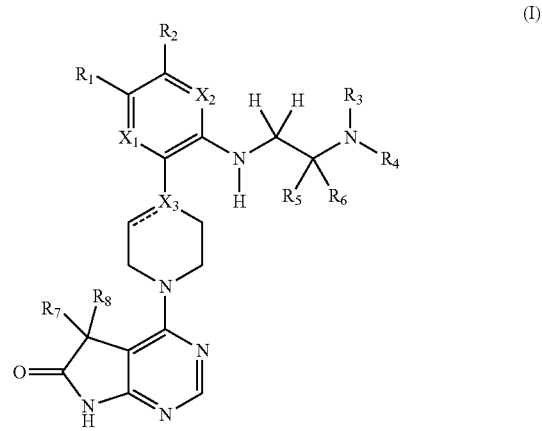

(I)

10 Claims, No Drawings

(56) References Cited

OTHER PUBLICATIONS

Ludwik et al., "Development of a RSK Inhibitor as a Novel Therapy for Triple-Negative Breast Cancer," Molecular Cancer Therapeutics, 2016, 15(11):2598-2608.
Luo et al., "Potent and selective inhibitors of Akt kinases slow the progress of tumors in vivo," Mol. Canc. Ther., Jun. 2005, 4(6):977-986.
Fayard et al., "Protein kinase B/Akt at a glance," Journal of Cell Science, 2005, 118(Pt.24):5675-5678.
Hirai et al., "MK-2206, an Allosteric Akt Inhibitor, Enhances Antitumor Efficacy by Standard Chemotherapeutic Agents or Molecular Targeted Drugs In vitro and In vivo," Molecular Cancer Therapeutics, 2010, 9(7):1956-1967.
Rhodes et al., "Characterization of an Akt Kinase Inhibitor with Potent Pharmacodynamic and Antitumor Activity," Cancer Res., Apr. 1, 2008, 68(7):2366-2374.
Romeo et al., "Regulation and function of the RSK family of protein kinases," Biochem. J., 2012, 441(2):553-569.
Tokunaga et al., "Deregulation of the Akt Pathway in Human Cancer," Current Cancer Drug Targets, 2008, 8(1):27-36.
Tolcher et al., "A phase I trial of LY2584702 tosylate, a p70 S6 kinase inhibitor, in patients with advanced solid tumours," European Journal of Cancer, 2014, 50(5):867-875.

US 10,538,528 B2

5H-PYRROLO[2,3-D]PYRIMIDIN-6(7H)-ONE DERIVATIVE

CROSS-REFERENCE TO RELATED APPLICATIONS

This application is a National Stage application of PCT/JP2017/018825, filed May 19, 2017, which claims priority from Japanese application JP 2016-101599, filed May 20, 2016.

TECHNICAL FIELD

The present invention relates to a novel 5H-pyrrolo[2,3-d]pyrimidin-6(7H)-one derivative, an inhibitor against at least one kinase selected from the group consisting of Akt kinase, Rsk kinase, and S6K kinase, a pharmaceutical composition for the treatment of a disease associated with at least one kinase selected from the group consisting of Akt kinase, Rsk kinase, and S6K kinase, and an anti-tumor agent.

BACKGROUND ART

Akt kinase (hereafter, referred to as "Akt") is serine/threonine kinase, which is also referred to as "PKB," and it is a molecule playing a key role in survival, growth, metabolism, and other functions of a cell (Non Patent Literature 1).

In various types of cancers, abnormal activation of Akt or mutation of the Akt gene has been observed, and involvement of Akt in onset, maintenance, and development of cancer phenotype has been strongly implied (Non Patent Literatures 2 and 3).

To date, several Akt-targeting inhibitors have been developed and their antitumor effects have been reported. Such inhibitors, however, do not exert sufficient antitumor effects in the form of single agents on non-clinical models, and strong cytotoxic effects at low concentration or strong antitumor effects in vivo have not yet been achieved (Non Patent Literatures 4 and 5). In addition, no clinical effects have been confirmed concerning such inhibitors.

In the reports that have been made in the past, in addition, cancer types on which the Akt inhibitor exerts certain effects are limited to cells or models of, for example, breast cancer, prostate cancer, and glioma (Non Patent Literatures 4 and 6), and examples exerting strong effects on other cancer species, such as colon cancer, are not known.

Among serine/threonine kinases that phosphorylate the 40S ribosomal protein S6, a kinase with a molecular weight of 90 kDa is referred to as Rsk kinase or p90 Rsk kinase (hereafter, referred to as "Rsk"). Rsk has been reported that it is located downstream of the Ras-Raf-MAPK signaling cascade, it is an important signal transducing molecule having functions of regulating growth, survival, metabolism, and motility of a cell, and it has various functions necessary for cancer cell proliferation (Non Patent Literature 7).

To date, several compounds exerting inhibitory activity against Rsk have been reported (Non Patent Literatures 7, 8, and 9), although the antitumor effects are limited. While it has been reported in non-clinical studies that an Rsk inhibitor has exerted certain effects on lung cancer, breast cancer, thyroid cancer, prostate cancer, and other cancer species in the past, there is no Rsk inhibitor that has been developed in clinical trials.

S6K kinase (hereafter, referred to as "S6K") is serine/threonine kinase that is indispensable for regulation of phosphorylation of the 40S ribosomal protein S6, as well as Rsk. It is considered that S6K is activated through the PI3K/mTOR signaling pathway upon stimulation of a growth factor, such as an insulin-like growth factor, and S6K regulates cancer through phosphorylation of various functional molecules necessary for various cancer properties (e.g., growth, survival, invasion, and metastasis) (Non Patent Literature 10). Also, ubiquitous high-level expression of S6K in tumors has been reported, and S6K inhibition has been expected to exert antitumor effects.

In recent years, a compound having S6K-selective inhibitory activity was reported. In clinical studies, however, a response has not been achieved at MTD (Non Patent Literature 11).

As piperazine derivatives having inhibitory activities against Akt, Rsk, and S6K, the compounds described in Patent Literatures 1 and 2 have been reported, but antitumor effects thereof are insufficient.

In the field of cancer treatment, accordingly, development of a serine/threonine kinase inhibitor that exhibits strong antitumor effect with a single agent and is effective against various cancers has still been awaited.

CITATION LIST

Patent Literature

Patent Literature 1: WO 2005/117909
Patent Literature 2: WO 2010/056563

Non Patent Literature

Non Patent Literature 1: J. Cell Sci., 2005; 118 (Pt 24): 5675-8
Non Patent Literature 2: Curr. Cancer Drug Targets, 2008; 8 (1): 27-36
Non Patent Literature 3: Nature, 2007; 448 (7152): 439-44
Non Patent Literature 4: Mol. Cancer Ther., 2005; 4 (6): 977-86
Non Patent Literature 5: Mol. Cancer Ther., 2010; 9 (7): 1956-67
Non Patent Literature 6: Cancer Res., 2008; 68 (7): 2366-74
Non Patent Literature 7: Biochem. J., 2012; 441 (2): 553-69
Non Patent Literature 8: Mol. Cancer Res., 2014; 12 (5): 803-12
Non Patent Literature 9: Mol. Cancer Ther., 2016; 15 (11): 2598-2608
Non Patent Literature 10: Int. J. Biochem. Cell Biol., 2011; 43 (1): 47-59
Non Patent Literature 11: Eur. J. Cancer., 2014; 50 (5): 867-75

SUMMARY OF INVENTION

Technical Problem

It is an object of the present invention to provide a novel 5H-pyrrolo[2,3-d]pyrimidin-6(7H)-one derivative, an inhibitor against at least one kinase selected from the group consisting of Akt, Rsk, and S6K, and a pharmaceutical composition or an anti-tumor agent for the treatment of a disease associated with at least one kinase selected from the group consisting of Akt, Rsk, and S6K.

Solution to Problem

The present inventors have conducted concentrated studies in order to attain the objects. As a result, they discovered that a compound comprising 5H-pyrrolo[2,3-d]pyrimidin-6

(7H)-one as a basic structure, which has a 6-membered nitrogen-containing unsaturated heterocycle at position 4 thereof via piperazine or piperidine, and a particular substituent in the unsaturated heterocycle, has excellent inhibitory activity and/or cancer cell growth suppression activity against at least one kinase selected from the group consisting of Akt, Rsk, and S6K, and/or such compound is useful as a medicine for the treatment of various diseases (cancer, in particular) associated with at least one kinase selected from the group consisting of Akt, Rsk, and S6K. This has led to the completion of the present invention.

The present invention includes the following.

[1] A compound represented by Formula (I) or a salt thereof:

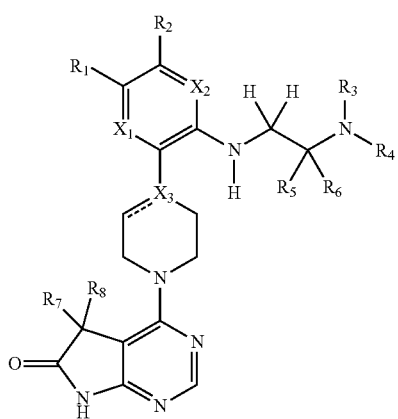

(I)

wherein $R_1$ represents an optionally substituted 4- to 6-membered monocyclic unsaturated heterocyclic group having 1 to 3 hetero atoms selected from among N, S, and O;

$R_2$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group;

$R_3$, $R_4$, and $R_5$, which may be the same or different, each represent a hydrogen atom, a C1-C6 alkyl group, a C1-C6 haloalkyl group, or a C3-C6 cycloalkyl group; or $R_3$ and $R_4$, together with a nitrogen atom to which they are bound, form a 4- to 6-membered monocyclic saturated heterocycle having 1 to 3 hetero atoms selected from among N, S, and O, and $R_5$ represents a hydrogen atom, a C1-C6 alkyl group, a C1-C6 haloalkyl group, or a C3-C6 cycloalkyl group; or $R_4$ and $R_5$, together with a nitrogen atom to which they are bound and a carbon atom adjacent thereto, form a 4- to 6-membered monocyclic saturated heterocycle having 1 to 3 hetero atoms selected from among N, S, and O, and $R_3$ represents a hydrogen atom, a C1-C6 alkyl group, a C1-C6 haloalkyl group, or a C3-C6 cycloalkyl group;

$R_6$ represents a hydrogen atom, a C1-C6 alkyl group, a C1-C6 haloalkyl group, or a C3-C6 cycloalkyl group;

$R_7$ and $R_8$, which may be the same or different, each represent a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group; or $R_7$ and $R_8$, together with a carbon atom to which they are bound, form a C3-C10 cycloalkyl group;

$X_1$ and $X_2$, which may be the same or different, each represent N or $CR_9$, and $R_9$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group; and $X_3$ represents N or CH when a broken line (┄) indicates a single bond, or C when a broken line indicates a double bond, provided that at least either one of $X_1$ or $X_2$ represents N.

[2] The compound or the salt thereof according to [1], wherein $R_1$ represents a 4- to 6-membered monocyclic unsaturated heterocyclic group having 1 to 3 hetero atoms selected from among N, S, and O, which may comprise 1 to 3 substituents selected from among a halogen atom, a C1-C6 alkyl group, a C1-C6 haloalkyl group, a C1-C6 alkoxy group, and a C3-C10 cycloalkyl group.

[3] The compound or the salt thereof according to [1] or [2], wherein $R_2$ represents a hydrogen atom or a halogen atom, $R_6$ represents a hydrogen atom, $R_7$ represents a C1-C6 alkyl group, $R_8$ represents a hydrogen atom or a C1-C6 alkyl group, $X_1$ represents N or $CR_9$, $R_9$ represents a hydrogen atom or a halogen atom, and $X_2$ represents N or CH.

[4] The compound or the salt thereof according to any of [1] to [3], wherein $R_1$ represents a furanyl group, a thienyl group, a thiazolyl group, a thiadiazolyl group, an oxazolyl group, an oxadiazolyl group, a pyridinyl group, or a pyrazolyl group, which may comprise 1 to 3 substituents selected from among a halogen atom, a C1-C6 alkyl group, a C1-C6 haloalkyl group, a C1-C6 alkoxy group, and a C3-C10 cycloalkyl group.

[5] The compound or the salt thereof according to any of [1] to [4], wherein $R_3$, $R_4$, and $R_5$, which may be the same or different, each represent a hydrogen atom or a C1-C6 alkyl group; or $R_3$ and $R_4$, together with a nitrogen atom to which they are bound, form a 4- to 6-membered monocyclic saturated heterocycle having a nitrogen atom, and $R_5$ represents a hydrogen atom or a C1-C6 alkyl group; or $R_4$ and $R_5$, together with a nitrogen atom to which they are bound and a carbon atom adjacent thereto, form a 4- to 6-membered monocyclic saturated heterocycle having a nitrogen atom, and $R_3$ represents a hydrogen atom or a C1-C6 alkyl group.

[6] The compound or the salt thereof according to any of [1] to [5], wherein $R_1$ represents a pyridinyl group having a halogen atom or a C1-C6 alkoxy group, a pyrazolyl group having a C1-C6 alkyl group and a C1-C6 haloalkyl group, an oxadiazolyl group having a C1-C6 haloalkyl group, or an unsubstituted furanyl group or thiazolyl group, $R_2$, $R_5$ and $R_6$ each represent a hydrogen atom, $R_3$ represents a hydrogen atom, and $R_4$ represents a C1-C6 alkyl group; or $R_3$ and $R_4$, together with a nitrogen atom to which they are bound, form a 4- to 6-membered monocyclic saturated heterocycle having a nitrogen atom, $R_7$ represents a C1-C6 alkyl group, $R_8$ represents a hydrogen atom or a C1-C6 alkyl group, and $X_1$ and $X_2$, which may be different from each other, each represent N or CH; and a broken line (┄) indicates a single bond and $X_3$ represents CH.

[7] The compound or the salt thereof according to [6], wherein $R_1$ represents a pyrazolyl group having a C1-C6 alkyl group and a C1-C6 haloalkyl group, or an oxadiazolyl group having a C1-C6 haloalkyl group.

[8] The compound or the salt thereof according to any of [1] to [7], wherein the compound is selected from the compounds indicated below:

4-(4-(6-(5-(difluoromethyl)-1,3,4-oxadiazol-2-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one;

4-(4-(3-((2-(tert-butylamino)ethyl)amino)-6-(5-(trifluoromethyl)-1,3,4-oxadiazol-2-yl)pyridin-2-yl)piperidin-1l-yl)-5,5-dimethyl-5H-pyrrolo[2,3-d]pyrimidin-6(7H)-one; and 4-(4-(3-((2-(tert-butylamino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one.

[9] An Akt inhibitor comprising, as an active ingredient, the compound or the salt thereof according to any of [1] to [8].

[10] An Rsk inhibitor comprising, as an active ingredient, the compound or the salt thereof according to any of [1] to [8].

[11] An S6K inhibitor comprising, as an active ingredient, the compound or the salt thereof according to any of [1] to [8].

[12] An inhibitor against at least two kinases selected from the group consisting of Akt, Rsk, and S6K comprising, as an active ingredient, the compound or the salt thereof according to any of [1] to [8].

[13] An inhibitor against Akt, Rsk, and S6K comprising, as an active ingredient, the compound or the salt thereof according to any of [1] to [8].

[14] A pharmaceutical composition for the treatment of a disease associated with Akt comprising, as an active ingredient, the compound or the salt thereof according to any of [1] to [8].

[15] A pharmaceutical composition for the treatment of a disease associated with Rsk comprising, as an active ingredient, the compound or the salt thereof according to any of [1] to [8].

[16] A pharmaceutical composition for the treatment of a disease associated with S6K comprising, as an active ingredient, the compound or the salt thereof according to any of [1] to [8].

[17] A pharmaceutical composition for the treatment of a disease associated with at least two kinases selected from the group consisting of Akt, Rsk, and S6K comprising, as an active ingredient, the compound or the salt thereof according to any of [1] to [8].

[18] A pharmaceutical composition for the treatment of a disease associated with Akt, Rsk, and S6K comprising, as an active ingredient, the compound or the salt thereof according to any of [1] to [8].

[19] An anti-tumor agent comprising, as an active ingredient, the compound or the salt thereof according to any of [1] to [8].

The present invention further encompasses the following.

[20-1] The compound or the salt thereof according to any of [1] to [8] for use in the inhibition of Akt.

[20-2] The compound or the salt thereof according to any of [1] to [8] for use in the inhibition of Rsk.

[20-3] The compound or the salt thereof according to any of [1] to [8] for use in the inhibition of S6K.

[20-4] The compound or the salt thereof according to any of [1] to [8] for use in the inhibition of at least two kinases selected from the group consisting of Akt, Rsk, and S6K.

[20-5] The compound or the salt thereof according to any of [1] to [8] for use in the inhibition of Akt, Rsk, and S6K.

[21-1] The compound or the salt thereof according to any of [1] to [8] for use in the treatment of a disease associated with Akt.

[21-2] The compound or the salt thereof according to any of [1] to [8] for use in the treatment of a disease associated with Rsk.

[21-3] The compound or the salt thereof according to any of [1] to [8] for use in the treatment of a disease associated with S6K.

[21-4] The compound or the salt thereof according to any of [1] to [8] for use in the treatment of a disease associated with at least two kinases selected from the group consisting of Akt, Rsk, and S6K.

[21-5] The compound or the salt thereof according to any of [1] to [8] for use in the treatment of a disease associated with Akt, Rsk, and S6K.

[22] The compound or the salt thereof according to any of [1] to [8] for use in the treatment of a tumor.

[23-1] Use of the compound or the salt thereof according to any of [1] to [8] in the inhibition of Akt.

[23-2] Use of the compound or the salt thereof according to any of [1] to [8] in the inhibition of Rsk.

[23-3] Use of the compound or the salt thereof according to any of [1] to [8] in the inhibition of S6K.

[23-4] Use of the compound or the salt thereof according to any of [1] to [8] in the inhibition of at least two kinases selected from the group consisting of Akt, Rsk, and S6K.

[23-5] Use of the compound or the salt thereof according to any of [1] to [8] in the inhibition of Akt, Rsk, and S6K.

[24-1] Use of the compound or the salt thereof according to any of [1] to [8] in the treatment of a disease associated with Akt.

[24-2] Use of the compound or the salt thereof according to any of [1] to [8] in the treatment of a disease associated with Rsk.

[24-3] Use of the compound or the salt thereof according to any of [1] to [8] in the treatment of a disease associated with S6K.

[24-4] Use of the compound or the salt thereof according to any of [1] to [8] in the treatment of a disease associated with at least two kinases selected from the group consisting of Akt, Rsk, and S6K.

[24-5] Use of the compound or the salt thereof according to any of [1] to [8] in the treatment of a disease associated with Akt, Rsk, and S6K.

[25] Use of the compound or the salt thereof according to any of [1] to [8] in the treatment of a tumor.

[26-1] Use of the compound or the salt thereof according to any of [1] to [8] in the manufacture of a medicament for the inhibition of Akt.

[26-2] Use of the compound or the salt thereof according to any of [1] to [8] in the manufacture of a medicament for the inhibition of Rsk.

[26-3] Use of the compound or the salt thereof according to any of [1] to [8] in the manufacture of a medicament for the inhibition of S6K.

[26-4] Use of the compound or the salt thereof according to any of [1] to [8] in the manufacture of a medicament for the inhibition of at least two kinases selected from the group consisting of Akt, Rsk, and S6K.

[26-5] Use of the compound or the salt thereof according to any of [1] to [8] in the manufacture of a medicament for the inhibition of Akt, Rsk, and S6K.

[27-1] Use of the compound or the salt thereof according to any of [1] to [8] in the manufacture of a medicament for the treatment of a disease associated with Akt.

[27-2] Use of the compound or the salt thereof according to any of [1] to [8] in the manufacture of a medicament for the treatment of a disease associated with Rsk.

[27-3] Use of the compound or the salt thereof according to any of [1] to [8] in the manufacture of a medicament for the treatment of a disease associated with S6K.

[27-4] Use of the compound or the salt thereof according to any of [1] to [8] in the manufacture of a medicament for the treatment of a disease associated with at least two kinases selected from the group consisting of Akt, Rsk, and S6K.
[27-5] Use of the compound or the salt thereof according to any of [1] to [8] in the manufacture of a medicament for the treatment of a disease associated with Akt, Rsk, and S6K.
[28] Use of the compound or the salt thereof according to any of [1] to [8] in the manufacture of a medicament for the treatment of a tumor.
[29-1] A method for the inhibition of Akt comprising administering an effective amount of the compound or the salt thereof according to any of [1] to [8] to a patient in need thereof.
[29-2] A method for the inhibition of Rsk comprising administering an effective amount of the compound or the salt thereof according to any of [1] to [8] to a patient in need thereof.
[29-3] A method for the inhibition of S6K comprising administering an effective amount of the compound or the salt thereof according to any of [1] to [8] to a patient in need thereof.
[29-4] A method for the inhibition of at least two kinases selected from the group consisting of Akt, Rsk, and S6K comprising administering an effective amount of the compound or the salt thereof according to any of [1] to [8] to a patient in need thereof.
[29-5] A method for the inhibition of Akt, Rsk, and S6K comprising administering an effective amount of the compound or the salt thereof according to any of [1] to [8] to a patient in need thereof.
[30-1] A method for the treatment of a disease associated with Akt comprising administering an effective amount of the compound or the salt thereof according to any of [1] to [8] to a patient in need thereof.
[30-2] A method for the treatment of a disease associated with Rsk comprising administering an effective amount of the compound or the salt thereof according to any of [1] to [8] to a patient in need thereof.
[30-3] A method for the treatment of a disease associated with S6K comprising administering an effective amount of the compound or the salt thereof according to any of [1] to [8] to a patient in need thereof.
[30-4] A method for the treatment of a disease associated with at least two kinases selected from the group consisting of Akt, Rsk, and S6K comprising administering an effective amount of the compound or the salt thereof according to any of [1] to [8] to a patient in need thereof.
[30-5] A method for the treatment of a disease associated with Akt, Rsk, and S6K comprising administering an effective amount of the compound or the salt thereof according to any of [1] to [8] to a patient in need thereof.
[31] A method for the treatment of a tumor comprising administering an effective amount of the compound or the salt thereof according to any of [1] to [8] to a patient in need thereof.

This description includes part or all of the content as disclosed in the description and/or drawings of Japanese Patent Application No. 2016-101599, which is a priority document of the present application.

Effects of the Invention

The present invention provides a novel 5H-pyrrolo[2,3-d]pyrimidin-6(7H)-one derivative, an inhibitor against at least one kinase selected from the group consisting of Akt, Rsk, and S6K, a pharmaceutical composition for the treatment of a disease associated with at least one kinase selected from the group consisting of Akt, Rsk, and S6K, or an anti-tumor agent.

According to an embodiment, the compound or the salt thereof according to the present invention was found to have excellent inhibitory activity against at least one kinase selected from the group consisting of Akt, Rsk, and S6K, and exert growth suppression effects on cancer cell lines. Accordingly, the compound or the salt thereof according to the present invention is useful for an agent for the prevention and/or treatment of a disease associated with at least one kinase selected from the group consisting of Akt, Rsk, and S6K, such as cancer.

EMBODIMENTS OF THE INVENTION

The compound represented by Formula (I) according to the present invention comprises 5H-pyrrolo[2,3-d]pyrimidin-6(7H)-one as a basic structure, which has a 6-membered nitrogen-containing unsaturated heterocycle at position 4 thereof via piperazine or piperidine, and a particular substituent in the unsaturated heterocycle. This compound is a novel compound that is not described in any of the prior art documents mentioned above.

Examples of "substituents" used herein include a halogen atom, a hydroxyl group, a cyano group, a nitro group, a C1-C6 alkyl group, a C1-C6 haloalkyl group, a C3-C10 cycloalkyl group, a C2-C6 alkenyl group, a C2-C6 alkynyl group, a C1-C6 alkoxy group, an amino group, a mono- or dialkylamino group, an acyl group, a carboxyl group, an alkoxycarbonyl group, a carbamoyl group, a 4- to 10-membered saturated or unsaturated heterocyclic group having 1 to 4 hetero atoms selected from among N, S, and O, and a C6-C14 aromatic hydrocarbon group. When the substituent is present, the number thereof is typically 1 to 3.

Specific examples of "halogen atom" herein include chlorine, bromine, fluorine, and iodine atoms, with chlorine and fluorine atoms being preferable and a fluorine atom being more preferable.

The term "C1-C6 alkyl group" used herein refers to a linear or branched saturated hydrocarbon group having 1 to 6 carbon atoms. Specific examples thereof include methyl, ethyl, n-propyl, isopropyl, n-butyl, isobutyl, sec-butyl, tert-butyl, pentyl, and hexyl groups, with a linear alkyl group having 1 to 4 carbon atoms or a branched alkyl group having 3 or 4 carbon atoms being preferable, and methyl, isopropyl, and tert-butyl groups being more preferable.

The term "C2-C6 alkenyl group" used herein refers to a linear or branched hydrocarbon group having 2 to 6 carbon atoms that contains at least one carbon-carbon double bond. Specific examples thereof include vinyl, allyl, methylvinyl, propenyl, butenyl, pentenyl, and hexenyl groups, with a linear or branched hydrocarbon group having 2 to 4 carbon atoms that contains at least one carbon-carbon double bond being preferable.

The term "C2-C6 alkynyl group" used herein refers to a linear or branched hydrocarbon group having 2 to 6 carbon atoms that contains at least one carbon-carbon triple bond. Specific examples thereof include ethynyl and 2-propynyl groups, with a linear or branched hydrocarbon group having 2 to 4 carbon atoms that contains at least one carbon-carbon triple bond being preferable.

The term "C1-C6 haloalkyl group" used herein refers to a linear or branched saturated hydrocarbon group having 1 to 6 carbon atoms in which one to all hydrogen atoms are substituted with the halogen atom. Specific examples thereof include monofluoromethyl, difluoromethyl, trifluoromethyl, 1-fluoroethyl, 2-fluoroethyl, 1,1-difluoroethyl, 1,2-difluoroethyl, 2,2-difluoroethyl, and 2,2,2-trifluoroethyl groups, with a linear or branched saturated hydrocarbon group having 1 to 6 carbon atoms in which 1 to 3 hydrogen atoms are substituted with the halogen atom with being preferable, and difluoromethyl and trifluoromethyl groups being more preferable.

The term "C1-C6 alkoxy group" used herein refers to an oxy group to which a linear or branched saturated hydrocarbon group having 1 to 6 carbon atoms has been bound. Specific examples thereof include methoxy, ethoxy, n-propoxy, isopropoxy, n-butoxy, isobutoxy, and tert-butoxy groups, with an oxy group to which a linear or branched saturated hydrocarbon group having 1 to 4 carbon atoms has bound being preferable, and a methoxy group being more preferable.

The term "C3-C10 cycloalkyl group" used herein refers to a monocyclic or polycyclic saturated hydrocarbon group having 3 to 10 carbon atoms. Specific examples thereof include cyclopropyl, cyclobutyl, cyclopentyl, cyclohexyl, cycloheptyl, and decaryl groups, with a monocyclic saturated hydrocarbon group having 3 to 6 carbon atoms being preferable, and a cyclopropyl group being more preferable.

The term "4- to 10-membered saturated heterocyclic group" used herein refers to a 4- to 10-membered monocyclic or polycyclic fully saturated heterocyclic group. Specific examples thereof include azetidinyl, pyrrolidinyl, piperidinyl, piperazinyl, hexamethyleneimino, morpholino, thiomorpholino, homopiperazinyl, tetrahydrofuranyl, and tetrahydropyranyl groups, with a 4- to 10-membered monocyclic or polycyclic fully saturated heterocyclic group having 1 to 4 hetero atoms selected from among N, S, and O being preferable.

The term "4- to 6-membered monocyclic saturated heterocyclic group" used herein refers to a 4- to 6-membered monocyclic fully saturated heterocyclic group. Specific examples thereof include azetidinyl, pyrrolidinyl, piperidinyl, piperazinyl, hexamethyleneimino, morpholino, and thiomorpholino groups, with a 4- to 6-membered monocyclic fully saturated heterocyclic group having 1 to 4 hetero atoms selected from among N, S, and O being preferable, a 5- to 6-membered monocyclic fully saturated heterocyclic group having 1 to 3 hetero atoms selected from among N, S, and O being more preferable, and a pyrrolidinyl group being particularly preferable.

The term "4- to 10-membered unsaturated heterocyclic group" used herein refers to a 4- to 10-membered monocyclic or polycyclic fully unsaturated or partially saturated heterocyclic group. Specific examples of fully unsaturated heterocyclic groups include pyrrolyl, imidazolyl, pyrazolyl, triazolyl, tetrazolyl, furanyl, oxazolyl, isoxazolyl, oxadiazolyl, thienyl, thiazolyl, isothiazolyl, thiadiazolyl, pyridinyl, pyrimidinyl, pyrazinyl, pyridazinyl, indolyl, isoindolyl, indazolyl, benzimidazolyl, benzotriazolyl, azaindolyl, pyrrolopyridinyl, imidazopyridinyl, pyrazolopyridinyl, triazopyridinyl, pyrrolopyrimidinyl, imidazopyrimidinyl, pyrazolopyrimidinyl, benzofuranyl, benzoxazolyl, benzothiophenyl, benzothiazolyl, quinolyl, isoquinolyl, quinazolinyl, and quinoxalinyl groups. Specific examples of partially saturated heterocyclic groups include indolinyl, methylenedioxyphenyl, ethylenedioxyphenyl, and dihydrobenzofuranyl groups. A 4- to 10-membered monocyclic or polycyclic fully unsaturated or partially saturated heterocyclic group having 1 to 4 hetero atoms selected from among N, S, and O is preferable.

The term "4- to 6-membered monocyclic unsaturated heterocyclic group" used herein refers to a 4- to 6-membered monocyclic fully unsaturated or partially unsaturated heterocyclic group. Specific examples of fully unsaturated heterocyclic groups include pyrrolyl, imidazolyl, pyrazolyl, triazolyl, tetrazolyl, furanyl, oxazolyl, isoxazolyl, oxadiazolyl, thienyl, thiazolyl, isothiazolyl, thiadiazolyl, pyridinyl, pyrimidinyl, and pyridazinyl groups. Specific examples of partially unsaturated heterocyclic groups include tetradihydrofuranyl, dihydropyranyl, dihydrothienyl, tetrahydropyridinyl, and dihydrothiopyranyl groups. A 4- to 6-membered monocyclic fully unsaturated heterocyclic group having 1 to 4 hetero atoms selected from among N, S, and O is preferable, a 5- to 6-membered monocyclic fully unsaturated heterocyclic group having 1 to 3 hetero atoms selected from among N, S, and O is more preferable, and pyridinyl, pyrazolyl, thiazolyl, oxazolyl, oxadiazolyl, thiadiazolyl, furanyl, and thienyl groups are more preferable.

The term "C6-C14 aromatic hydrocarbon group" used herein refers to a monocyclic or polycyclic aromatic hydrocarbon group having 6 to 14 carbon groups. Specific examples thereof include phenyl, naphthyl, tetrahydronaphthyl, and anthracenyl groups.

In Formula (I), $R_1$ represents "an optionally substituted 4- to 6-membered monocyclic unsaturated heterocyclic group having 1 to 3 heteroatoms selected from among N, S, and 0."

An example of "a 4- to 6-membered monocyclic unsaturated heterocyclic group having 1 to 3 heteroatoms selected from among N, S, and O" represented by $R_1$ is the "4- to 6-membered monocyclic unsaturated heterocyclic group" described above. A 5- to 6-membered monocyclic fully unsaturated heterocyclic group having 1 to 3 hetero atoms selected from among N, S, and O is preferable, and pyridinyl, pyrazolyl, thiazolyl, oxazolyl, oxadiazolyl, thiadiazolyl, furanyl, and thienyl groups are more preferable.

"A 4- to 6-membered monocyclic unsaturated heterocyclic group having 1 to 3 heteroatoms selected from among N, S, and O" may or may not be substituted. The number of substituents is preferably 1 to 3. The "substituents" mentioned above can be used herein. A substituent can be preferably selected from the group consisting of a halogen atom, a C1-C6 alkyl group, a C1-C6 alkoxy group, a C1-C6 haloalkyl group, and a C3-C10 cycloalkyl group, more preferably selected from the group consisting of a halogen atom, a C1-C6 alkyl group, a C1-C6 alkoxy group, and a C1-C6 haloalkyl group, and further preferably a C1-C6 alkyl group and/or a C1-C6 haloalkyl group.

In Formula (I), $R_1$ preferably represents a 4- to 6-membered monocyclic unsaturated heterocyclic group having 1 to 3 heteroatoms selected from among N, S, and O, which may comprise 1 to 3 substituents selected from the group consisting of a halogen atom, a C1-C6 alkyl group, a C1-C6 haloalkyl group, a C1-C6 alkoxy group, and a C3-C10 cycloalkyl group.

In Formula (I), $R_1$ further preferably represents a furanyl group, a thienyl group, a thiazolyl group, a thiadiazolyl group, an oxazolyl group, an oxadiazolyl group, a pyridinyl group, or a pyrazolyl group, which may comprise 1 to 3 substituents selected from among a halogen atom, a C1-C6 alkyl group, a C1-C6 haloalkyl group, a C1-C6 alkoxy group, and a C3-C10 cycloalkyl group.

In Formula (I), $R_1$ further preferably represents a pyridinyl group, a pyrazolyl group, a thiazolyl group, an oxadiazolyl group, or a thiadiazolyl group having 1 to 3 substituents selected from among a halogen atom, a C1-C6 alkyl group, a C1-C6 haloalkyl group, a C1-C6 alkoxy group, and a C3-C10 cycloalkyl group or an unsubstituted furanyl, thienyl, thiazolyl, or oxazolyl group.

In Formula (I), $R_1$ further preferably represents a pyridinyl group having a halogen atom or a C1-C6 alkoxy group, a pyrazolyl group having a C1-C6 alkyl group and a C1-C6 haloalkyl group, an oxadiazolyl group having a C1-C6 haloalkyl group or an unsubstituted furanyl or thiazolyl group.

In Formula (I), $R_1$ particularly preferably represents a pyrazolyl group having a C1-C6 alkyl group and a C1-C6 haloalkyl group or an oxadiazolyl group having a C1-C6 haloalkyl group.

In Formula (I), $R_2$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group.

In Formula (I), $R_2$ preferably represents a hydrogen atom, a halogen atom, or a C1-C6 alkyl group, more preferably a hydrogen atom or a halogen atom, and particularly preferably a hydrogen atom.

In Formula (I), $R_3$, $R_4$, and $R_5$, which may be the same or different, each represent a hydrogen atom, a C1-C6 alkyl group, a C1-C6 haloalkyl group, or a C3-C6 cycloalkyl group. Alternatively, $R_3$ and $R_4$, together with a nitrogen atom to which they are bound, form a 4- to 6-membered monocyclic saturated heterocycle having 1 to 3 hetero atoms selected from among N, S, and O, and $R_5$ represents a hydrogen atom, a C1-C6 alkyl group, a C1-C6 haloalkyl group, or a C3-C6 cycloalkyl group; or $R_4$ and $R_5$, together with a nitrogen atom to which they are bound and a carbon atom adjacent thereto, form a 4- to 6-membered monocyclic saturated heterocycle having 1 to 3 hetero atoms selected from among N, S, and O, and $R_3$ represents a hydrogen atom, a C1-C6 alkyl group, a C1-C6 haloalkyl group, or a C3-C6 cycloalkyl group.

In Formula (I), an example of "$R_3$ and $R_4$, together with a nitrogen atom to which they are bound, form a 4- to 6-membered monocyclic saturated heterocycle having 1 to 3 hetero atoms selected from among N, S, and O" is to form the "4- to 6-membered monocyclic saturated heterocycle" described above. It is preferably a 4- to 6-membered monocyclic saturated heterocycle comprising a nitrogen atom, and particularly preferably a pyrrolidinyl group.

In Formula (I), an example of "$R_4$ and $R_5$, together with a nitrogen atom to which they are bound and a carbon atom adjacent thereto, form a 4- to 6-membered monocyclic saturated heterocycle having 1 to 3 hetero atoms selected from among N, S, and O" is to form "the 4- to 6-membered monocyclic saturated heterocycle. It is preferably a 4- to 6-membered monocyclic saturated heterocycle comprising one nitrogen atom, and particularly preferably a pyrrolidinyl group.

In Formula (I), preferably, $R_3$, $R_4$, and $R_5$, which may be the same or different, each represent a hydrogen atom or a C1-C6 alkyl group. Alternatively, $R_3$ and $R_4$, together with a nitrogen atom to which they are bound, form a 4- to 6-membered monocyclic saturated heterocycle having a nitrogen atom, and $R_5$ represents a hydrogen atom or a C1-C6 alkyl group; or $R_4$ and $R_5$, together with a nitrogen atom to which they are bound and a carbon atom adjacent thereto, form a 4- to 6-membered monocyclic saturated heterocycle having a nitrogen atom, and $R_3$ represents a hydrogen atom or a C1-C6 alkyl group.

In Formula (I), particularly preferably, $R_3$ and $R_5$ each represent a hydrogen atom, and $R_4$ represents a C1-C6 alkyl group; or $R_3$ and $R_4$, together with a nitrogen atom to which they are bound, form a 4- to 6-membered monocyclic saturated heterocycle, and $R_5$ represents a hydrogen atom.

In Formula (I), $R_6$ represents a hydrogen atom, a C1-C6 alkyl group, a C1-C6 haloalkyl group, or a C3-C6 cycloalkyl group.

In Formula (I), $R_6$ preferably represents a hydrogen atom or a C1-C6 alkyl group, and particularly preferably a hydrogen atom.

In Formula (I), $R_7$ and $R_8$, which may be the same or different, each represent a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group; or $R_7$ and $R_8$, together with a carbon atom to which they are bound, form a C3-C10 cycloalkyl group.

In Formula (I), preferably, $R_7$ and $R_8$, which may be the same or different, each represent a hydrogen atom or a C1-C6 alkyl group. In Formula (I), more preferably, $R_7$ represents a C1-C6 alkyl group and $R_8$ represents a hydrogen atom or a C1-C6 alkyl group. It is particularly preferable that $R_7$ represent a methyl group and $R_8$ represent a hydrogen atom or a methyl group.

In Formula (I), $X_1$ and $X_2$, which may be the same or different, each represent N or $CR_9$, and $R_9$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group, provided that at least either $X_1$ or $X_2$ represents N.

In Formula (I), preferably, $X_1$ represents N or $CR_9$, $R_9$ represents a hydrogen atom, a halogen atom, or a C1-C6 alkyl group, and $X_2$ represents N or CH, provided that at least either $X_1$ or $X_2$ represents N. More preferably, $X_1$ represents N and $X_2$ represents CH. Alternatively, $X_1$ represents $CR_9$, $R_9$ represents a hydrogen atom or a halogen atom, and $X_2$ represents N. Further preferably, $X_1$ and $X_2$, which may be different from each other, each represent N or CH. Particularly preferably, $X_1$ represents N, and $X_2$ represents CH.

In Formula (I), $X_3$ represents N or CH when a broken line (┄) indicates a single bond, or C when a broken line indicates a double bond. In Formula (I), $X_3$ preferably represents CH when a broken line (┄) indicates a single bond, or C when a broken line indicates a double bond. It is particularly preferable that a broken line (┄) indicates a single bond and $X_3$ represents CH.

A preferable compound according to the present invention is represented by Formula (I):
wherein $R_1$ represents a 4- to 6-membered monocyclic unsaturated heterocyclic group having 1 to 3 hetero atoms selected from among N, S, and O, which may comprise 1 to 3 substituents selected from among a halogen atom, a C1-C6 alkyl group, a C1-C6 haloalkyl group, a C1-C6 alkoxy group, and a C3-C10 cycloalkyl group;

$R_2$ represents a hydrogen atom or a halogen atom;

$R_3$, $R_4$, and $R_5$, which may be the same or different, each represent a hydrogen atom or a C1-C6 alkyl group; or $R_3$ and $R_4$, together with a nitrogen atom to which they are bound, form a 4- to 6-membered monocyclic saturated heterocycle having a nitrogen atom, and $R_5$ represents a hydrogen atom or a C1-C6 alkyl group; or $R_4$ and $R_5$, together with a nitrogen atom to which they are bound and a carbon atom adjacent thereto, form a 4- to 6-membered monocyclic saturated heterocycle having a nitrogen atom, and $R_3$ represents a hydrogen atom or a C1-C6 alkyl group; or $R_3$ and $R_5$ each represent a hydrogen atom and $R_4$ represents a C1-C6 alkyl group; or $R_3$ and $R_4$, together with a nitrogen atom to which they are bound, form a 4- to 6-membered monocyclic saturated heterocycle having a nitrogen atom, and $R_5$ represents a hydrogen atom;

$R_6$ represents a hydrogen atom;

$R_7$ represents a C1-C6 alkyl group and $R_8$ represents a hydrogen atom or a C1-C6 alkyl group;

$X_1$ and $X_2$, which may be different from each other, each represent N or CH; and a broken line (----) indicates a single bond and $X_3$ represents CH.

In such compound, more preferably, $R_1$ represents a furanyl group, a thienyl group, a thiazolyl group, a thiadiazolyl group, an oxazolyl group, an oxadiazolyl group, a pyridinyl group, or a pyrazolyl group, which may comprise 1 to 3 substituents selected from among a halogen atom, a C1-C6 alkyl group, a C1-C6 haloalkyl group, a C1-C6 alkoxy group, and a C3-C10 cycloalkyl group;

$R_2$ and $R_6$ each represent a hydrogen atom;

$R_3$, $R_4$, and $R_5$, which may be the same or different, each represent a hydrogen atom or a C1-C6 alkyl group; or $R_3$ and $R_4$, together with a nitrogen atom to which they are bound, form a 4- to 6-membered monocyclic saturated heterocycle having a nitrogen atom, and $R_5$ represents a hydrogen atom or a C1-C6 alkyl group; or $R_4$ and $R_5$, together with a nitrogen atom to which they are bound and a carbon atom adjacent thereto, form a 4- to 6-membered monocyclic saturated heterocycle having a nitrogen atom, and $R_3$ represents a hydrogen atom or a C1-C6 alkyl group; or $R_3$ and $R_5$ each represent a hydrogen atom, and $R_4$ represents a C1-C6 alkyl group; or $R_3$ and $R_4$, together with a nitrogen atom to which they are bound, form a 4- to 6-membered monocyclic saturated heterocycle having a nitrogen atom, and $R_5$ represents a hydrogen atom;

$R_7$ represents a C1-C6 alkyl group and $R_8$ represents a hydrogen atom or a C1-C6 alkyl group;

$X_1$ and $X_2$, which may be different from each other, each represent N or CH; and a broken line (----) indicates a single bond and $X_3$ represents CH.

In Formula (I), more preferably, $R_1$ represents a pyridinyl group having a halogen atom or a C1-C6 alkoxy group, a pyrazolyl group having a C1-C6 alkyl group and a C1-C6 haloalkyl group, an oxadiazolyl group having a C1-C6 haloalkyl group, or an unsubstituted furanyl or thiazolyl group;

$R_2$, $R_5$, and $R_6$ each represent a hydrogen atom;

$R_3$ represents a hydrogen atom and $R_4$ represents a C1-C6 alkyl group; or $R_3$ and $R_4$, together with a nitrogen atom to which they are bound, form a 4- to 6-membered monocyclic saturated heterocycle having a nitrogen atom;

$R_7$ represents a C1-C6 alkyl group and $R_8$ represents a hydrogen atom or a C1-C6 alkyl group;

$X_1$ and $X_2$, which may be different from each other, each represent N or CH; and a broken line (----) indicates a single bond and $X_3$ represents CH.

More preferably, $R_1$ represents a pyrazolyl group having a C1-C6 alkyl group and a C1-C6 haloalkyl group, or an oxadiazolyl group having a C1-C6 haloalkyl group;

$R_2$, $R_5$, and $R_6$ each represent a hydrogen atom;

$R_3$ represents a hydrogen atom, and $R_4$ represents a C1-C6 alkyl group; or $R_3$ and $R_4$, together with a nitrogen atom to which they are bound, form a 4- to 6-membered monocyclic saturated heterocycle having a nitrogen atom;

$R_7$ represents a C1-C6 alkyl group, and $R_8$ represents a hydrogen atom or a C1-C6 alkyl group;

$X_1$ and $X_2$, which may be different from each other, each represent N or CH; and a broken line (----) indicates a single bond and $X_3$ represents CH.

Further preferably, $R_1$ represents a pyrazolyl group having a methyl group and a trifluoromethyl group or an oxadiazolyl group having a difluoromethyl group;

$R_2$, $R_5$, and $R_6$ each represent a hydrogen atom;

$R_3$ represents a hydrogen atom, and $R_4$ represents an isopropyl or tert-butyl group; or $R_3$ and $R_4$, together with a nitrogen atom to which they are bound, form a pyrrolidinyl group;

$R_7$ represents a methyl, and $R_8$ represents a hydrogen atom or a methyl group;

$X_1$ and $X_2$, which may be different from each other, each represent N or CH; and a broken line (----) indicates a single bond and $X_3$ represents CH.

Specific examples of the compound according to the present invention include compounds produced in the following examples, although the compounds are not limited thereto.

Examples of preferable compounds according to the present invention include the following compounds:

4-(4-(5-((2-(tert-butylamino)ethyl)amino)-5'-fluoro-[2,3'-bipyridin]-6-yl)piperidin-1-yl)-5,5-dimethyl-5H-pyrrolo[2,3-d]pyrimidin-6(7H)-one (Compound (1));

4-(4-(2'-fluoro-5-((2-(pyrrolidin-1-yl)ethyl)amino)-[2,4'-bipyridin]-6-yl)piperidin-1-yl)-5-methyl-5H-pyrrolo[2,3-d]pyrimidin-6(7H)-one (Compound (13));

4-(4-(6-(furan-3-yl)-3-((2-(pyrrolidin-1-yl)ethyl)amino)pyridin-2-yl)piperidin-1-yl)-5-methyl-5H-pyrrolo[2,3-d]pyrimidin-6(7H)-one (Compound 14);

4-(4-(5-((2-(isopropylamino)ethyl)amino)-5'-methoxy-[2,3'-bipyridin]-6-yl)piperidin-1-yl)-5-methyl-5H-pyrrolo[2,3-d]pyrimidin-6(7H)-one (Compound (15));

5-methyl-4-(4-(3-((2-(pyrrolidin-1-yl)ethyl)amino)-6-(thiazol-2-yl)pyridin-2-yl)piperidin-1-yl)-5H-pyrrolo[2,3-d]pyrimidin-6(7H)-one (Compound (24));

4-(5-fluoro-5'-((2-(pyrrolidin-1-yl)ethyl)amino)-5",6"-dihydro-[3,2':6',4"-terpyridine-]-1"(2"H)-yl)-5-methyl-5H-pyrrolo[2,3-d]pyrimidin-6(7H)-one (Compound (26));

5-methyl-4-(4-(5-(1-methyl-3-(trifluoromethyl)-1H-pyrazol-5-yl)-2-((2-(pyrrolidin-1-yl)ethyl)amino)pyridin-3-yl)piperidin-1-yl)-5H-pyrrolo[2,3-d]pyrimidin-6(7H)-one (Compound (27));

4-(4-(6-(5-(difluoromethyl)-1,3,4-oxadiazol-2-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one (Compound (30));

4-(4-(3-((2-(tert-butylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (32));

4-(4-(3-((2-(tert-butylamino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one (Compound (41)); and 5,5-dimethyl-4-(4-(3-((2-(pyrrolidin-1-yl)ethyl)amino)-6-(3-(trifluoromethyl)-1,2,4-oxadiazol-5-yl)pyridin-2-yl)piperidin-1-yl)-5H-pyrrolo[2,3-d]pyrimidin-6(7H)-one (Compound (44)).

More preferable examples of the compounds of the present invention include the following compounds:

4-(4-(5-((2-(tert-butylamino)ethyl)amino)-5'-fluoro-[2,3'-bipyridin]-6-yl)piperidin-1-yl)-5,5-dimethyl-5H-pyrrolo[2,3-d]pyrimidin-6(7H)-one (Compound (1));

4-(4-(2'-fluoro-5-((2-(pyrrolidin-1-yl)ethyl)amino)-[2,4'-bipyridin]-6-yl)piperidin-1-yl)-5-methyl-5H-pyrrolo[2,3-d]pyrimidin-6(7H)-one (Compound (13));

4-(4-(6-(furan-3-yl)-3-((2-(pyrrolidin-1-yl)ethyl)amino)pyridin-2-yl)piperidin-1-yl)-5-methyl-5H-pyrrolo[2,3-d]pyrimidin-6(7H)-one (Compound 14);

4-(4-(5-((2-(isopropylamino)ethyl)amino)-5'-methoxy-[2,3'-bipyridin]-6-yl)piperidin-1-yl)-5-methyl-5H-pyrrolo[2,3-d]pyrimidin-6(7H)-one (Compound (15));

4-(4-(6-(5-(difluoromethyl)-1,3,4-oxadiazol-2-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one (Compound (30));

4-(4-(3-((2-(tert-butylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (32));

4-(4-(3-((2-(tert-butylamino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one (Compound (41)); and 5,5-dimethyl-4-(4-(3-((2-(pyrrolidin-1-yl)ethyl)amino)-6-(3-(trifluoromethyl)-1,2,4-oxadiazol-5-yl)pyridin-2-yl)piperidin-1-yl)-5H-pyrrolo[2,3-d]pyrimidin-6(7H)-one (Compound (44)).

Particularly preferable examples of the compounds of the present invention include the following compounds from the viewpoint of oral absorption properties and the hERG test (cardiotoxicity):

4-(4-(6-(5-(difluoromethyl)-1,3,4-oxadiazol-2-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one (Compound (30));

4-(4-(3-((2-(tert-butylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (32)); and 4-(4-(3-((2-(tert-butylamino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one (Compound (41)).

Subsequently, the method for producing the compound of the present invention is described.

The compound represented by Formula (I) according to the present invention can be produced by, for example, the method of production described below or the method described in the examples. It should be noted that the method for producing the compound represented by Formula (I) according to the present invention is not limited to the reaction examples described herein. Products obtained in each step can be subjected to the subsequent steps with or without known means of separation and purification, such as concentration, vacuum concentration, crystallization, solvent extraction, reprecipitation, or chromatography.

Production Method 1

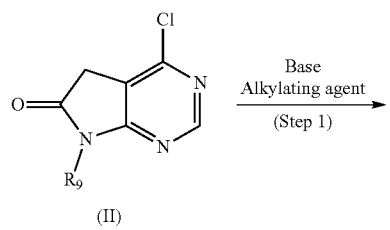

(II)

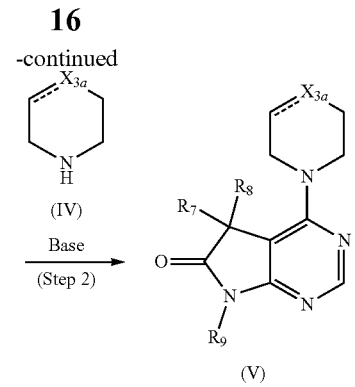

wherein $R_9$ represents a hydrogen atom or $PG_1$; $R_7$ and $R_8$ are as defined above; $X_{3a}$ represents $NPG_2$, NH, or $CHR_{10}$ when a broken line (-----) indicates a single bond, or $CR_{10}$ when a broken line indicates a double bond; $R_{10}$ represents $B(OR_{11})_2$, a hydroxyl group, a halogen group, or a substituent represented by Formula (VI)

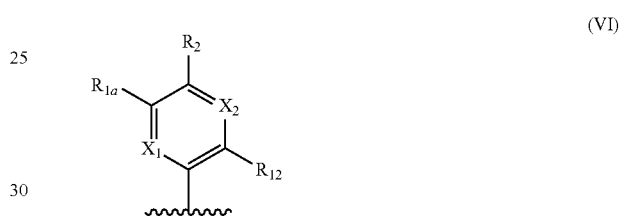

wherein $X_1$, $X_2$, and $R_2$ are as defined above; $R_{1a}$ represents a hydrogen atom, a halogen group, a cyano group, or $CO_2R_{11}$, or is as defined as $R_1$; $R_{12}$ represents an amino group, a 2-hydroxyethyl group, or a substituent represented by Formula (VII):

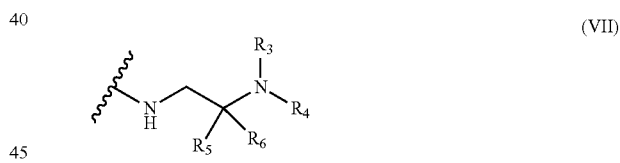

wherein $R_3$, $R_4$, $R_5$, and $R_6$ are as defined above; $R_{11}$ represents a hydrogen atom or an optionally substituted lower alkyl group (two $R_{11}$ substituents may form, together with oxygen atoms to which they are bound, a ring, which may comprise substituents; and $PG_1$ and $PG_2$ each represent a protective group.

(Step 1)

Step 1 comprises treating a compound represented by Formula (II) with a base and an alkylating agent to produce a compound represented by Formula (III) via an alkylation reaction.

Examples of bases used in this step include organic bases, such as triethylamine, diisopropylethylamine, pyridine, 4-dimethylaminopyridine, potassium-tert-butylate, sodium-tert-butylate, sodium methoxide, sodium ethoxide, lithium hexamethyl disilazide, sodium hexamethyl disilazide, potassium hexamethyl disilazide, lithium diisopropylamide, and butyllithium, and inorganic bases, such as sodium bicarbonate, sodium carbonate, potassium carbonate, cesium carbonate, sodium hydroxide, and sodium hydride.

An alkylating agent used in this step is not particularly limited, provided that $R_7$ and $R_8$ can be introduced. Examples thereof include iodomethane, iodoethane, 1,2-dibromoethane, 1,3-dibromopropane, and 1,4-dibromobutane.

In this step, copper (1) bromide or the like can be used as a catalyst.

This step is generally carried out with the use of a base in an amount of 0.5 to 5 moles, and preferably 1 to 2 moles, and an alkylating agent in an amount of 0.5 to 5 moles, and preferably 1 to 3 moles, relative to 1 mole of a compound represented by Formula (II).

A reaction solvent is not particularly limited, provided that the reaction is not adversely affected. Preferable examples thereof include isopropanol, tert-butyl alcohol, toluene, benzene, methylene chloride, chloroform, tetrahydrofuran, dioxane, N,N-dimethylformamide, N,N-dimethylacetamide, N-methylpyrrolidinone, dimethyl sulfoxide, and a mixture of any thereof.

A reaction temperature is generally −78° C. to a solvent reflux temperature, and preferably 0° C. to room temperature.

A reaction time is generally 10 minutes to 24 hours, and preferably 10 minutes to 1 hour.

(Step 2)

Step 2 comprises subjecting to a $S_NAr$ reaction between a compound represented by Formula (III) and a compound represented by Formula (IV) to produce a compound represented by Formula (V).

$PG_1$ and $PG_2$ are not particularly limited, provided that it is a common amino protective group. Preferable examples of $PG_1$ include 2,4,6-trimethoxybenzyl, 2,4-dimethoxybenzyl, and 4-methoxybenzyl groups, and preferable examples of $PG_2$ include tert-butoxycarbonyl, benzyloxycarbonyl, and 4-methoxybenzyl groups.

This step is generally carried out with the use of a compound represented by Formula (IV) in an amount of 0.5 to 5 moles, and preferably 1 to 2 moles, relative to 1 mole of a compound represented by Formula (III).

Examples of bases used in this step include organic bases, such as triethylamine, diisopropylethylamine, pyridine, lutidine, collidine, 4-dimethylaminopyridine, potassium-tert-butylate, sodium-tert-butylate, sodium methoxide, sodium ethoxide, lithium hexamethyl disilazide, sodium hexamethyl disilazide, potassium hexamethyl disilazide, and butyllithium, and inorganic bases, such as sodium bicarbonate, sodium carbonate, potassium carbonate, cesium carbonate, sodium hydroxide, sodium hydride, sodium phosphate, and potassium phosphate.

A reaction solvent is not particularly limited, provided that the reaction is not adversely affected. Preferable examples thereof include isopropanol, tert-butyl alcohol, toluene, benzene, methylene chloride, chloroform, tetrahydrofuran, dioxane, N,N-dimethylformamide, N,N-dimethylacetamide, N-methylpyrrolidinone, dimethyl sulfoxide, and a mixture of any thereof.

A reaction temperature is generally 0° C. to 200° C., and preferably 80° C. to 180° C.

A reaction time is generally 10 minutes to 3 days, and preferably 1 hour to 10 hours.

Production Method 2

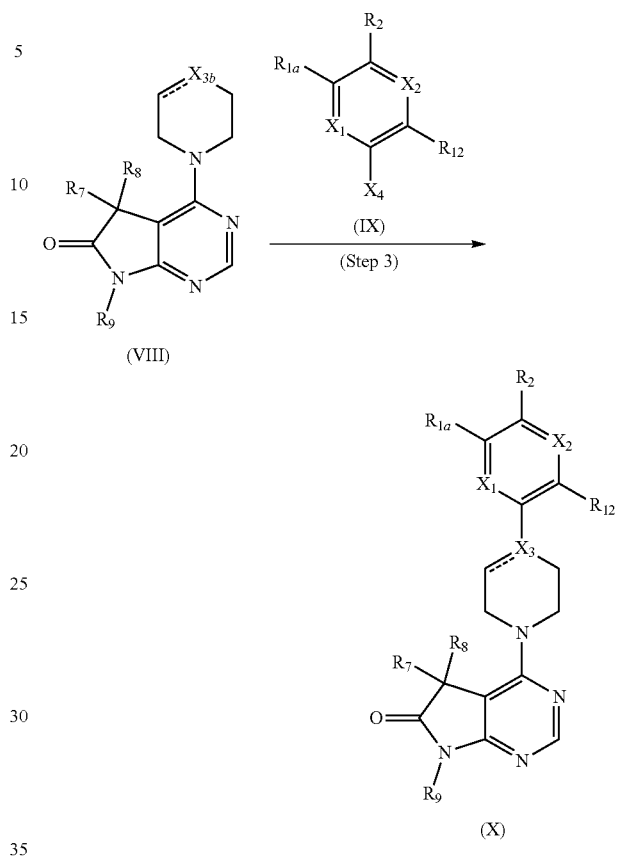

wherein $R_{1a}$, $R_2$, $R_7$, $R_8$, $R_9$, $R_{12}$, $X_1$, $X_2$, and $X_3$ are as defined above; $X_{3b}$ represents NH or $CHR_{10a}$ when a broken line ( ---- ) indicates a single bond, or $CR_{10a}$ when a broken line represents a double bond; $R_{10a}$ represents $B(OR_{11})_2$ or a halogen group: $X_4$ represents a hydrogen atom or a halogen group; and $R_{11}$ are as defined above.

(Step 3)

Step 3 comprises subjecting to a cross-coupling reaction of a compound represented by Formula (VIII) and a compound represented by Formula (IX) to produce a compound represented by Formula (X).

Step 3 can adopt, for example, known coupling reactions, such as the Suzuki coupling reaction, the Negishi coupling reaction, or the method of aromatic amine synthesis from an aryl halide and an amine in the presence of a palladium catalyst, which is reported by Buchwald and Hartwig et al.

This reaction can be carried out, for example, in the presence or absence of a palladium catalyst in an adequate solvent by heating at 20° C. to 200° C.

Examples of a palladium catalyst that can be used include palladium acetate, palladium chloride, tetrakis(triphenylphosphine)palladium, dichlorobis(triphenylphosphine) palladium, dichloro[1,1'-bis(diphenylphosphino)ferrocene]palladium, dichlorobisacetonitrile-palladium, and tris(dibenzylideneacetone)dipalladium (0).

An adequate amount of palladium catalysts that can be used is 0.001 to 1 mole, relative to 1 mole of a compound represented by Formula (VIII).

According to need, for example, 1-1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, or 2-di-tert-butylphosphino-3,4,5,6-tetramethyl-2',4',6'-tri-i-propylbiphenyl can be used as a palladium ligand.

A reaction solvent can be used without particular limitation, provided that it is not involved in the reaction. Examples thereof include an ether such as tetrahydrofuran and 1,4-dioxane, an alcohol such as methanol and ethanol, an amide such as N,N-dimethylformamide, N,N-dimethylacetamide, and N-methyl-2-pyrrolidone, a hydrocarbon such as benzene and toluene, acetonitrile, dimethyl sulfoxide, water, and a solvent mixture of any thereof.

Examples of bases that can be used in this step include organic bases, such as potassium-tert-butylate, sodium-tert-butylate, sodium methoxide, sodium ethoxide, lithium hexamethyl disilazide, sodium hexamethyl disilazide, potassium hexamethyl disilazide, and butyllithium, and inorganic bases, such as sodium carbonate, potassium carbonate, cesium carbonate, sodium hydroxide, sodium phosphate, and potassium phosphate.

While a reaction time varies depending on a type of a starting material used and a reaction temperature, in general, it is adequately within a range of 30 minutes to 24 hours.

Production Method 3

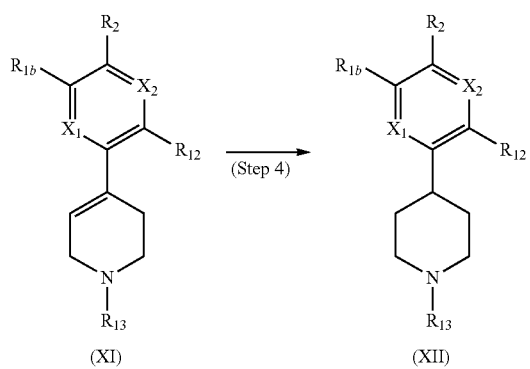

(XI)    (XII)

wherein $R_2$, $R_{12}$, $X_1$, and $X_2$ are as defined above; $R_{1b}$ represents a hydrogen atom, a cyano group, or $CO_2R_{11}$ or as defined with respect to $R_1$; $R_{13}$ represents $PG_2$ or a substituent represented by Formula (XIII):

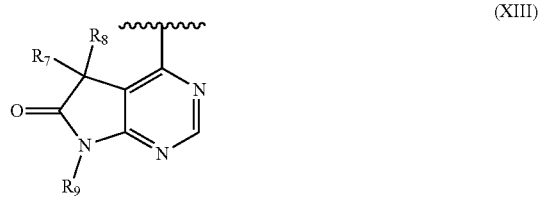

(XIII)

wherein $R_7$, $R_8$, and $R_9$ are as defined above; and $PG_2$ is as defined above.

(Step 4)

Step 4 comprises reducing a compound represented by Formula (XI) to produce a compound represented by Formula (XII).

Step 4 can be carried out, for example, in an adequate solvent that does not adversely affect the reaction, such as acetonitrile, ethyl acetate, THF, methanol, ethanol, DMF, DMA, or NMP with the use of a hydrogen source, such as hydrogen, formic acid, ammonium formate, or cyclohexadiene, and palladium/carbon or palladium hydroxide/carbon as a catalyst. Step 4 is generally carried out with the use of a catalyst in an amount of 0.01 to 5 moles, and preferably 0.05 to 1 mole, relative to 1 mole of a compound represented by Formula (XI). A reaction temperature is generally room temperature to a solvent reflux temperature. A reaction time is generally 1 hour to 24 hours.

Production Method 4

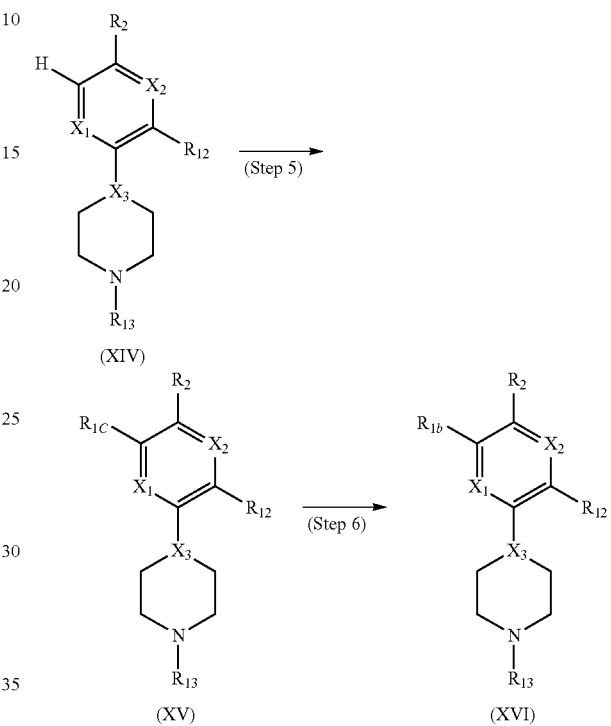

wherein $R_{1b}$, $R_2$, $R_{12}$, $R_{13}$, $X_1$, $X_2$, and $X_3$ are as defined above; and $R_{1C}$ represents a halogen group.

(Step 5)

Step 5 comprises halogenating a compound represented by Formula (XIV) to produce a compound represented by Formula (XV).

Step 5 can be carried out with the use of, for example, N-chlorosuccinimide, N-bromosuccinimide, N-iodosuccinimide, bromine, and iodine. Any solvent can be used without particular limitation, provided that it does not adversely affect the reaction. For example, Step 5 can be carried out in an adequate solvent that does not adversely affect the reaction, such as acetonitrile, ethyl acetate, THF, methanol, ethanol, DMF, DMA, or NMP. A reaction temperature is generally 0° C. to 100° C., and preferably room temperature to reflux temperature. A reaction time is generally 10 minutes to 3 days, and preferably 30 minutes to 24 hours.

(Step 6)

Step 6 comprises performing a cyanidation reaction between a compound represented by Formula (XV) and sodium cyanide, potassium cyanide, or the like, or a cross-coupling reaction between a compound represented by Formula (XV) and an organic boron reagent, an organic tin reagent, an organic zinc reagent, or the like, or an ester synthesis reaction via introduction of carbon monoxide to produce a compound represented by Formula (XVI). This reaction can be carried out, for example, in the presence or absence of a palladium catalyst in an adequate solvent by heating at 20° C. to 200° C. Examples of palladium catalysts that can be used include palladium acetate, palladium chloride, tetrakis(triphenylphosphine) palladium, dichlorobis (triphenylphosphine)palladium, dichloro[1,1'-bis(diphenylphosphino) ferrocene]palladium, dichlorobisacetonitrilepalladium, and tris(dibenzylideneacetone) dipalladium (0). An adequate amount of a palladium catalyst that can be used is 0.001 to 1 mole, relative to 1 mole of a compound represented by Formula (XV). According to need, for example, 1-1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexyl-phosphino-2',6'-dimethoxybiphenyl, or 2-di-tert-butylphosphino-3,4,5,6-tetramethyl-2',4',6'-tri-i-propyl-biphenyl can be used as a palladium ligand.

Examples of bases that can be used in Step 6 include organic bases, such as potassium-tert-butylate, sodium-tert-butylate, sodium methoxide, sodium ethoxide, lithium hexamethyl disilazide, sodium hexamethyl disilazide, potassium hexamethyl disilazide, and butyllithium, and inorganic bases, such as sodium carbonate, potassium carbonate, cesium carbonate, sodium hydroxide, sodium phosphate, and potassium phosphate.

Any reaction solvent can be used without particular limitation, provided that it is not involved in the reaction. Examples thereof include an ether, such as tetrahydrofuran and 1,4-dioxane, an alcohol, such as methanol and ethanol, an amide, such as N,N-dimethylformamide, N,N-dimethylacetamide, and N-methyl-2-pyrrolidone, a hydrocarbon, such as benzene and toluene, acetonitrile, dimethyl sulfoxide, water, and a mixed solvent of any thereof. A reaction time varies depending on a type of a starting material used and a reaction temperature. In general, an adequate time is within a range of 30 minutes to 24 hours.

Production Method 5

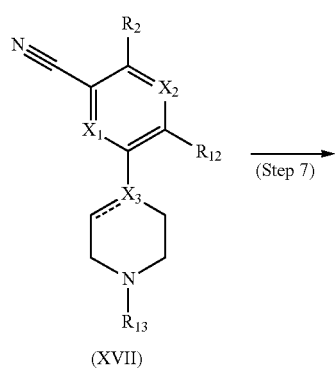

(XVII)

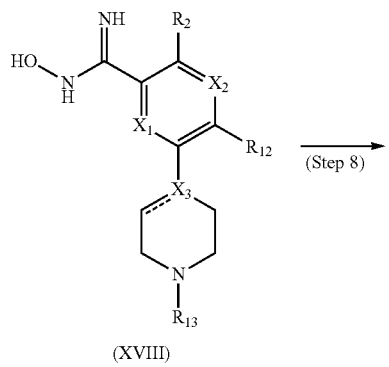

(XVIII)

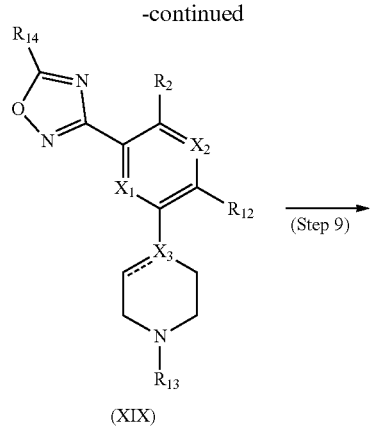

(XIX)

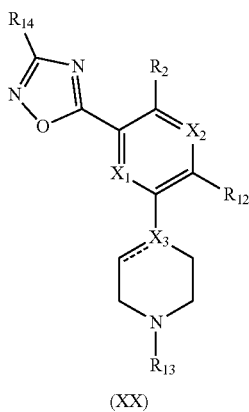

(XX)

In the formulae, $R_2$, $R_{12}$, $R_{13}$, $X_1$, $X_2$, and $X_3$ are as defined above; and $R_{14}$ represents a hydrogen atom, an optionally substituted alkyl group, or an optionally substituted cycloalkyl group.

(Step 7)

Step 7 comprises subjecting to a reaction of a compound represented by Formula (XVII) and hydroxyamine to produce a compound represented by Formula (XVIII). Hydroxylamine can be used as an aqueous solution or a salt with hydrochloric acid or the like, and, according to need, in combination with a base. Examples of bases include organic bases, such as triethylamine and diisopropylethylamine, and inorganic bases, such as sodium carbonate and potassium phosphate. A reaction solvent is not particularly limited, provided that it does not adversely affect the reaction. Preferable examples thereof include methanol, ethanol, propanol, isopropanol, tert-butyl alcohol, toluene, benzene, methylene chloride, chloroform, tetrahydrofuran, 1,4-dioxane, N,N-dimethylformamide, N,N-dimethylacetamide, N-methylpyrrolidinone, dimethyl sulfoxide, and a mixed solvent of any thereof. A reaction temperature is generally 0° C. to solvent reflux temperature, and preferably room temperature to solvent reflux temperature. A reaction time is generally 10 minutes to 24 hours, and preferably 10 minutes to 1 hour.

(Step 8)

Step 8 comprises subjecting to acylation and cyclization of a compound represented by Formula (XVIII) to produce a compound represented by Formula (XIX). As an acylation agent, carboxylic anhydride, mixed acid anhydride, acid chloride, or carboxylic acid having $R_{14}$ can be used. The subsequent cyclization reaction can be carried out with the use of an excess amount of the acylation agent or with the use of a dehydration-condensation agent, such as triphenylphosphine-carbon tetrabromide, phosphoryl chloride, propylphosphonic anhydride (cyclic trimer), or dicyclohexylcarbodiimide. A reaction solvent is not particularly limited, provided that it does not adversely affect the reaction. Preferable examples thereof include toluene, benzene, methylene chloride, chloroform, tetrahydrofuran, 1,4-dioxane, N,N-dimethylformamide, N,N-dimethylacetamide, N-methylpyrrolidinone, and a mixed solvent of any thereof. A reaction temperature is generally 0° C. to solvent reflux temperature, and preferably room temperature to solvent reflux temperature. A reaction time is generally 10 minutes to 24 hours, and preferably 10 minutes to 1 hour.

(Step 9)

Step 9 comprises subjecting to an isomerization reaction of a compound represented by Formula (XIX) to produce a compound represented by Formula (XX). This step can be carried out by, for example, allowing hydroxyamine to act on the compound represented by Formula (XIX) in a reaction solvent, such as toluene, benzene, methylene chloride, chloroform, tetrahydrofuran, 1,4-dioxane, N,N-dimethylformamide, N,N-dimethylacetamide, N-methylpyrrolidinone, or a mixed solvent of any thereof. A reaction solvent is not particularly limited, provided that it does not adversely affect the reaction. A reaction temperature is generally 0° C. to solvent reflux temperature, and preferably room temperature to solvent reflux temperature. A reaction time is generally 10 minutes to 24 hours, and preferably 10 minutes to 1 hour.

Production Method 6

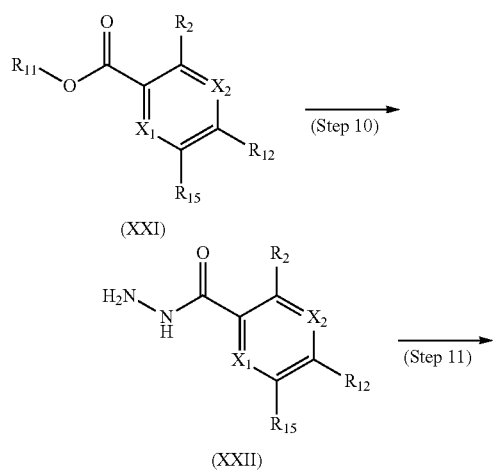

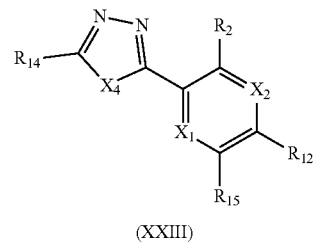

(XXIII)

In the formulae, $R_2$, $R_{11}$, $R_{12}$, $R_{14}$, $X_1$, and $X_2$ are as defined above; $X_4$ represents an oxygen atom or a sulfur atom; and $R_{15}$ represents a hydrogen atom, a halogen group, or a substituent represented by Formula (XXIV):

(XXIV)

wherein $X_3$ and $R_{13}$ are as defined above.

(Step 10)

Step 10 comprises producing a compound represented by Formula (XXII) from a compound represented by Formula (XXI) and hydrazine. Hydrazine can be used in the form of a hydrate thereof or a salt with hydrochloric acid or the like. When a carboxylic acid is used as a starting material, a dehydration-condensation agent, such as carbonyldiimidazole, phosphoryl chloride, propylphosphonic anhydride (cyclic trimer), or dicyclohexylcarbodiimide, can be used as an activation agent. A reaction solvent is not particularly limited, provided that it does not adversely affect the reaction. Preferable examples thereof include ethanol, propanol, toluene, benzene, tetrahydrofuran, 1,4-dioxane, N,N-dimethylformamide, N,N-dimethylacetamide, N-methylpyrrolidinone, dimethyl sulfoxide, and a mixed solvent of any thereof. A reaction temperature is generally 0° C. to solvent reflux temperature, and preferably room temperature to solvent reflux temperature. A reaction time is generally 10 minutes to 24 hours, and preferably 30 minutes to 12 hours.

(Step 11)

Step 11 comprises subjecting to acylation and cyclization of a compound represented by Formula (XXII) to produce a compound represented by Formula (XXIII). Step 11 can be carried out in the same manner as with Step 8.

Production Method 7

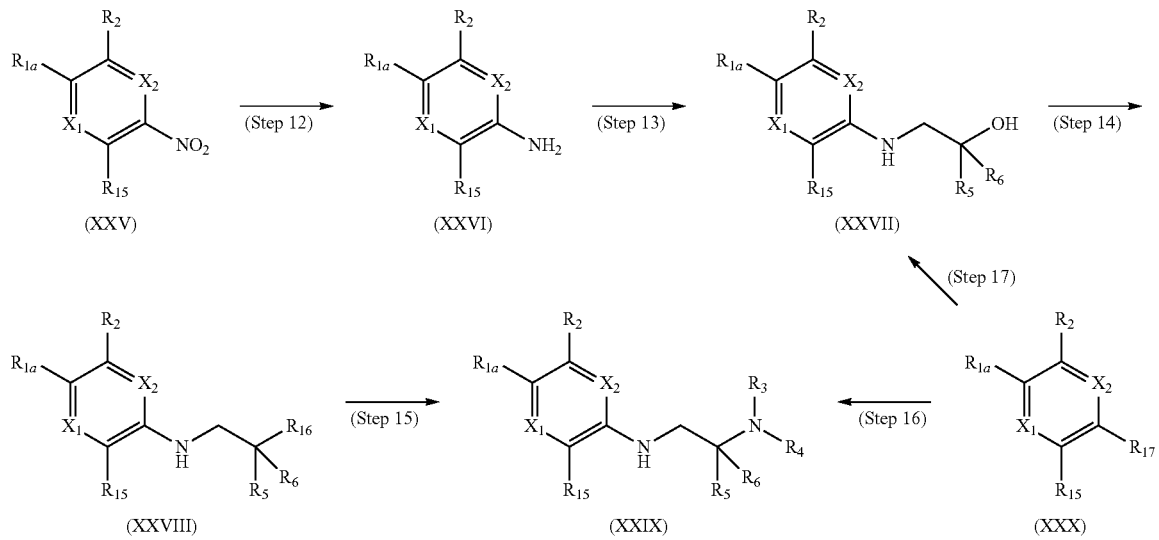

In the formulae, $R_{1a}$, $R_2$, $R_3$, $R_4$, $R_5$, $R_6$, $R_{15}$, $X_1$, and $X_2$ are as defined above; $R_{16}$ represents a leaving group, such as a halogen group, a tosyl group, a mesyl group, or a trifluoromethanesulfonyl group; and $R_{17}$ represents a halogen group.

(Step 12)

Step 12 comprises reducing a nitro group of a compound represented by Formula (XXV) to produce a compound represented by Formula (XXVI). Step 12 can be carried out via a hydrogenation reaction involving the use of a catalyst such as palladium on carbon or a reaction involving the use of a metal such as iron and zinc and tin (II) chloride as a reducing agent. A reaction solvent is not particularly limited, provided that it does not adversely affect the reaction. Preferable examples thereof include methanol, ethanol, propanol, tetrahydrofuran, 1,4-dioxane, N,N-dimethylformamide, N,N-dimethylacetamide, N-methylpyrrolidinone, dimethyl sulfoxide, and a mixed solvent of any thereof. A reaction temperature is generally 0° C. to solvent reflux temperature, and preferably room temperature to solvent reflux temperature. A reaction time is generally 10 minutes to 24 hours, and preferably 30 minutes to 12 hours.

(Step 13)

Step 13 comprises subjecting to a reductive amination reaction of a compound represented by Formula (XXVI) and an aldehyde or an equivalent thereof to produce a compound represented by Formula (XXVII). Examples of an aldehyde or an equivalent thereof that can be used in Step 13 include 1,4-dioxane-2,5-diol and 2-hydroxyacetaldehyde. Examples of reducing agents that can be used include sodium borohydride, sodium cyanoborohydride, and sodium triacetoxyborohydride. A reaction solvent is not particularly limited, provided that it does not adversely affect the reaction. Preferable examples include methanol, ethanol, propanol, toluene, benzene, tetrahydrofuran, 1,4-dioxane, N,N-dimethylformamide, N,N-dimethylacetamide, N-methylpyrrolidinone, dimethyl sulfoxide, and a mixed solvent of any thereof. A reaction temperature is generally 0° C. to solvent reflux temperature, and preferably room temperature to solvent reflux temperature. A reaction time is generally 10 minutes to 24 hours, and preferably 30 minutes to 12 hours.

(Step 14)

Step 14 comprises converting a hydroxyl group of a compound represented by Formula (XXVII) into a leaving group such as a halogen group or methanesulfonyl group to produce a compound represented by Formula (XXVIII). For example, sulfonyl esterification may be carried out with the use of methanesulfonyl chloride or toluenesulfonyl chloride in combination with an adequate base. Halogenation can be carried out with the use of a halogenation agent such as carbon tetrachloride, carbon tetrabromide, or iodine in combination with triphenylphosphine. Alternatively, halogenation can be carried out by treating the sulfonylester with halogenated lithium or the like to convert the sulfonylester into a halogen group.

A compound represented by Formula (XXVIII) can also be synthesized from a compound represented by Formula (XXVI) via a direct reductive amination or other means. In such a case, for example, 2-chloroacetaldehyde or 2-bromoacetaldehyde can be used as an aldehyde, and a compound represented by Formula (XXVIII) can be synthesized in the same manner as in Step 13.

(Step 15)

Step 15 comprises subjecting to a reaction of a compound represented by Formula (XXVIII) and amine represented by $HNR_3R_4$ to produce a compound represented by Formula (XXIX). Step 15 can be carried out with the use of an excess amount of amine represented by $HNR_3R_4$ or by allowing amine represented by $HNR_3R_4$ to react with a compound represented by Formula (XXVIII) in the presence of an adequate base. Step 15 can be carried out without the use of a solvent. When a solvent is used, for example, use of ethanol, propanol, toluene, benzene, tetrahydrofuran, 1,4-dioxane, N,N-dimethylformamide, N,N-dimethylacetamide, N-methylpyrrolidinone, dimethyl sulfoxide, or a mixed solvent of any thereof is preferable. A reaction temperature is generally 0° C. to solvent reflux temperature, and preferably room temperature to solvent reflux temperature. A reaction time is generally 10 minutes to 24 hours, and preferably 30 minutes to 12 hours.

(Step 16)

Step 16 comprises subjecting to a reaction of a compound represented by Formula (XXX) and amine represented by Formula (XXXI):

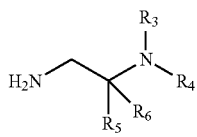

(XXXI)

wherein $R_3$, $R_4$, $R_5$, and $R_6$ are as defined above, to produce a compound represented by Formula (XXIX). Step 16 can be carried out with the use of an excess amount of amine represented by Formula (XXXI) or with the use of an amine represented by Formula (XXXI) in combination with an adequate base. This reaction can involve the use of a palladium or copper catalyst. Examples of palladium catalysts include palladium acetate, palladium chloride, tetrakis(triphenylphosphine)palladium, dichlorobis(triphenylphosphine)palladium, dichloro[1,1'-bis(diphenylphosphino)ferrocene]palladium, dichlorobisacetonitrilepalladium, and tris(dibenzylideneacetone)dipalladium (0).

An adequate amount of a palladium catalyst that can be used is 0.001 to 1 mole, relative to 1 mole of a compound represented by Formula (XXX).

According to need, for example, 1-1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, or 2-di-tert-butylphosphino-3,4,5,6-tetramethyl-2',4',6'-tri-i-propylbiphenyl can be used as a palladium ligand.

Examples of bases that can be used in Step 16 include organic bases, such as triethylamine, diisopropylethylamine, potassium-tert-butylate, sodium-tert-butylate, sodium methoxide, sodium ethoxide, lithium hexamethyl disilazide, sodium hexamethyl disilazide, and potassium hexamethyl disilazide, and inorganic bases, such as sodium carbonate, potassium carbonate, cesium carbonate, sodium hydroxide, sodium phosphate, and potassium phosphate. Preferable examples of reaction solvents include ethanol, propanol, toluene, benzene, tetrahydrofuran, 1,4-dioxane, N,N-dimethylformamide, N,N-dimethylacetamide, N-methylpyrrolidinone, dimethyl sulfoxide, and a mixed solvent of any thereof. A reaction temperature is generally 0° C. to solvent reflux temperature, and preferably room temperature to solvent reflux temperature. A reaction time is generally 10 minutes to 24 hours, and preferably 30 minutes to 12 hours. (Step 17)

Step 17 comprises subjecting to a reaction of a compound represented by Formula (XXX) and an amine represented by Formula (XXXII):

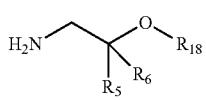

(XXXII)

wherein $R_5$ and $R_6$ are as defined above; and $R_{18}$ represents a protective group or a hydrogen atom, to produce a compound represented by Formula (XXVII). Step 17 can be carried out in the same manner as in Step 16.

The compound or the salt thereof according to the present invention may be amorphous or crystalline. Compounds of a single crystalline form or a mixture of many crystalline forms are within the scope of the compound or the salt thereof according to the present invention. Crystals can be produced with the application of known crystallization techniques. The compound or the salt thereof according to the present invention may be in the form of a solvate (e.g., a hydrate) or a non-solvate. Compounds labeled with isotope ligands (e.g., $^3H$, $^{14}C$, $^{35}S$, or $^{125}I$) are within the scope of the compound or the salt thereof according to the present invention.

The salt of the compound according to the present invention means a pharmaceutically acceptable salt.

The compound or the salt thereof according to the present invention also encompasses a prodrug thereof. The term "prodrug" refers to a compound that is converted into the compound or the salt thereof according to the present invention via a reaction mediated by an enzyme, gastric acid, or the like under physiological conditions in vivo; i.e., a compound that enzymatically causes oxidation, reduction, hydrolysis, or other reactions and is then converted into the compound or the salt thereof according to the present invention, or a compound that causes hydrolysis or other reactions with the aid of gastric acid or the like and is then converted into the compound or the salt thereof according to the present invention. Alternatively, a prodrug may be a compound that is converted into the compound or the salt thereof according to the present invention under physiological conditions as described in "Iyakuhin no Kaihatsu (Pharmaceutical Research and Development)," Hirokawa Publishing Company, 1990, vol. 7, Bunshi Sekkei (Drug Design), p. 163-198.

According to an embodiment, the compound or the salt thereof according to the present invention has an excellent inhibitory activity against Akt. The term "Akt" used herein encompasses Akt of a human or non-human mammalian, with human Akt being preferable. The term "Akt" also encompasses a plurality of isoforms. In the case of human Akt, for example, Akt1, Akt2, and Akt3 are within the scope thereof. According to an embodiment, the compound or the salt thereof according to the present invention has an inhibitory activity against at least one type, preferably two or more types, more preferably three or more types, and further preferably all types of such isoforms. Specifically, Akt1 or Akt2 is preferable, and Akt1 is more preferable. An inhibitory activity of the compound according to the present invention on Akt can be assayed by a conventional technique known in the art (Biochem. J. vol. 385, pp. 399-408, 2005, and Cancer Res., vol. 68, pp. 2366-2374, 2008).

According to an embodiment, the compound or the salt thereof according to the present invention has an excellent inhibitory activity against Rsk. The term "Rsk" used herein encompasses Rsk of a human or non-human mammalian, with human Rsk being preferable. The term "Rsk" also encompasses a plurality of isoforms. In the case of human Rsk, for example, Rsk1 (RPS6KA1), Rsk2 (RPS6KA3), Rsk3 (RPS6KA2), and Rsk4 (RPS6KA6) are within the scope thereof. According to an embodiment, the compound or the salt thereof according to the present invention has an inhibitory activity against at least one type, preferably two or more types, more preferably three or more types, and further preferably all types of such isoforms. Specifically, Rsk1 is preferable. An inhibitory activity of the compound according to the present invention on Rsk can be assayed by a conventional technique known in the art (Biol. Pharm. Bull., vol. 39. pp. 547-555, 2016).

According to an embodiment, the compound or the salt thereof according to the present invention has an excellent inhibitory activity against S6K. The term "S6K" used herein encompasses S6K of a human or non-human mammalian, with human S6K being preferable. The term "S6K" also encompasses a plurality of isoforms. In the case of human S6K, for example, S6K1 (RPS6KB1) and S6K2 (RPS6KB2) are within the scope thereof. According to an embodiment, the compound or the salt thereof according to the present invention has an inhibitory activity against at least one type, and preferably all types of such isoforms. Specifically, S6K1 is preferable. An inhibitory activity of the compound according to the present invention on S6K can be assayed by a conventional technique known in the art (J. Biol. Chem., vol. 285, pp. 4587-4594, 2010).

According to an embodiment, the compound or the salt thereof according to the present invention has an excellent inhibitory activity against Akt. Thus, it is useful as a medicine for the prevention or treatment of a disease associated with Akt. The term "disease associated with Akt" refers to a disease that can achieve a decreased incidence, remission and relief of symptoms, and/or full recovery as a result of deletion, suppression, and/or inhibition of Akt functions.

According to an embodiment, the compound or the salt thereof according to the present invention has an excellent inhibitory activity against Rsk. Thus, it is useful as a medicine for the prevention or treatment of a disease associated with Rsk. The term "disease associated with Rsk" refers to a disease that can achieve a decreased incidence, remission and relief of symptoms, and/or full recovery as a result of deletion, suppression, and/or inhibition of Rsk functions.

According to an embodiment, the compound or the salt thereof according to the present invention has an excellent inhibitory activity against S6K. Thus, it is useful as a medicine for the prevention or treatment of a disease associated with S6K. The term "disease associated with S6K" refers to a disease that can achieve a decreased incidence, remission and relief of symptoms, and/or full recovery as a result of deletion, suppression, and/or inhibition of S6K functions.

Examples of "diseases associated with Akt," "diseases associated with Rsk," and "diseases associated with S6K" include, but are not limited to, cancer, autoimmune diseases, and macroglobulinemia. Tumors targeted by the present invention are not particularly limited. Examples thereof include head and neck cancer, digestive system cancers (e.g., esophageal cancer, gastric cancer, duodenal carcinoma, liver cancer, biliary tract cancer including gallbladder cancer and bile duct adenocarcinoma, pancreatic cancer, and large bowel cancer including colorectal cancer, colonic cancer, and rectal cancer), lung cancer (e.g., non-small cell lung cancer, small cell lung cancer, and mesothelial tumor), breast cancer, genital cancer (e.g., ovarian cancer and uterine cancer including cervix cancer and endometrial cancer), urologic cancer (e.g., renal cancer, bladder cancer, prostate cancer, and testicular tumor), hematopoietic tumors (e.g., leukemia, malignant lymphoma, and multiple myeloma), bone and soft tissue tumors, skin cancer, and brain tumor. Tumors targeted by the present invention are preferably digestive system cancers and genital cancer, and more preferably large bowel cancer and endometrial cancer.

According to an embodiment, the compound or the salt thereof according to the present invention simultaneously inhibits at least two kinases selected from the group consisting of Akt, Rsk, and S6K. For example, the compound or the salt thereof according to the present invention simultaneously inhibits Akt and Rsk. For example, the compound or the salt thereof according to the present invention simultaneously inhibits Akt and S6K. For example, the compound or the salt thereof according to the present invention simultaneously inhibits Rsk and S6K. For example, the compound or the salt thereof according to the present invention simultaneously inhibits Akt, Rsk, and S6K. By simultaneously inhibiting at least two kinases selected from the group consisting of Akt, Rsk, and S6K with the use of a single compound, side effects can be reduced and synergistic therapeutic effects can be attained more efficiently, compared with the case in which such kinases are simultaneously inhibited with the use of a plurality of compounds.

When the compound or the salt thereof according to the present invention is to be used as a medicine, a pharmaceutical carrier is incorporated according to need, and any dosage form may be adopted in accordance with preventive or therapeutic effects of interest. Any of dosage forms, such as an oral preparation, injection preparation, suppository, ointment, inhalant, adhesive skin patch, and the like may be adopted, with an oral preparation being preferable. Such dosage forms can be prepared in accordance with conventional techniques known to a person skilled in the art.

As a pharmaceutically acceptable carrier, various types of organic or inorganic carriers that are commonly used for pharmaceutical preparations are used. A pharmaceutically acceptable carrier is incorporated into a medicine in the form of, for example, an excipient, a binder, a disintegrator, a lubricant, or a colorant in a solid preparation or a solvent, a solubilizer, a suspension agent, an isotonizing agent, a buffer, or a soothing agent in a liquid preparation. According to need, an additive, such as an antipreservative, an antioxidant, a colorant, a sweetening agent, a stabilizer, or the like, can be used.

When preparing solid preparations for oral administration, an excipient and, according to need, a binder, a disintegrator, a lubricant, a colorant, a flavoring agent, and the like are added to the compound according to the present invention. Thereafter, tablets, coated tablets, granules, powders, capsules, and the like can be prepared in accordance with conventional techniques.

When preparing injection preparations, a pH modifier, a buffer, a stabilizer, an isotonizing agent, a local anesthetic, and the like are added to the compound according to the present invention. Thus, injection preparations for subcutaneous, intramuscular, and intravenous administration can be prepared in accordance with conventional techniques.

The amount of the compound according to the present invention to be incorporated into the dosage unit form varies depending on, for example, the symptom of a patient to which the compound is to be administered or a dosage form thereof. In general, the amount thereof is about 0.05 to 1,000 mg in the case of an oral preparation, it is about 0.01 to 500 mg in the case of an injection preparation, and it is about 1 to 1,000 mg in the case of a suppository per dosage unit form.

A dose of the medicine having the dosage form described above per day varies depending on, for example, the symptom, the body weight, the age, the sex, and other conditions of the patient. Accordingly, such dose cannot be collectively determined. The amount of the compound according to the present invention may generally be about 0.05 to 5,000 mg, and preferably 0.1 to 1,000 mg per day per adult (body weight: 50 kg). The compound in such amount is preferably administered once or 2 or 3 separate times a day.

EXAMPLES

Hereafter, the present invention is described in greater detail with reference to the examples and the test examples, although the present invention is not limited to these examples.

In the examples, commercially available reagents were used unless otherwise specified. Silica gel column chromatography and basic silica gel column chromatography were carried out with the use of prepacked columns manufactured by SHOKO Science Co., Ltd. or Biotage AB. NMR spectra were measured with the use of a spectrometer AL 400 (400 MHz; JEOL) or Mercury 400 (400 MHz; Varian). When a deuterated solvent contains tetramethylsilane, measurements were carried out with the use of tetramethylsilane as an internal standard. On other occasions, NMR solvents were used as an internal standard. All δ values were indicated in terms of ppm. Microwave reactions were carried out with the use of Initiator® manufactured by Biotage AB.

LCMS spectra were measured with the use of SQD manufactured by Waters under the conditions described below.
Column: Acquity BEH C18, 2.1×50 mm, 1.7 μm
MS detection: ESI positive
UV detection: 254 and 210 nm
Column flow rate: 0.5 ml/min
Mobile phase: Water/acetonitrile (0.1% formic acid)
Amount of injection: 1 μl
Gradient

| Time (min) | Water | Acetonitrile |
|---|---|---|
| 0 | 95 | 5 |
| 0.1 | 95 | 5 |
| 2.1 | 5 | 95 |
| 3.0 | Terminated | |

Abbreviations are as defined below.
s: Singlet
d: Doublet
t: Triplet
q: Quartette
dd: Double doublet
dt: Double triplet
ddd: Double double doublet
m: Multiplet
br: Broad
DMSO-$D_6$: Deuterated dimethyl sulfoxide
$CDCl_3$: Deuterated chloroform
THF: Tetrahydrofuran
DMF: N,N-Dimethylformamide
DMSO: Dimethyl sulfoxide
DIPEA: N,N-Diisopropylethylamine
HATU: O-(7-Azabenzotriazol-1-yl)-N,N,N',N'-tetramethyl uronium hexafluorophosphate
NBS: N-bromosuccinimide
TFA: Trifluoroacetic acid Reference Example 1: 4-Chloro-7-(2,4-dimethoxybenzyl)-5,5-dimethyl-5H-pyrrolo[2,3-d]pyrimidin-6(7H)-one (Reference Example (1))

To a mixture of 4-chloro-7-(2,4-dimethoxybenzyl)-5H-pyrrolo[2,3-d]pyrimidin-6(7H)-one (6 g), THF (93.8 ml), and tert-butoxypotassium (6.32 g), methyl iodide (3.51 ml) was slowly added dropwise, and the resulting mixture was then stirred at room temperature for 2 hours. Saturated aqueous ammonium chloride was added to the reaction mixture, and the mixture was then extracted with chloroform. The organic layer was dried over anhydrous sodium sulfate, filtered, and then concentrated. The resulting residue was purified via silica gel column chromatography to obtain the title compound as a white solid (Reference Example (1)).

Reference Example 2: 4-Chloro-7-(2,4-dimethoxybenzyl)-5-methyl-5H-pyrrolo[2,3-d]pyrimidin-6(7H)-one (Reference Example (2))

Step 1:
A mixture of triethyl propane-1,1,2-tricarboxylate (3.0 g) synthesized by the method described in Pierik, Antonio J.; Ciceri, Daniele; Broeker, Gerd; Edwards, Christopher H.; McFarlane, William; Winter, Joachim; Buckel, Wolfgang; Golding, Bernard T.; Journal of the American Chemical Society, 124 (47), 14039-14048; 2002, methanol (7.0 ml), and sodium methoxide (25%, methanol solution, 0.050 ml) was stirred at room temperature for 3 hours. After the reaction mixture was concentrated under a reduced pressure, sodium methoxide (25%, methanol solution, 5.3 g), methanol (2 ml), and formamidine acetate (1.3 g) were added thereto, and the mixture was stirred at room temperature for 15 hours. Hydrogen chloride (5-10%, methanol solution, 19 ml) was added to the reaction mixture, and the mixture was stirred at 0° C. for 15 minutes. The resulting solid was collected by filtration, washed with methanol, and dried under a reduced pressure. Thus, methyl 2-(4,6-dihydroxypyrimidin-5-yl)propionate was obtained as a white solid (Reference Example (2-1)).

Step 2:
A mixture of Reference Example (2-1) (1.2 g), phosphorus oxychloride (3.5 ml), and N,N-diethylaniline (4.0 ml) was stirred at 130° C. for 3 hours. The resulting mixture was cooled to room temperature, diluted with toluene (40 ml), and poured into ice water. The organic layer was separated, dried over anhydrous sodium sulfate, filtered, and then concentrated. The resulting residue was purified via silica gel column chromatography to obtain methyl 2-(4,6-dichloropyrimidin-5-yl)propionate as a brown solid (Reference Example (2-2)).

Step 3:
A mixture of Reference Example (2-2) (0.50 g), 2,4-dimethoxybenzylamine (0.35 ml), DIPEA (0.44 ml), and DMF (5 ml) was stirred at 60° C. for 2.5 hours. The reaction mixture was cooled to room temperature, diluted with ethyl acetate, and successively washed with water, 1N hydrochloric acid, water, and saturated saline in that order. The organic layer was dried over anhydrous sodium sulfate, filtered, and then concentrated. The resulting residue was dissolved in toluene (10 ml), p-toluenesulfonic acid hydrate (20 mg) was added thereto, and then heated under reflux for 2.5 hours. The reaction mixture was cooled to room temperature, diluted with ethyl acetate, and successively washed with water and saturated aqueous sodium bicarbonate in that order. The organic layer was dried over anhydrous sodium sulfate, filtered, and then concentrated. Ethyl acetate was added to the resulting residue and the mixture was stirred at room temperature. The resulting solid was collected by filtration to obtain the title compound as a white solid (Reference Example (2)).

Reference Example 3: 7-(2,4-Dimethoxybenzyl)-5-methyl-4-(4-(4,4,5,5-tetramethyl-1,3,2-dioxaborolan-2-yl)-5,6-dihydropyridin-1(2H)-yl)-5H-pyrrolo[2,3-d]pyrimidin-6(7H)-one (Reference Example (3))

Tert-butyl 4-(4,4,5,5-tetramethyl-1,3,2-dioxaborolan-2-yl)-5,6-dihydropyridin-1(2H)-carboxylate (1.0 g) was dissolved in dichloromethane (2.0 ml) and TFA (2.0 ml), and the solution was stirred at room temperature for 15 minutes. The reaction mixture was concentrated and dried. To the resulting residue, Reference Example (2) (1.1 g), DMSO (7.0 ml), and DIPEA (2.3 ml) were added, and then stirred at 120° C. for 4 hours under microwave irradiation. The mixture was cooled to room temperature, water was added thereto, and the mixture was then extracted with ethyl acetate. The organic layer was dried over anhydrous sodium sulfate, filtered, and then concentrated. The resulting residue was purified via silica gel column chromatography to obtain the title compound as a white amorphous substance (Reference Example (3)).

Reference Example 4: 7-(2,4-Dimethoxybenzyl)-4-(4-iodopiperidine-1-yl)-5,5-dimethyl-5H-pyrrolo[2,3-d]pyrimidin-6(7H)-one (Reference Example (4))

Step 1:
A mixture of Reference Example (1) (6.22 g), DIPEA (6.23 ml), 4-hydroxypiperidine (1.99 g), and DMSO (24 ml) was stirred at 130° C. for 3 hours under microwave irradiation. The reaction mixture was diluted with ethyl acetate and then washed with water. The organic layer was dried over anhydrous sodium sulfate, filtered, and then concentrated. The resulting residue was purified via silica gel column chromatography to obtain 7-(2,4-dimethoxybenzyl)-4-(4-hydroxypiperidin-1-yl)-5,5-dimethyl-5H-pyrrolo[2,3-d]pyrimidin-6(7H)-one as a yellow solid (Reference Example (4-1)).
Step 2:
To a mixture of Reference Example (4-1) (7.14 g) and THF (89.4 ml), iodine (6.81 g), triphenylphosphine (7.04 g), and imidazole (1.83 g) were added at 0° C., temperature was raised to room temperature, and the mixture was stirred for 1 hour. Saturated aqueous sodium thiosulfate was added to the reaction mixture and the resultant was extracted with ethyl acetate. The organic layer was dried over anhydrous sodium sulfate, filtered, and then concentrated. The resulting residue was purified via silica gel column chromatography and then recrystallized with methanol (80 ml). The resulting solid was collected by filtration and dried to obtain the title compound as white powder (Reference Example (4)).

Reference Example 5: 5,5-Dimethyl-4-(4-(4,4,5,5-tetramethyl-1,3,2-dioxaborolan-2-yl)-5,6-dihydropyridin-1(2H)-yl)-5H-pyrrolo[2,3-d]pyrimidin-6(7H)-one (Reference Example (5))

A mixture of tert-butyl 4-(4,5,5-tetramethyl-1,3,2-dioxaborolan-2-yl)-1,2,3,6-tetrahydropyridine-1-carboxylate (2.25 g), hydrogen chloride (1,4-dioxane solution, 4 M, 6 ml), and chloroform (3 ml) was stirred at room temperature for 3 hours. The reaction mixture was concentrated, 4-chloro-5,5-dimethyl-5H-pyrrolo[2,3-d]pyrimidin-6(7H)-one (1.31 g) synthesized by the method described in Shepherd, Timothy Alan; Dally, Robert Dean; Joseph, Sajan; US 2010/0120801A1, DIPEA (4.62 ml), and DMSO (10 ml) were added to the resulting residue, and the resulting mixture was agitated at 140° C. overnight. Water was added to the reaction mixture, and the mixture was then extracted with ethyl acetate. The organic layer was dried over anhydrous sodium sulfate, filtered, and then concentrated. The resulting residue was purified via silica gel column chromatography to obtain the title compound as a pale yellow amorphous substance (Reference Example (5)).

Example 1: 4-(4-(5-((2-(Tert-butylamino)ethyl)amino)-5'-fluoro-[2,3'-bipyridin]-6-yl)piperidin-1-yl)-5,5-dimethyl-5H-pyrrolo[2,3-d]pyrimidin-6(7H)-one (Compound (1))

Step 1:
A mixture of 3-amino-2-bromopyridine (4.0 g), tert-butyl 4-(4,4,5,5-tetramethyl-1,3,2-dioxaborolan-2-yl)-1,2,3,6-tetrahydropyridine-1-carboxylate (9.0 g), 1,1'-bis(diphenylphosphino)ferrocene-palladium (11) dichloride-dichloromethane complex (1.9 g), 1,4-dioxane (25 ml), and aqueous sodium carbonate (2 M, 15 ml) was stirred at 100° C. for 3 hours. The mixture was cooled to room temperature, diluted with water, and then extracted with ethyl acetate. The organic layer was dried over anhydrous sodium sulfate, filtered, and then concentrated. The resulting residue was purified via basic silica gel column chromatography to obtain tert-butyl 3-amino-5',6'-dihydro-[2,4'-bipyridine]-1'(2'H)-carboxylate as a brown oil substance (Compound (1-1)).
Step 2:
A mixture of Compound (1-1) (9.0 g), ethyl acetate (80 ml), and 10% palladium on carbon (2.5 g) was stirred in a hydrogen atmosphere at room temperature for 14 hours. After nitrogen substitution, the reaction mixture was filtered. The filtrate was concentrated to obtain tert-butyl 4-(3-aminopyridin-2-yl)piperidin-1-carboxylate (Compound (1-2)) as a brown amorphous substance.
Step 3:
To a mixture of Compound (1-2) (7.5 g), THF (60 ml), and a glycolaldehyde dimer (4.2 g), a solution of 0.5 M sodium cyanoborohydride-0.25 M zinc chloride in methanol (30 ml) was added with stirring. After the reaction mixture was stirred at room temperature for 16 hours, water and 28% aqueous ammonia were added. The resulting mixture was stirred, and the organic solvent was removed by evaporation under a reduced pressure. The resulting mixture was extracted with chloroform. The organic layer was dried over anhydrous sodium sulfate, filtered, and then concentrated. The resulting residue was purified via basic silica gel column chromatography to obtain tert-butyl 4-(3-((2-hydroxyethyl)amino)pyridin-2-yl)piperidin-1-carboxylate as a pale yellow solid (Compound (1-3)).
Step 4:
To a mixture of Compound (1-3) (5.5 g) and THF (100 ml), NBS (3.2 g) was added, and the mixture was stirred at room temperature for 90 minutes. To the resulting mixture, saturated aqueous sodium bicarbonate and saturated aqueous sodium sulfite were added, and the mixture was extracted with chloroform. The organic layer was separated, dried over anhydrous sodium sulfate, filtered, and then concentrated. The resulting residue was purified via basic silica gel column chromatography to obtain tert-butyl 4-(6-bromo-3-((2-hydroxyethyl)amino)pyridin-2-yl)piperidin-1-carboxylate as a brown solid (Compound (1-4)).
Step 5:
Compound (1-4) (6.9 g) was dissolved in TFA (20 ml), and the solution was stirred at room temperature for 30 minutes. After the reaction mixture was concentrated, an ammonia methanol solution (7 M, 10 ml) was added to the residue, and the resultant was stirred at room temperature. Brine was added to the reaction mixture, and the mixture was then extracted with a mixed solvent of chloroform-ethanol (4:1). The organic layer was separated, dried over anhydrous sodium sulfate, and then filtered. The filtrate was concentrated to obtain 2-((6-bromo-2-(piperidine-4-yl)pyridin-3-yl)amino)ethanol as a brown amorphous substance (Compound (1-5)).

Step 6:

A mixture of Compound (1-5) (5.1 g), Reference Example (1) (6.6 g), DMSO (34 ml), and DIPEA (30 ml) was stirred at 150° C. for 16 hours. After the mixture was cooled, water was added thereto, and the mixture was then extracted with ethyl acetate. The organic layer was dried over anhydrous sodium sulfate, filtered, and then concentrated. The resulting residue was purified via silica gel column chromatography to obtain 4-(4-(6-bromo-3-((2-hydroxyethyl)amino)pyridin-2-yl)piperidin-1-yl)-7-(2,4-dimethoxybenzyl)-5,5-dimethyl-5H-pyrrolo[2,3-d]pyrimidin-6(7H)-one as a brown solid (Compound (1-6)).

Step 7:

To a mixture of Compound (1-6) (11 g), triphenylphosphine (6.1 g), and THF (90 ml), carbon tetrabromide (7.8 g) was added under ice cooling. The resulting mixture was stirred at room temperature for 30 minutes, saturated aqueous sodium bicarbonate was added thereto, and the mixture was then extracted with ethyl acetate. The organic layer was successively washed with water and saturated brine in that order, and the resultant was then dried over anhydrous sodium sulfate. After the insoluble matter was separated via filtration, the filtrate was concentrated. The resulting residue was recrystallized from a mixture of chloroform (8 ml) and methanol (110 ml). The resulting solid was collected by filtration and dried to obtain 4-(4-(6-bromo-3-((2-bromoethyl)amino)pyridin-2-yl)piperidin-1-yl)-7-(2,4-dimethoxybenzyl)-5,5-dimethyl-5H-pyrrolo[2,3-d]pyrimidin-6(7H)-one as a white solid (Compound (1-7)).

Step 8:

A mixture of Compound (1-7) (0.85 g), THF (3 ml), and tert-butylamine (0.66 ml) was stirred at 75° C. over night. The reaction mixture was concentrated, and the resulting residue was then purified via basic silica gel column chromatography to obtain 4-(4-(6-bromo-3-((2-(tert-butylamino)ethyl)amino)pyridin-2-yl)piperidin-1-yl)-7-(2,4-dimethoxybenzyl)-5,5-dimethyl-5H-pyrrolo[2,3-d]pyrimidin-6(7H)-one as a white solid (Compound (1-8)).

Step 9:

A mixture of Compound (1-8) (0.15 g), 3-fluoropyridine-5-boronic acid (0.050 g), 1,4-dioxane (3.5 ml), aqueous sodium carbonate (2 M, 0.40 ml), and chloro(2-dicyclohexylphosphino-2',4',6'-triisopropyl-1,1'-biphenyl)[2-(2'-amino-1,1'-biphenyl)]palladium (11) (0.020 g) was stirred at 100° C. for 2 hours, cooled, and then diluted with ethyl acetate. The mixture was successively washed with water and saturated brine in that order, and the organic layer was dried over anhydrous sodium sulfate. The insoluble matter was filtered and the filtrate was then concentrated. The resulting residue was purified via basic silica gel column chromatography to obtain 4-(4-(5-((2-(tert-butylamino)ethyl)amino)-5'-fluoro-[2,3'-bipyridin]-6-yl)piperidin-1-yl)-7-(2,4-dimethoxybenzyl)-5,5-dimethyl-5H-pyrrolo[2,3-d]pyrimidin-6(7H)-one as a white solid (Compound (1-9)).

Step 10:

A mixture of Compound (1-9) (0.050 g), anisole (0.2 ml), and TFA (2 ml) was stirred at 140° C. for 1 hour under microwave irradiation. The reaction mixture was concentrated, and the resulting residue was then purified via basic silica gel column chromatography to obtain the title compound (Compound (1)).

Example 2: 4-(4-(6'-Fluoro-5-((2-(pyrrolidin-1-yl)ethyl)amino)-[2,3'-bipyridin]-6-yl)piperidin-1-yl)-5,5-dimethyl-5H-pyrrolo[2,3-d]pyrimidin-6(7H)-one (Compound (2))

The title compound (Compound (2)) was obtained in the same manner as in Example 1, except that pyrrolidine was used instead of tert-butylamine and 2-fluoropyridine-5-boronic acid was used instead of 3-fluoropyridine-5-boronic acid.

Example 3: 4-(4-(6-(1,3-Dimethyl-1H-pyrazol-5-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one (Compound (3))

The title compound (Compound (3)) was obtained in the same manner as in Example 1, except that pyrrolidine was used instead of tert-butylamine and 1,3-dimethyl-5-(4,4,5,5-tetramethyl-1,3,2-dioxaborolan-2-yl)pyrazole was used instead of 3-fluoropyridine-5-boronic acid.

Example 4: 4-(4-(3-((2-(Tert-butylamino)ethyl)amino)-6-(1-difluoromethyl)-1H-pyrazol-4-yl)pyridin-2-yl)piperidin-1-yl)-5,5-dimethyl-5H-pyrrolo[2,3-d]pyrimidin-6(7H)-one (Compound (4))

The title compound (Compound (4)) was obtained in the same manner as in Example 1, except that 1-(difluoromethyl)-4-(4,4,5,5-tetramethyl-1,3,2-dioxaborolan-2-yl)pyrazole was used instead of 3-fluoropyridine-5-boronic acid.

Example 5: 4-(4-(5',6'-Difluoro-5-((2-(isopropylamino)ethyl)amino)-[2,3'-bipyridin]-6-yl)piperidin-1-yl)-5,5-dimethyl-5H-pyrrolo[2,3-d]pyrimidin-6(7H)-one (Compound (5))

The title compound (Compound (5)) was obtained in the same manner as in Example 1, except that isopropylamine was used instead of tert-butylamine and 2,3-difluoropyridine-5-boronic acid pinacol ester was used instead of 3-fluoropyridine-5-boronic acid.

Example 6: 4-(4-(6-(2,4-Dimethylthiazol-5-yl)-3-((2-(isopropylamino)ethyl)amino) pyridin-2-yl)piperidin-1-yl)-5,5-dimethyl-5H-pyrrolo[2,3-d]pyrimidin-6(7H)-one (Compound (6))

The title compound (Compound (6)) was obtained in the same manner as in Example 1, except that isopropylamine was used instead of tert-butylamine and 2,4-dimethyl-5-(4,4,5,5-tetramethyl-1,3,2-dioxaborolan-2-yl)-1,3-thiazole was used instead of 3-fluoropyridine-5-boronic acid.

Example 7: 4-(4-(5'-Methoxy-5-((2-(pyrrolidin-1-yl)ethyl)amino)-[2,3'-bipyridin]-6-yl)piperidin-1-yl)-5,5-dimethyl-5H-pyrrolo[2,3-d]pyrimidin-6(7H)-one (Compound (7))

The title compound (Compound (7)) was obtained in the same manner as in Example 1, except that pyrolidine was used instead of tert-butylamine and 3-methoxypyridine-5-boronic acid pinacol ester was used instead of 3-fluoropyridine-5-boronic acid.

Example 8: 4-(4-(5'-Fluoro-5-((2-(pyrrolidin-1-yl)
ethyl)amino)-[2,3'-bipyridin]-6-yl)piperidin-1-yl)-5,
5-dimethyl-5H-pyrrolo[2,3-d]pyrimidin-6(7H)-one
(Compound (8))

The title compound (Compound (8)) was obtained in the same manner as in Example 1, except that pyrrolidine was used instead of tert-butylamine.

Example 9: 4-(4-(6-(3-Chloro-1-methyl-1H-pyrazol-5-yl)-3-((2-(dimethylamino)ethyl) amino)pyridin-2-yl)piperidin-1-yl)-5,5-dimethyl-5H-pyrrolo[2,3-d]pyrimidin-6(7H)-one (Compound (9))

The title compound (Compound (9)) was obtained in the same manner as in Example 1, except that dimethylamine (2 M, THF solution) was used instead of tert-butylamine and 3-chloro-1-methyl-5-(4,4,5,5-tetramethyl-1,3,2-dioxaborolan-2-yl)pyrazole was used instead of 3-fluoropyridine-5-boronic acid.

Example 10: 4-(4-(3-((2-(Isopropylamino)ethyl) amino)-6-(1-methyl-3-(trifluoromethyl)-1H-pyrazol-5-yl)pyridin-2-yl)piperidin-1-yl)-5,5-dimethyl-5H-pyrrolo[2,3-d]pyrimidin-6(7H)-one (Compound (10))

The title compound (Compound (10)) was obtained in the same manner as in Example 1, except that isopropylamine was used instead of tert-butylamine and 1-methyl-3-trifluoromethylpyrazole-5-boronic acid was used instead of 3-fluoropyridine-5-boronic acid.

Example 11: 4-(4-(6-(3-Chloro-1-methyl-1H-pyrazol-5-yl)-3-((2-(isopropylamino)ethyl) amino)pyridin-2-yl)piperidin-1-yl)-5,5-dimethyl-5H-pyrrolo[2,3-d]pyrimidin-6(7H)-one (Compound (11))

The title compound (Compound (11)) was obtained in the same manner as in Example 1, except that isopropylamine was used instead of tert-butylamine and 3-chloro-1-methyl-5-(4,4,5,5-tetramethyl-1,3,2-dioxaborolan-2-yl)pyrazole was used instead of 3-fluoropyridine-5-boronic acid.

Example 12: 4-(4-(5-((2-(Ethylamino)ethyl)amino)-5'-fluoro[2,3'-bipyridin]-6-yl)piperidin-1-yl)-5,5-dimethyl-5H-pyrrolo[2,3-d]pyrimidin-6(7H)-one (Compound (12))

The title compound (Compound (12)) was obtained in the same manner as in Example 1, except that ethylamine (2 M, THF solution) was used instead of tert-butylamine.

Example 13: 4-(4-(2'-Fluoro-5-((2-(pyrrolidin-1-yl) ethyl)amino)-[2,4'-bipyridin]-6-yl)piperidin-1-yl)-5-methyl-5H-pyrrolo[2,3-d]pyrimidin-6(7H)-one (Compound (13))

The title compound (Compound (13)) was obtained in the same manner as in Example 1, except that Reference Example (2) was used instead of Reference Example (1), pyrrolidine was used instead of tert-butylamine, and 2-fluoropyridine-4-boronic acid was used instead of 3-fluoropyridine-5-boronic acid.

Example 14: 4-(4-(6-(Furan-3-yl)-3-((2-(pyrrolidin-1-yl)ethyl)amino)pyridin-2-yl)piperidin-1-yl)-5-methyl-5H-pyrrolo[2,3-d]pyrimidin-6(7H)-one (Compound 14)

The title compound (Compound (14)) was obtained in the same manner as in Example 1, except that Reference Example (2) was used instead of Reference Example (1), pyrrolidine was used instead of tert-butylamine, and 3-(4,4,5,5-tetramethyl-1,3,2-dioxaborolan-2-yl)furan was used instead of 3-fluoropyridine-5-boronic acid.

Example 15: 4-(4-(5-((2-(Isopropylamino)ethyl) amino)-5'-methoxy-[2,3'-bipyridin]-6-yl)piperidin-1-yl)-5-methyl-5H-pyrrolo[2,3-d]pyrimidin-6(7H)-one (Compound (15))

The title compound (Compound (15)) was obtained in the same manner as in Example 1, except that Reference Example (2) was used instead of Reference Example (1), isopropylamine was used instead of tert-butylamine, and 3-methoxypyridine-5-boronic acid pinacol ester was used instead of 3-fluoropyridine-5-boronic acid.

Example 16: 4-(4-(5'-Fluoro-2'-methoxy-5-((2-(pyrrolidin-1-yl)ethyl)amino)-[2,4'-bipyridin]-6-yl)piperidin-1-yl)-5-methyl-5H-pyrrolo[2,3-d]pyrimidin-6 (7H)-one (Compound (16))

The title compound (Compound (16)) was obtained in the same manner as in Example 1, except that Reference Example (2) was used instead of Reference Example (1), pyrrolidine was used instead of tert-butylamine, and 5-fluoro-2-methoxypyridine-4-boronic acid was used instead of 3-fluoropyridine-5-boronic acid.

Example 17: 4-(4-(2'-Fluoro-5-((2-(pyrrolidin-1-yl) ethyl)amino)-[2,3'-bipyridin]-6-yl)piperidin-1-yl)-5-methyl-5H-pyrrolo[2,3-d]pyrimidin-6(7H)-one (Compound (17))

The title compound (Compound (17)) was obtained in the same manner as in Example 1, except that Reference Example (2) was used instead of Reference Example (1), pyrrolidine was used instead of tert-butylamine, and 2-fluoropyridine-3-boronic acid was used instead of 3-fluoropyridine-5-boronic acid.

Example 18: 5-Methyl-4-(4-(3-((2-(pyrrolidin-1-yl) ethyl)amino)-6-(thiophen-3-yl)pyridin-2-yl)piperidin-1-yl)-5H-pyrrolo[2,3-d]pyrimidin-6(7H)-one (Compound (18))

The title compound (Compound (18)) was obtained in the same manner as in Example 1, except that Reference Example (2) was used instead of Reference Example (1), pyrrolidine was used instead of tert-butylamine, and 3-thienylboronic acid was used instead of 3-fluoropyridine-5-boronic acid.

Example 19: 4-(4-(5'-Fluoro-5-((2-(pyrrolidin-1-yl) ethyl)amino)-[2,3'-bipyridin]-6-yl)piperidin-1-yl)-5-methyl-5H-pyrrolo[2,3-d]pyrimidin-6(7H)-one (Compound (19))

The title compound (Compound (19)) was obtained in the same manner as in Example 1, except that Reference Example (2) was used instead of Reference Example (1), and pyrrolidine was used instead of tert-butylamine.

Example 20: 5-Methyl-4-(4-(6-(1-methyl-3-(trifluoromethyl)-1H-pyrazol-5-yl)-3-((2-(pyrrolidin-1-yl) ethyl)amino)pyridin-2-yl)piperidin-1-yl)-5H-pyrrolo [2,3-d]pyrimidin-6(7H)-one (Compound (20))

The title compound (Compound (20)) was obtained in the same manner as in Example 1, except that Reference Example (2) was used instead of Reference Example (1), pyrrolidine was used instead of tert-butylamine, and 1-methyl-3-trifluoromethylpyrazole-5-boronic acid was used instead of 3-fluoropyridine-5-boronic acid.

Example 21: 4-(4-(5-((2-(Dimethylamino)ethyl) amino)-5'-methoxy-[2,3'-bipyridin]-6-yl)piperidin-1-yl)-5-methyl-5H-pyrrolo[2,3-d]pyrimidin-6(7H)-one (Compound (21))

The title compound (Compound (21)) was obtained in the same manner as in Example 1, except that Reference Example (2) was used instead of Reference Example (1), dimethylamine (2 M, THF solution) was used instead of tert-butylamine, and 3-methoxypyridine-5-boronic acid pinacol ester was used instead of 3-fluoropyridine-5-boronic acid.

Example 22: 5-Methyl-4-(4-(2'-methyl-5-((2-(pyrrolidin-1-yl)ethyl)amino)-[2,3'-bipyridin]-6-yl)piperidin-1-yl)-5H-pyrrolo[2,3-d]pyrimidin-6(7H)-one (Compound (22))

The title compound (Compound (22)) was obtained in the same manner as in Example 1, except that Reference Example (2) was used instead of Reference Example (1), pyrrolidine was used instead of tert-butylamine, and 2-methylpyridine-3-boronic acid was used instead of 3-fluoropyridine-5-boronic acid.

Example 23: 4-(4-(3-((2-(Dimethylamino)ethyl) amino)-6-(thiophen-3-yl)pyridin-2-yl)piperidin-1-yl)-5-methyl-5H-pyrrolo[2,3-d]pyrimidin-6(7H)-one (Compound (23))

The title compound (Compound (23)) was obtained in the same manner as in Example 1, except that Reference Example (2) was used instead of Reference Example (1), dimethylamine (2 M, THF solution) was used instead of tert-butylamine, and 3-thienylboronic acid was used instead of 3-fluoropyridine-5-boronic acid.

Example 24: 5-Methyl-4-(4-(3-((2-(pyrrolidin-1-yl) ethyl)amino)-6-(thiazol-2-yl)pyridin-2-yl)piperidin-1-yl)-5H-pyrrolo[2,3-d]pyrimidin-6(7H)-one (Compound (24))

Step 1:
In accordance with Steps 1 to 8 of Example 1, Reference Example (2) was used instead of Reference Example (1), and pyrrolidine was used instead of tert-butylamine to obtain 4-(4-(6-bromo-3-((2-(pyrrolidin-1-yl)ethyl)amino)pyridin-2-yl)piperidin-1-yl)-7-(2,4-dimethoxybenzyl)-5-methyl-5H-pyrrolo[2,3-d]pyrimidin-6(7H)-one as a yellow amorphous substance (Compound (24-1)).

Step 2:
A mixture of Compound (24-1) (0.044 g), 2-(tributylstannyl)thiazole (0.032 ml), bis(triphenylphosphine)palladium (II) chloride (4.7 mg), and 1,4-dioxane (1.5 ml) was stirred at 100° C. for 1 hour under microwave irradiation. The resulting mixture was concentrated, and the residue was purified via basic silica gel column chromatography to obtain 7-(2,4-dimethoxybenzyl)-5-methyl-4-(4-(3-((2-(pyrrolidin-1-yl)ethyl)amino)-6-(thiazol-2-yl)pyridin-2-yl)piperidin-1-yl)-5H-pyrrolo[2,3-d]pyrimidin-6(7H)-one as a pale yellow solid (Compound (24-2)).
Step 3:
The title compound (Compound (24)) was obtained in the same manner as in Step 10 of Example 1, except that Compound (24-2) was used instead of Compound (1-9).

Example 25: 5-Methyl-4-(4-(6-(oxazol-2-yl)-3-((2-(pyrrolidin-1-yl)ethyl)amino)pyridin-2-yl)piperidin-1-yl)-5H-pyrrolo[2,3-d]pyrimidin-6(7H)-one (Compound (25))

The title compound (Compound (25)) was obtained in the same manner as in Example 24, except that 2-(trimethyl sutanyl)oxazole was used instead of 2-(tributylstannyl)thiazole.

Example 26: 4-(5-Fluoro-5'-((2-(pyrrolidin-1-yl) ethyl)amino)-5'',6''-dihydro-[3,2':6',4''-terpyridine-]-1''(2''H)-yl)-5-methyl-5H-pyrrolo[2,3-d]pyrimidin-6 (7H)-one (Compound (26))

Step 1:
A mixture of 5-bromo-2-chloropyridine (10 g), ethanolamine (6.3 ml), copper (1) iodide (0.99 g), L-proline (1.2 g), potassium carbonate (14 g), and DMSO (40 ml) was stirred at 100° C. for 1 hour under microwave irradiation. The resulting mixture was diluted with ethyl acetate and filtered. The filtrate was successively washed with water and saturated brine in that order. The organic layer was dried over anhydrous sodium sulfate, filtered, and concentrated to obtain 2-((6-chloropyridin-3-yl)amino)ethanol (Compound (26-1)).
Step 2:
Compound (26-1) (7.2 g) was dissolved in THF (150 ml), the solution was cooled to 0° C., and NBS (7.4 g) was added thereto slowly. After the reaction mixture was stirred at room temperature for 30 minutes, the resultant was cooled to 0° C. again, and triphenylphosphine (16 g) and carbon tetrabromide (21 g) were successively added thereto in that order. After the reaction mixture was stirred at room temperature for 30 minutes, aqueous sodium sulfite (10%) was added thereto, and the resultant was then extracted with ethyl acetate. The organic layer was separated and successively washed with water and saturated brine in that order. The organic layer was dried over anhydrous sodium sulfate, filtered, and the filtrate was concentrated. Methanol was added to the resulting residue, and the resulting solid was collected by filtration. The resulting solid was dried under a reduced pressure to obtain 2-bromo-N-(2-bromoethyl)-6-chloropyridin-3-amine as a white solid (Compound (26-2)).
Step 3:
A mixture of Compound (26-2) (0.51 g), THF (2 ml), and pyrrolidine (0.30 ml) was stirred at 80° C. for 30 minutes. The reaction mixture was cooled to room temperature, diluted with ethyl acetate, and then washed with saturated brine. The organic layer was dried over anhydrous sodium sulfate and then filtered. The filtrate was concentrated to obtain 2-bromo-6-chloro-N-(2-(pyrrolidin-1-yl)ethyl)pyridin-3-amine as a brown oil substance (Compound (26-3)).
Step 4:
A mixture of Compound (26-3) (0.10 g), Reference Example (3) (0.10 g), a dichloro[1,1'-bis(diphenylphosphino)ferrocene]palladium (II) dichloromethane complex (30 mg), aqueous sodium carbonate (2 M, 0.30 ml), and 1,4-dioxane (2 ml) was stirred at 115° C. for 30 minutes, ethyl acetate was added thereto at room temperature, and the mixture was washed with water. The organic layer was dried over anhydrous sodium sulfate, filtered, and then concentrated. The resulting residue was purified via basic silica gel column chromatography to obtain 4-(6-chloro-3-((2-(pyrrolidin-1-yl)ethyl)amino)-5'-6'dihydro-[2,4'-bipyridin]-1'(2'H)-yl)-7-(2,4-dimethoxybenzyl)-5-methyl-5H-pyrrolo[2,3-d]pyrimidin-6(7H)-one as a pale yellow solid (Compound (26-4)).
Step 5:
The title compound (Compound (26)) was obtained in accordance with Steps 9 and 10 of Example 1, except that Compound (26-4) was used instead of Compound (1-8).

Example 27: 5-Methyl-4-(4-(5-(1-methyl-3-(trifluoromethyl)-1H-pyrazol-5-yl)-2-((2-(pyrrolidin-1-yl)ethyl)amino)pyridin-3-yl)piperidin-1-yl)-5H-pyrrolo[2,3-d]pyrimidin-6(7H)-one (Compound (27))

Step 1:
A mixture of 3-bromo-2-fluoropyridine (1.8 g), tert-butyl 4-(4,4,5,5-tetramethyl-1,3,2-dioxaborolan-2-yl)-1,2,3,6-tetrahydropyridine-1-carboxylate (3.4 g), tetrakis(triphenylphosphine)palladium (0) (0.60 g), aqueous sodium carbonate (2M, 6.5 ml), and 1,4-dioxane (25 ml) was stirred at 110° C. for 20 hours. The reaction mixture was cooled to room temperature, diluted with ethyl acetate, and then washed with saturated brine. The organic layer was dried over anhydrous sodium sulfate, filtered, and then concentrated. The resulting residue was purified via silica gel column chromatography to obtain tert-butyl 2-fluoro-5',6'-dihydro-[3,4'-bipyridine]-1'(2'H)-carboxylate as a pale yellow solid (Compound (27-1)).
Step 2:
A mixture of Compound (27-1) (2.7 g), ethyl acetate (20 ml), and 20% palladium hydroxide/carbon (1 g) was stirred in a hydrogen atmosphere at room temperature overnight. After nitrogen substitution, the reaction mixture was filtered. The filtrate was concentrated to obtain tert-butyl 4-(2-fluoropyridin-3-yl)piperidin-1-carboxylate as a pale yellow solid (Compound (27-2)).
Step 3:
A mixture of Compound (27-2) (0.22 g) and 2-(pyrrolidin-1-yl)ethanamine (2 ml) was stirred at 130° C. for 7 days. The reaction mixture was cooled to room temperature, diluted with ethyl acetate, and successively washed with water and saturated brine in that order. The organic layer was dried over anhydrous sodium sulfate, filtered, and then concentrated. The resulting residue was purified via basic silica gel column chromatography to obtain tert-butyl 4-(2-((2-(pyrrolidin-1-yl)ethyl)amino)pyridin-3-yl)piperidin-1-carboxylate as a pale yellow oil substance (Compound (27-3)).
Step 4:
To a mixture of Compound (27-3) (0.17 g) and acetic acid (5 ml), NBS (96 mg) was added at room temperature. The reaction mixture was stirred at room temperature for 40 minutes and then concentrated. The resulting residue was diluted with ethyl acetate, and successively washed with saturated aqueous sodium bicarbonate, saturated aqueous sodium sulfite, water, and saturated brine in that order. The organic layer was dried over anhydrous sodium sulfate, filtered, and then concentrated. The resulting residue was purified via basic silica gel column chromatography to obtain tert-butyl 4-(5-bromo-2-((2-(pyrrolidin-1-yl)ethyl)amino)pyridin-3-yl)piperidin-1-carboxylate as a brown oil (Compound (27-4)).
Step 5:
A mixture of Compound (27-4) (0.060 g), tetrakis(triphenylphosphine)palladium (0) (0.023 g), 1,4-dioxane (1 ml), 1-methyl-3-trifluoromethylpyrazole-5-boronic acid (77 mg), and aqueous sodium carbonate (2 M, 0.20 ml) was stirred at 100° C. for 3 hours. The reaction mixture was cooled to room temperature, diluted with ethyl acetate, and successively washed with water and saturated brine in that order. The organic layer was dried over anhydrous sodium sulfate, filtered, and then concentrated. The resulting residue was purified via basic silica gel column chromatography to obtain tert-butyl 4-(5-(1-methyl-3-(trifluoromethyl)-1H-pyrazol-5-yl)-2-((2-(pyrrolidin-1-yl)ethyl)amino)pyridin-3-yl)piperidin-1-carboxylate as a colorless oil substance (Compound (27-5)).
Step 6:
A mixture of Compound (27-5) (74 mg) and TFA (1 ml) was stirred at room temperature for 30 minutes and then concentrated. The resulting residue was dissolved in DMSO (1 ml), Reference Example (2) (42 mg) and DIPEA (0.18 ml) were added thereto, and the mixture was then stirred at 130° C. for 3 hours. The reaction mixture was cooled to room temperature, diluted with ethyl acetate, and successively washed with water and saturated brine in that order. The organic layer was dried over anhydrous sodium sulfate, filtered, and then concentrated. The resulting residue was purified via basic silica gel column chromatography to obtain 7-(2,4-dimethoxybenzyl)-5-methyl-4-(4-(5-(-methyl-3-(trifluoromethyl)-1H-pyrazol-5-yl)-2-((2-(pyrrolidin-1-yl)ethyl)amino)pyridin-3-yl)piperidin-1-yl)-5H-pyrrolo[2,3-d]pyrimidin-6(7H)-one as a colorless amorphous (Compound (27-6)).
Step 7:
The title compound (Compound (27)) was obtained in the same manner as in Step 10 of Example 1, except that Compound (27-6) was used instead of Compound (1-9).

Example 28: 4-(4-(3,5'-Difluoro-5-((2-(isopropylamino)ethyl)amino)-[2,3'-bipyridin]-6-yl)piperidin-1-yl)-5,5-dimethyl-5H-pyrrolo[2,3-d]pyrimidin-6(7H)-one (Compound (28))

Step 1:
A mixture of 2-bromo-5-fluoro-3-nitropyridine (1.0 g), tert-butyl 4-(4,4,5,5-tetramethyl-1,3,2-dioxaborolan-2-yl)-1,2,3,6-tetrahydropyridine-1-carboxylate (1.7 g), a 1,1'-bis(diphenylphosphino)ferrocene-palladium (II) dichloride-dichloromethane complex (66 mg), 1,4-dioxane (15 ml), sodium carbonate (0.96 g), and water (6 ml) was heated under reflux for 16 hours. The reaction mixture was cooled to room temperature and filtered. The filtrate was diluted with ethyl acetate and then washed with saturated brine. After an organic layer was separated, the organic layer was dried over anhydrous sodium sulfate, and the insoluble matter was separated via filtration. The filtrate was concentrated, and the resulting residue was purified via silica gel column chromatography to obtain tert-butyl 5-fluoro-3-nitro-5',6'-dihydro-[2,4'-bipyridine]-1'(2'H)carboxylate as a brown amorphous substance (Compound (28-1)).

Step 2:

The title compound (Compound (28)) was obtained in the same manner as in Steps 2 to 10 of Example 1, except that Compound (28-1) was used instead of Compound (1-1) and isopropylamine was used instead of tert-butylamine.

Example 29: 4-(4-(5-((2-(Dimethylamino)ethyl) amino)-5'-fluoro-[2,3'-bipyridin]-6-yl) piperazin-1-yl)-5-methyl-5H-pyrrolo[2,3-d]pyrimidin-6(7H)-one (Compound (29))

Step 1:

To a mixture of 1-(tert-butoxycarbonyl)-piperazine (4.5 g), 2-propanol (30 ml), and DIPEA (6.1 ml), a solution of 2,6-dichloro-3-nitropyridine (3.8 g) in THF (30 ml) was added, and the mixture was stirred at room temperature for 2.5 hours. After an aqueous solution of 10% phosphoric acid was added to the reaction mixture, the organic solvent was removed by evaporation under a reduced pressure. The resulting solid was collected by filtration and washed with water. The resulting solid was suspended in ethyl acetate, and the insoluble matter was separated by filtration. The filtrate was successively washed with saturated aqueous sodium bicarbonate and saturated brine in that order. The organic layer was separated, and the organic layer was then dried over anhydrous sodium sulfate. After the insoluble matter was separated by filtration, the filtrate was concentrated. The resulting residue was purified via silica gel column chromatography to obtain tert-butyl 4-(6-chloro-3-nitropyridin-2-yl) piperazine-1-carboxylate (Compound (29-1)).

Step 2:

A mixture of Compound (29-1) (1.0 g), ethanol (10 ml), water (2 ml), iron (0.80 g), and ammonium chloride (1.2 g) was stirred at 60° C. for 1.5 hours. After the reaction mixture was cooled to room temperature, saturated aqueous sodium bicarbonate and ethyl acetate were added thereto. After the insoluble matter was separated via filtration, the organic layer was separated and then washed with saturated brine. The organic layer was dried over anhydrous sodium sulfate, filtered, and then concentrated. The resulting residue was purified via silica gel column chromatography to obtain tert-butyl 4-(3-amino-6-chloropyridin-2-yl) piperazine-1-carboxylate (Compound (29-2)).

Step 3:

A mixture of Compound (29-2) (0.94 g), N,N-dimethylglycine (0.45 g), DMF (10 ml), HATU (1.8 g), and DIPEA (2 ml) was stirred at room temperature for 18 hours. HATU (0.90 g) was added again, the mixture was stirred for 18 hours, the reaction mixture was diluted with ethyl acetate, and the resultant was successively washed with water and saturated brine in that order. The organic layer was dried over anhydrous sodium sulfate, filtered, and then concentrated. The resulting residue was purified via silica gel column chromatography to obtain tert-butyl 4-(6-chloro-3-(2-(dimethylamino)acetamide)pyridin-2-yl) piperazine-1-carboxylate (Compound (29-3)).

Step 4:

A boran-dimethyl sulfide complex (2 ml) was added to a solution of Compound (29-3) (0.66 g) in THF (10 ml), and the mixture was stirred at room temperature for 18 hours. After water was added thereto slowly, 2N hydrochloric acid (4 ml) was added, and the mixture was stirred at 60° C. for 12 hours. After the reaction mixture was cooled to room temperature, 5 N aqueous sodium hydroxide (5 ml) and di-tert-butyl dicarbonate (1 M, THF solution, 1.7 ml) were added thereto, and the mixture was stirred for 24 hours. After the reaction mixture was diluted with water, the resultant was extracted with ethyl acetate. The organic layer was dried over anhydrous sodium sulfate, filtered, and the filtrate was concentrated. The resulting residue was purified via basic silica gel column chromatography to obtain tert-butyl 4-(6-chloro-3-(2-(dimethylamino)ethyl)amino)pyridin-2-yl) piperazine-1-carboxylate (Compound (29-4)).

Step 5:

The title compound (Compound (29)) was obtained in the same manner as in Steps 5 to 7 of Example 27, except that Compound (29-4) was used instead of Compound (27-4) and 3-fluoropyridine-5-boronic acid was used instead of 1-methyl-3-trifluoromethylpyrazole-5-boronic acid.

Example 30: 4-(4-(6-(5-(Difluoromethyl)-1,3,4-oxadiazol-2-yl)-3-((2-(pyrrolidin-1-yl)ethyl)amino) pyridin-2-yl)piperidin-1-yl)-5,5-dimethyl-5H-pyrrolo[2,3-d]pyrimidin-6(7H)-one (Compound (30))

Step 1:

A mixture of Compound (1-6) (2.74 g), a 1,1'-bis(diphenylphosphino)ferrocene-palladium (II) dichloride-dichloromethane complex (366 mg), triethylamine (1.87 ml), N,N-dimethylformylamide (8 ml), and methanol (8 ml) was stirred in a carbon monoxide atmosphere at 0.4 MPa and 80° C. for 12 hours. After the mixture was cooled to room temperature, the reaction mixture was diluted with ethyl acetate and then washed with water. The organic layer was dried over anhydrous sodium sulfate, filtered, and then concentrated. The resulting residue was purified via silica gel column chromatography to obtain methyl 6-(1-(7-(2,4-dimethoxybenzyl)-5,5-dimethyl-6-oxo-6,7-dihydro-5H-pyrrolo[2,3-d]pyrimidin-4-yl)piperidin-4-yl)-5-((2-hydroxyethyl)amino) picolinate as a brown amorphous substance (Compound (30-1)).

Step 2:

A mixture of Compound (30-1) (2.60 g), a hydrazine monohydrate (5 ml), and ethanol (12 ml) was heated under reflux for 1 hour. The reaction mixture was cooled to room temperature, diluted with ethyl acetate, and then washed with water. The organic layer was dried over anhydrous sodium sulfate, filtered, and the filtrate was concentrated to obtain 6-(1-(7-(2,4-dimethoxybenzyl)-5,5-dimethyl-6-oxo-6,7-dihydro-5H-pyrrolo[2,3-d]pyrimidin-4-yl)piperidin-4-yl)-5-((2-hydroxyethyl)amino)picolinic acid hydrazide as a pale yellow amorphous substance (Compound (30-2)).

Step 3:

To a mixture of Compound (30-2) (500 mg), dichloromethane (8.47 ml), and triethylamine (0.24 ml), difluoroacetic anhydride (0.11 ml) was added, and the mixture was stirred at room temperature for 15 minutes. In addition, difluoroacetic acid (0.11 ml) was added thereto, and the mixture was stirred at room temperature for 15 minutes, followed by concentration. An ammonia methanol solution (7 M, 8 ml) was added to the residue, and the resultant mixture was then stirred at room temperature. After the mixture was concentrated, the resulting residue was purified via silica gel column chromatography to obtain N'-(2,2-difluoroacetyl)-6-(1-(7-(2,4-dimethoxybenzyl)-5,5-dimethyl-6-oxo-6,7-dihydro-5H-pyrrolo[2,3-d]pyrimidin-4-yl) piperidin-4-yl)-5-((2-hydroxyethyl)amino)picolinic acid hydrazide as a white amorphous substance (Compound (30-3)).

Step 4:

A mixture of Compound (30-3) (621.2 mg), triphenylphosphine (710.5 mg), carbon tetrabromide (898.3 mg), imidazole (207.5 mg), and dichloromethane (8.47 ml) was stirred at room temperature for 3 hours. The mixture was stirred at 40° C. for an additional 1 hour, triphenylphosphine (710.5 mg) and carbon tetrabromide (898.3 mg) were added thereto, and the resultant was stirred at 40° C. for 2 days. After the mixture was concentrated, the resulting residue was purified via silica gel column chromatography to obtain Compound (30-4) as a white amorphous substance.
Step 5:
The title compound (Compound (30)) was obtained in the same manner as in Steps 8 and 10 of Example 1, except that Compound (30-4) was used instead of Compound (1-7) and pyrrolidine was used instead of tert-butylamine.

Example 31: 4-(4-(6-(5-(Difluoromethyl)-1,3,4-oxadiazol-2-yl)-3-((2-(isopropylamino)ethyl)amino)pyridin-2-yl)piperidin-1-yl)-5,5-dimethyl-5H-pyrrolo[2,3-d]pyrimidin-6(7H)-one (Compound (31))

The title compound (Compound (31)) was obtained in the same manner as in Example 30, except that isopropylamine was used instead of pyrrolidine.

Example 32: 4-(4-(3-((2-(Tert-butylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (32))

The title compound (Compound (32)) was obtained in the same manner as in Example 30, except that trifluoroacetic anhydride was used instead of difluoroacetic anhydride and tert-butylamine was used instead of pyrrolidine.

Example 33: 4-(4-(3-((2-(Isopropylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (33))

The title compound (Compound (33)) was obtained in the same manner as in Example 30, except that trifluoroacetic anhydride was used instead of difluoroacetic anhydride and isopropylamine was used instead of pyrrolidine.

Example 34: 4-(4-(3-((2-(Tert-butyl(methyl)amino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one (Compound (34))

The title compound (Compound (34)) was obtained in the same manner as in Example 30, except that trifluoroacetic anhydride was used instead of difluoroacetic anhydride and methyl-tert-butylamine was used instead of pyrrolidine.

Example 35: (S)-5,5-Dimethyl-4-(4-(3-((pyrrolidin-2-yl-methyl)amino)-6-(5-(trifluoromethyl)-1,3,4-oxadiazol-2-yl)pyridin-2-yl)piperidin-1-yl)-5H-pyrrolo[2,3-d]pyrimidin-6(7H)-one (Compound (35))

Step 1:
A mixture of methyl 5-fluoropyridine-2-carboxylate (0.5 g), tert-butyl (S)-2-(aminomethyl)pyrrolidin-1-carboxylate (1.0 g), DIPEA (0.67 ml), and DMSO (3.0 ml) was stirred at 130° C. for 1.5 hours and at 140° C. for 1 hour. The mixture was cooled to room temperature and then purified via silica gel column chromatography to obtain methyl (S)-5-(((1-(tert-butoxycarbonyl)pyrrolidin-2-yl)methyl)amino)picolinate (Compound (35-1)) as a colorless oil substance.
Step 2:
To a mixture of Compound (35-1) (601 mg) and THF (9 ml), NBS (319 mg) was added at room temperature, and the resultant was stirred for 1 hour. After saturated aqueous sodium bicarbonate and saturated aqueous sodium sulfite were added to the resulting mixture, the mixture was extracted with ethyl acetate. The organic layer was separated, dried over anhydrous sodium sulfate, filtered, and then concentrated. The resulting residue was purified via silica gel column chromatography to obtain methyl (S)-6-bromo-5-(((1-(tert-butoxycarbonyl)pyrrolidin-2-yl)methyl)amino)picolinate as a colorless oil substance (Compound (35-2)).
Step 3:
To a mixture of zinc powder (512 mg) and N,N-dimethylacetamide (5 ml), trimethylsilyl chloride (0.06 ml) was added, and the mixture was stirred at room temperature for 10 minutes. Subsequently, Reference Example (4) (1.2 g) was added and the mixture was stirred at 60° C. for 1 hour to give the solution of the organic zinc reagent in N,N-dimethylacetamide. Compound (35-2) (649 mg), palladium acetate (35 mg), 2-dicyclohexylphosphino-2',6'-dimethoxybiphenyl (64 mg), and N,N-dimethylacetamide (1.5 ml) were introduced into another reaction vessel, and the mixture was stirred at room temperature for 10 minutes. The solution of the organic zinc reagent in N,N-dimethylacetamide was added to the resulting mixture, and the mixture was stirred at 60° C. for 5 hours. The reaction mixture was cooled to room temperature, and water (5 ml) and ethyl acetate (5 ml) were added to the reaction mixture, followed by filtration. The organic layer was separated and then washed with water and saturated brine. The organic layer was dried over anhydrous magnesium sulfate, filtered, and concentrated. The resulting residue was purified via basic silica gel column chromatography to obtain methyl (S)-5-(((1-(tert-butoxycarbonyl)pyrrolidin-2-yl)methyl)amino)-6-(1-(7-(2,4-dimethoxybenzyl)-5,5-dimethyl-6-oxo-6,7-dihydro-5H-pyrrolo[2,3-d]pyrimidin-4-yl)piperidin-4-yl)picolinate as a pale yellow amorphous substance (Compound (35-3)).
Step 4:
In the same manner as in Steps 2 to 4 of Example 30, (S)-tert-butyl 2-(((2-(1-(7-(2,4-dimethoxybenzyl)-5,5-dimethyl-6-oxo-6,7-dihydro-5H-pyrrolo[2,3-d]pyrimidin-4-yl)piperidin-4-yl)-6-(5-(trifluoromethyl)-1,3,4-oxadiazol-2-yl)pyridin-3-yl)amino)methyl)pyrrolidin-1-carboxylic acid (Compound (35-4)) was obtained as a pale yellow amorphous substance, except that Compound (35-3) was used instead of Compound (30-1) and trifluoroacetic anhydride was used instead of difluoroacetic anhydride.
Step 5:
The title compound (Compound (35)) was obtained in the same manner as in Step 10 of Example 1, except that Compound (35-4) was used instead of Compound (1-9).

Example 36: 5,5-Dimethyl-4-(4-(6-(5-methyl-1,3,4-thiadiazol-2-yl)-3-((2-(pyrrolidin-1-yl)ethyl)amino)pyridin-2-yl)piperidin-1-yl)-5H-pyrrolo[2,3-d]pyrimidin-6(7H)-one (Compound (36))

Step 1:
To a mixture of 5-bromopicolinic acid (10 g) and methanol (50 ml), concentrated sulfuric acid (1 ml) was added, and heated under reflux for 3 hours. Thereafter, the reaction mixture was concentrated. The resulting residue was diluted with ethyl acetate and then successively washed with water, saturated aqueous sodium bicarbonate, and saturated brine in that order. The organic layer was dried over anhydrous magnesium sulfate, filtered, and the filtrate was concentrated. To the resulting residue, ethanol (50 ml) and a hydrazine monohydrate (10 ml) were added, the resultant was heated under reflux for 3 hours, and the reaction mixture was then concentrated. Water was added to the resulting residue, and the resulting solid was collected by filtration to obtain 5-bromopicolinic acid hydrazide as a yellow solid (Compound (36-1)).

Step 2:

To a mixture of Compound (36-1) (1.5 g), acetonitrile (25 ml), and triethylamine (1 ml), acetic anhydride (0.79 ml) was added, and the resultant was stirred at room temperature for 30 minutes. Water was added to the reaction mixture, and the resulting solid was collected by filtration to obtain N'-acetyl-5-bromopicolinic acid hydrazide as a white solid (Compound (36-2)).

Step 3:

A mixture of Compound (36-2) (1.78 g), Lawesson's reagent (2.8 g), and 1,4-dioxane (35 ml) was heated under reflux for 1 hour, and the reaction mixture was then concentrated. The resulting residue was purified via silica gel column chromatography. The resulting solid was suspended in methanol:water (5:1). The solid was collected by filtration to obtain 2-(5-bromopyridin-2-yl)-5-methyl-1,3,4-thiadiazole as a white solid (Compound (36-3)).

Step 4:

A mixture of Compound (36-3) (1.15 g), ethanolamine (0.81 ml), copper (I) iodide (85 mg), L-proline (103 mg), potassium carbonate (1.24 g), and DMSO (10 ml) was stirred at 80° C. overnight. After the mixture was cooled to room temperature, the mixture was diluted with water and ethyl acetate, and the diluted mixture was filtered, and extracted 3 times with chloroform. The organic layer was dried over anhydrous magnesium sulfate, filtered, and then concentrated. The resulting residue was diluted with methanol, and a methanol hydrochloride solution was added to concentrate the mixture. The resulting residue was suspended in ethyl acetate and collected by filtration. The resulting solid was suspended in chloroform, and saturated aqueous sodium bicarbonate was added thereto. The organic layer was separated, and the aqueous layer was extracted 5 times with chloroform/methanol (10:1). The organic layer was combined therewith, dried over anhydrous magnesium sulfate, and concentrated. The resulting residue was suspended in chloroform. The solid was collected by filtration to obtain 2-((6-(5-methyl-1,3,4-thiadiazol-2-yl)pyridin-3-yl)amino)ethanol as a brown solid (Compound (36-4)).

Step 5:

To a mixture of Compound (36-4) (559 mg), THF (10 ml), and acetonitrile (5 ml), NBS (421 mg) was added, and the mixture was stirred at room temperature for 30 minutes. Aqueous sodium sulfite and saturated brine were added to the reaction mixture, and the mixture was extracted 5 times with chloroform/methanol (10:1). The organic layer was combined therewith, dried over anhydrous magnesium sulfate, and concentrated. Diethyl ether was added to the resulting residue, and the resulting solid was collected by filtration to obtain 2-((2-bromo-6-(5-methyl-1,3,4-thiadiazol-2-yl)pyridin-3-yl)amino)ethanol (Compound (36-5)) as a brown solid.

Step 6:

To a mixture of zinc powder (705 mg) and N,N-dimethylacetamide (6 ml), trimethylsilyl chloride (0.03 ml) was added, and the resulting mixture was stirred at room temperature for 10 minutes. Subsequently, Reference Example (4) (2.25 g) was added thereto and the mixture was stirred at 60° C. for 30 minutes to give the solution of the organic zinc reagent in N,N-dimethylacetamide. Compound (36-5) (680 mg), palladium acetate (24 mg), 2-dicyclohexylphosphino-2',6'-dimethoxybiphenyl (89 mg), and N,N-dimethylacetamide (6 ml) were introduced into another reaction vessel, and the mixture was stirred at room temperature for 10 minutes. The solution of the organic zinc reagent in N,N-dimethylacetamide was added to the resulting mixture, and the mixture was stirred at 60° C. for 5 hours. The reaction mixture was cooled to room temperature, and water (5 ml) and ethyl acetate (5 ml) were added to the reaction mixture. After filtration, the organic layer was separated and then washed with water and saturated brine. The organic layer was dried over anhydrous magnesium sulfate, filtered, and concentrated. The resulting residue was purified via basic silica gel column chromatography to obtain 7-(2,4-dimethoxybenzyl)-4-(4-(3-((2-hydroxyethyl)amino)-6-(5-methyl-1,3,4-thiadiazol-2-yl)pyridin-2-yl)piperidin-1-yl)-5,5-dimethyl-5H-pyrrolo[2,3-d]pyrimidin-6(7H)-one as a pale yellow amorphous substance (Compound (36-6)).

Step 7:

To a mixture of Compound (36-6) (804 mg), triphenylphosphine (501 mg), and THF (6 ml), carbon tetrabromide (634 mg) was added under ice cooling. The resulting mixture was stirred at room temperature for 1 hour, saturated aqueous sodium bicarbonate was added thereto, and the mixture was then extracted with ethyl acetate. The organic layer was successively washed with water and saturated brine in that order, dried over anhydrous magnesium sulfate, filtered, and then concentrated. The resulting residue was purified via basic silica gel column chromatography to obtain 4-(4-(3-((2-bromoethyl)amino)-6-(5-methyl-1,3,4-thiadiazol-2-yl)pyridin-2-yl)piperidin-1-yl)-7-(2,4-dimethoxybenzyl)-5,5-dimethyl-5H-pyrrolo[2,3-d]pyrimidin-6 (7H)-one (Compound (36-7)) as a pale yellow amorphous.

Step 8:

The title compound (Compound (36)) was obtained in the same manner as in Steps 8 and 10 of Example 1, except that Compound (36-7) was used instead of Compound (1-7) and pyrrolidine was used instead of tert-butylamine.

Example 37: 4-(4-(3-((2-(Tert-butylamino)ethyl)amino)-6-(5-(difluoromethyl)-1,3,4-thiadiazol-2-yl)pyridin-2-yl)piperidin-1-yl)-5,5-dimethyl-5H-pyrrolo[2,3-d]pyrimidin-6(7H)-one (Compound (37))

The title compound (Compound (37)) was obtained in the same manner as in Example 36, except that difluoroacetic anhydride was used instead of acetic anhydride and tert-butylamine was used instead of pyrrolidine.

Example 38: 4-(4-(6-(5-(Difluoromethyl)-1,3,4-thiadiazol-2-yl)-3-((2-(dimethylamino)ethyl)amino)pyridin-2-yl)piperidin-1-yl)-5,5-dimethyl-5H-pyrrolo[2,3-d]pyrimidin-6(7H)-one (Compound (38))

The title compound (Compound (38)) was obtained in the same manner as in Example 36, except that was used instead of difluoroacetic anhydride acetic anhydride and dimethylamine was used instead of pyrrolidine.

Example 39: 4-(4-(6-(5-(Difluoromethyl)-1,3,4-thiadiazol-2-yl)-3-((2-(isopropylamino)ethyl)amino)pyridin-2-yl)piperidin-1-yl)-5,5-dimethyl-5H-pyrrolo[2,3-d]pyrimidin-6(7H)-one (Compound (39))

The title compound (Compound (39)) was obtained in the same manner as in Example 37, except that isopropylamine was used instead of tert-butylamine.

Example 40: 4-(4-(3-((2-(Tert-butylamino)ethyl)amino)-6-(5-cyclopropyl-1,3,4-thiadiazol-2-yl)pyridin-2-yl)piperidin-1-yl)-5,5-dimethyl-5H-pyrrolo[2,3-d]pyrimidin-6(7H)-one (Compound (40))

The title compound (Compound (40)) was obtained in the same manner as in Example 36, except that cyclopropanecarboxylic acid chloride was used instead of acetic anhydride and tert-butylamine was used instead of pyrrolidine.

Example 41: 4-(4-(3-((2-(Tert-butylamino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one (Compound (41))

Step 1:
A mixture of 5-fluoropicolinonitrile (25 g), DMSO (100 ml), and 2-aminoethanol (25 ml) was stirred at 75° C. for 40 minutes. The mixture was cooled to room temperature, diluted with water, and then extracted with ethyl acetate. The organic layer was dried over anhydrous sodium sulfate and then filtered. The filtrate was concentrated to obtain 5-((2-hydroxyethyl)amino)picolinonitrile as a white solid (Compound (41-1)).
Step 2:
To a mixture of Compound (41-1) (29 g) and THF (300 ml), NBS (32 g) was added, and the mixture was stirred at room temperature for 3 hours. Aqueous sodium thiosulfate (10%, 100 ml) was added to the mixture, and the mixture was then extracted with ethyl acetate. The organic layer was dried over anhydrous sodium sulfate, filtered, and then concentrated. The resulting residue was recrystallized with ethyl acetate (110 ml). The resulting solid was collected by filtration and dried to obtain 6-bromo-5-((2-hydroxyethyl)amino)picolinonitrile as a white solid (Compound (41-2)).
Step 3:
To a mixture of Compound (41-2) (3.4 g) and pyridine (4.0 ml), acetic anhydride (4.0 ml) was added, and the mixture was stirred at room temperature for 30 minutes. The resulting mixture was diluted with ethyl acetate, successively washed with water and saturated brine in that order, and then dried over anhydrous sodium sulfate. The resultant was filtered and concentrated. The resulting residue was recrystallized with isopropyl acetate to obtain 2-((2-bromo-6-cyanopyridin-3-yl)amino)ethyl acetic acid ester as a white solid (Compound (41-3)).
Step 4:
To a mixture of zinc powder (0.97 g) and N,N-dimethylacetamide (5 ml), trimethylsilyl chloride (0.089 ml) was added, and the mixture was sonicated with stirring at 50° C. for 15 minutes. After the reaction mixture was cooled to room temperature, N,N-dimethylacetamide (44 ml) and Reference Example (4) (4.8 g) were added thereto, and the mixture was sonicated with stirring at 50° C. for 20 minutes. After the reaction mixture was cooled to room temperature, an excess amount of zinc powder was separated by filtration, the resulting mixture was added to the separately prepared mixture of Compound (41-3) (1.8 g), palladium (II) acetate (0.16 g), dicyclohexyl(2',6'-dimethoxy-[1,1'-diphenyl]-2-yl)phosphine (0.17 g), and N,N-dimethylacetamide (4 ml), and the resulting mixture was stirred at 70° C. for 2 hours. After the reaction was cooled to room temperature, the resulting mixture was diluted with ethyl acetate and water, the insoluble matter was filtered, the resulting filtrate was successively washed with water and saturated brine in that order, and the resultant was then dried over anhydrous sodium sulfate. After filtration, the filtrate was concentrate, the resulting residue was purified via silica gel column chromatography to obtain 2-((6-cyano-2-(1-(7-(2,4-dimethoxybenzyl)-5,5-dimethyl-6-oxo-6,7-dihydro-5H-pyrrolo[2,3-d]pyrimidin-4-yl)piperidin-4-yl)pyridin-3-yl)amino)ethyl acetate as a pale yellow amorphous substance (Compound (41-4)).
Step 5:
To a mixture of Compound (41-4) (8.5 g) and ethanol (100 ml), aqueous hydroxylamine (50%, 2.8 ml) was added, and the mixture was then stirred at 60° C. for 10 minutes. The resulting mixture was concentrated and dried to obtain 2-((2-(1-(7-(2,4-dimethoxybenzyl)-5,5-dimethyl-6-oxo-6,7-dihydro-5H-pyrrolo[2,3-d]pyrimidin-4-yl)piperidin-4-yl)-6-(N-hydroxycarbamimidoyl)pyridin-3-yl)amino)ethyl acetate as a pale yellow amorphous substance (Compound (41-5)).
Step 6:
A mixture of Compound (41-5) and THF (100 ml) was cooled to 0° C., difluoroacetic anhydride (2.2 ml) and pyridine (25 ml) were successively added thereto, and the mixture was stirred at room temperature for 5 minutes. The resulting mixture was stirred at 60° C. for an additional 2 hours. After the mixture was cooled, hydrochloric acid (0.5M, 30 ml) was added, and the resultant was extracted with ethyl acetate. The organic layer was separated, successively washed with water and saturated brine in that order, and then dried over anhydrous sodium sulfate. The resultant was filtered and then concentrated. The resulting residue was purified via silica gel column chromatography to obtain the title compound (i.e., 2-((6-(5-(difluoromethyl)-1,2,4-oxadiazol-3-yl)-2-(1-(7-(2,4-dimethoxybenzyl)-5,5-dimethyl-6-oxo-6,7-dihydro-5H-pyrrolo[2,3-d]pyrimidin-4-yl)piperidin-4-yl)pyridin-3-yl)amino)ethyl acetate as a white solid (Compound (41-6)).
Step 7:
A mixture of Compound (41-6) (9.8 g), methanol (100 ml), and THF (50 ml) was cooled to 0° C., aqueous sodium hydroxide (5M, 0.85 ml) was added thereto, and the mixture was stirred at 0° C. for 1 hour. Hydrochloric acid (5M, 0.85 ml) was added to the resulting mixture, and the mixture was stirred at room temperature for 2 hours. The resulting solid was collected by filtration, washed with methanol (50 ml), and dried under a reduced pressure to obtain 4-(4-(6-(5-(difluoromethyl)-1,2,4-oxadiazol-3-yl)-3-((2-hydroxyethyl)amino)pyridin-2-yl)piperidin-1-yl)-7-(2,4-dimethoxybenzyl)-5,5-dimethyl-5H-pyrrolo[2,3-d]pyrimidin-6(7H)-one as a white solid (Compound (41-7)).
Step 8:
The title compound (Compound (41)) was obtained in accordance with Steps 7, 8, and 10 of Example 1, except that Compound (41-7) was used instead of Compound (1-6).

Example 42: 4-(4-(3-((2-(Isopropylamino)ethyl)amino)-6-(5-(trifluoromethyl)-1,2,4-oxadiazol-3-yl)pyridin-2-yl)piperidin-1-yl)-5,5-dimethyl-5H-pyrrolo[2,3-d]pyrimidin-6(7H)-one (Compound (42))

The title compound (Compound (42)) was obtained in the same manner as in Example 41, except that trifluoroacetic anhydride was used instead of difluoroacetic anhydride and isopropylamine was used instead of tert-butylamine.

Example 43: 4-(4-(3-((2-(Tert-butylamino)ethyl) amino)-6-(3-(trifluoromethyl)-1,2,4-oxadiazol-5-yl) pyridin-2-yl)piperidin-1-yl)-5,5-dimethyl-5H-pyrrolo[2,3-d]pyrimidin-6(7H)-one (Compound (43))

Step 1:

2-((2-(1-(7-(2,4-Dimethoxybenzyl)-5,5-dimethyl-6-oxo-6,7-dihydro-5H-pyrrolo[2,3-d]pyrimidin-4-yl)piperidin-4-yl)-6-(5-(trifluoromethyl)-1,2,4-oxadiazol-3-yl)pyridin-3-yl)amino)ethyl acetate (Compound (43-1)) was obtained in accordance with Steps 1 to 6 of Example 41, except that trifluoroacetic anhydride was used instead of difluoroacetic anhydride.

Step 2:

A mixture of Compound (43-1) (0.44 g), DMF (10 ml), hydroxyamine hydrochloride (0.43 g), and tert-butoxypotassium (0.69 g) was stirred at 70° C. for 1 hour. The reaction mixture was cooled to room temperature, diluted with ethyl acetate, and successively washed with water and saturated brine in that order. The organic layer was dried over anhydrous sodium sulfate and then filtered. The filtrate was concentrated to obtain 2-((2-(1-(7-(2,4-dimethoxybenzyl)-5,5-dimethyl-6-oxo-6,7-dihydro-5H-pyrrolo[2,3-d]pyrimidin-4-yl)piperidin-4-yl)-6-(3-(trifluoromethyl)-1,2,4-oxadiazol-5-yl)pyridin-3-yl)amino)ethyl acetate (Compound (43-2)) as a pale yellow amorphous substance.

Step 3:

The title compound (Compound (43)) was obtained in the same manner as in Steps 7 and 8 of Example 41, except that Compound (43-2) was used instead of Compound (41-6).

Example 44: 5,5-Dimethyl-4-(4-(3-((2-(pyrrolidin-1-yl)ethyl)amino)-6-(3-(trifluoromethyl)-1,2,4-oxadiazol-5-yl)pyridin-2-yl)piperidin-1-yl)-5H-pyrrolo [2,3-d]pyrimidin-6(7H)-one (Compound (44))

The title compound (Compound (44)) was obtained in the same manner as in Example 43, except that pyrrolidine was used instead of tert-butylamine.

Comparative Example B: 4-(4-(4-((2-(Tert-butylamino)ethyl)amino)-5'-fluoro-[2,3'-bipyridin]-6-yl) piperidin-1-yl)-5,5-dimethyl-5H-pyrrolo[2,3-d]pyrimidin-6(7H)-one Step 1:

A mixture of 2,6-dibromo-4-nitropyridine (1 g), potassium carbonate (490.3 mg), 2-aminoethanol (0.32 ml), and DMSO (10 ml) was stirred at 60° C. for 1.5 hours. Water was added to the reaction mixture, and the mixture was extracted with ethyl acetate. The organic layer was dried over anhydrous sodium sulfate, filtered, and then concentrated. The resulting residue was purified via silica gel column chromatography to obtain 2-((2,6-dibromopyridine-4-yl)amino) ethanol as a brown oil substance (Comparative Example B (1-1)).

Step 2:

A mixture of Comparative Example B (1-1) (212 mg), 5-fluoropyridine-3-boronic acid (50 mg), tetrakis(triphenylphosphine)palladium (0) (82.8 mg), aqueous sodium carbonate (2M, 0.39 ml), and 1,4-dioxane (7.16 ml) was stirred at 100° C. for 1 hour. Water was added to the reaction mixture, and the mixture was extracted with ethyl acetate. The organic layer was dried over anhydrous sodium sulfate and then concentrated. The resulting residue was purified via silica gel column chromatography to obtain 2-((6-bromo-5'-fluoro-[2,3'-bipyridin]-4-yl)amino)ethanol as a crude product (Comparative Example B (1-2)). The product was subjected to the subsequent step without further purification.

Step 3:

A mixture of Comparative Example B (1-2), carbon tetrabromide (237.6 mg), triphenylphosphine (187.9 mg), THF (3 ml), and dichloromethane (1 ml) was stirred at room temperature for 30 minutes. Aqueous solution of saturated sodium bicarbonate and water were added to the reaction mixture, and the mixture was extracted with ethyl acetate. The organic layer was dried over anhydrous sodium sulfate, filtered, and then concentrated. The resulting residue was purified via silica gel column chromatography to obtain 6-bromo-N-(2-bromoethyl)-5'-fluoro-[2,3'-bipyridine]-4-amine as a yellow amorphous substance (Comparative Example B (1-3)).

Step 4:

A mixture of Comparative Example B (1-3) (65.7 mg), tert-butylamine (0.2 ml), and THF (1 ml) was stirred at 80° C. for 4 hours. To the reaction mixture, tert-butylamine (0.2 ml) was added, and the mixture was stirred at 90° C. for 2 hours. Water was added to the reaction mixture, and the mixture was then extracted with ethyl acetate. The organic layer was dried over anhydrous sodium sulfate, filtered, and then concentrated. The resulting residue was purified via basic silica gel column chromatography to obtain N1-(6-bromo-5'-fluoro-[2,3'-bipyridin]-4-yl)-N2-(tert-butyl)ethane-1,2-diamine as a yellow amorphous substance (Comparative Example B (1-4)).

Step 5:

A mixture of Comparative Example B (1-4) (57.5 mg), Reference Example (5) (69.5 mg), a 1,1'-bis(diphenylphosphino)ferrocene-palladium (II) dichloride-dichloromethane complex (12.8 mg), aqueous sodium carbonate (2M, 0.10 ml), and 1,4-dioxane (1.57 ml) was stirred at 100° C. for 3 hours. Water was added to the reaction mixture, and the mixture was extracted with ethyl acetate. The organic layer was dried over anhydrous sodium sulfate, filtered, and then concentrated. The resulting residue was purified via basic silica gel column chromatography to obtain 4-(4'((2-(tert-butylamino)ethyl)amino)-5-fluoro-5",6"-dihydro-[3,2':6', 4"-terpyridin]-1"(2"H)-yl)-5,5-dimethyl-5H-pyrrolo[2,3-d] pyrimidin-6(7H)-one as a brown amorphous substance (Comparative Example B (1-5)).

Step 6:

A mixture of Comparative Example B (1-5) (16 mg), 20% palladium hydroxide/carbon (15 mg), ethyl acetate (1 ml), ethanol (0.1 ml), methanol (0.1 ml), THF (0.1 ml), DMF (0.1 ml), and TFA (0.01 ml) was stirred in a hydrogen atmosphere at room temperature for 4 hours. After nitrogen substitution, the reaction mixture was filtered. The filtrate was concentrated, and the resulting residue was purified via basic silica gel column chromatography to obtain the title compound (i.e., Comparative Example B).

Table 1 shows chemical formulae and physical properties of Compounds of Examples 1 to 44.

TABLE 1

| Compound No. | Structural formula | Values of physical properties |
|---|---|---|
| 1 | | ¹H-NMR (CDCl₃) δ: 8.91 (1H, t, J = 1.5 Hz), 8.31 (1H, d, J = 2.9 Hz), 8.27 (1H, s), 8.04 (1H, ddd, J = 10.0, 2.9, 1.5 Hz), 7.55 (1H, d, J = 8.5 Hz), 6.96 (1H, d, J = 8.5 Hz), 4.66-4.58 (2H, m), 3.28-3.04 (5H, m), 2.94-2.90 (2H, m), 2.11-2.02 (4H, m), 1.54 (6H, s), 1.16 (9H, s). |
| 2 | | ¹H-NMR (CDCl₃) δ: 8.72 (1H, d, J = 2.6 Hz), 8.60 (1H, br s), 8.38-8.30 (1H, m), 8.33 (1H, s), 7.48 (1H, d, J = 8.4 Hz), 6.97-6.91 (2H, m), 4.88 (1H, br t, J = 4.4 Hz), 4.64-4.55 (2H, m), 3.25-3.14 (4H, m), 3.08-2.96 (1H, m), 2.86 (2H, t, J = 6.0 Hz), 2.61-2.53 (4H, m), 2.12-1.96 (4H, m), 1.85-1.78 (4H, m), 1.56 (6H, s) |
| 3 | | ¹H-NMR (DMSO-D₆) δ: 8.19 (1H, s), 7.32 (1H, d, J = 8.4 Hz), 6.95 (1H, d, J = 8.4 Hz), 6.23 (1H, s), 5.60 (1H, t, J = 5.7 Hz), 4.48-4.41 (2H, m), 3.90 (3H, s), 3.28-3.06 (7H, m), 2.67-2.61 (2H, m), 2.54-2.45 (2H, m), 2.09 (3H, s), 1.91-1.84 (2H, m), 1.79-1.63 (6H, m), 1.36 (6H, s). |

TABLE 1-continued
| Compound No. | Structural formula | Values of physical properties |
|---|---|---|
| 4 | 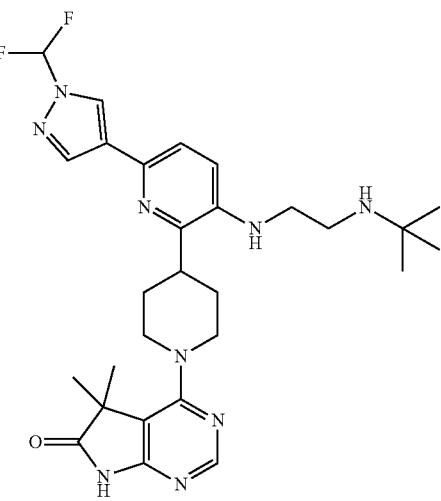 | $^1$H-NMR (CDCl$_3$) δ: 8.35 (1H, s), 8.15 (1H, s), 8.02 (1H, s), 7.26 (1H, d, J = 8.5 Hz), 7.19 (2H, t, J = 52.6 Hz), 6.89 (1H, d, J = 8.5 Hz), 4.84 (1H, s), 4.64 (2H, d, J = 12.9 Hz), 3.22-3.13 (4H, m), 3.06-2.98 (1H, m), 2.94 (2H, t, J = 5.6 Hz), 2.08-2.03 (4H, m), 1.55 (6H, s), 1.15 (9H, s). |
| 5 | 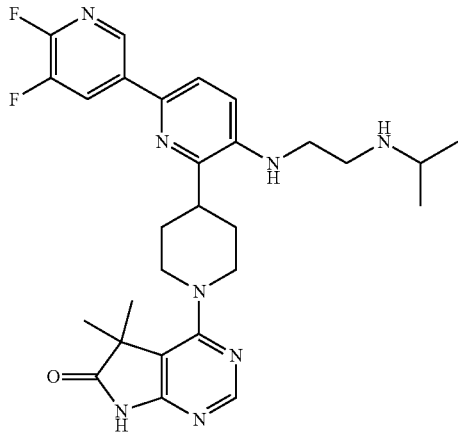 [SMILES: CC(C)NCCNc1ccc(-c2cnc(F)c(F)c2)nc1C1CCN(c2ncnc3c2C(C)(C)C(=O)N3)CC1] | $^1$H-NMR (DMSO-D$_6$) δ: 8.39 (1H, t, J = 1.8 Hz), 8.25-8.19 (1H, m), 8.04 (1H, s), 7.56 (1H, d, J = 8.8 Hz), 6.83 (1H, d, J = 8.8 Hz), 5.62 (1H, t, J = 5.6 Hz), 4.35-4.27 (2H, m), 3.11-2.91 (5H, m), 2.58-2.52 (3H, m), 1.79-1.71 (2H, m), 1.68-1.56 (2H, m), 1.22 (6H, s), 0.81 (6H, d, J = 6.1 Hz). |
| 6 | 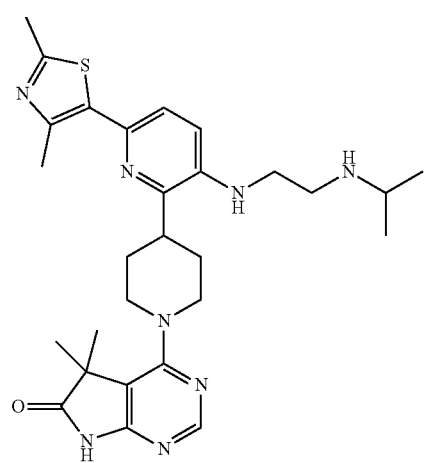 [SMILES: Cc1nc(C)c(-c2ccc(NCCNC(C)C)c(C3CCN(c4ncnc5c4C(C)(C)C(=O)N5)CC3)n2)s1] | $^1$H-NMR (CDCl$_3$) δ: 8.33 (1H, s), 7.26 (1H, d, J = 8.5 Hz), 6.90 (1H, d, J = 8.5 Hz), 4.76 (1H, s), 4.58 (2H, d, J = 12.9 Hz), 3.24-3.17 (4H, m), 3.06-2.96 (3H, m), 2.90-2.81 (1H, m), 2.63 (3H, s), 2.59 (3H, s), 2.09-2.00 (4H, m), 1.54 (6H, s), 1.11 (6H, d, J = 6.1 Hz). |

TABLE 1-continued
| Compound No. | Structural formula | Values of physical properties |
|---|---|---|
| 7 | 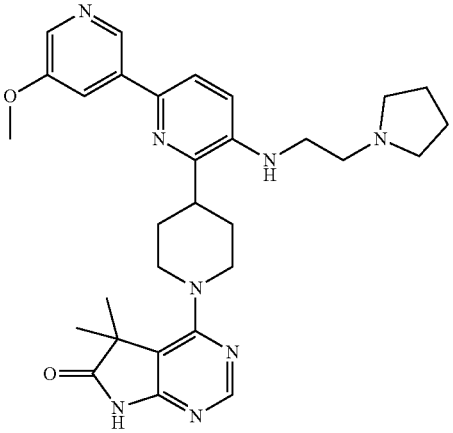 [SMILES: COc1cncc(-c2ccc(NCCN3CCCC3)c(C3CCN(c4ncnc5c4C(C)(C)C(=O)N5)CC3)n2)c1] | ¹H-NMR (DMSO-D₆) δ: 11.09 (1H, s), 8.73 (1H, s), 8.21 (1H, s), 8.16 (1H, s), 7.79 (1H, s), 7.73 (1H, d, J = 8.4 Hz), 7.00 (1H, d, J = 8.4 Hz), 5.68 (1H, s), 4.48 (2H, d, J = 12.8 Hz), 3.83 (3H, s), 3.27-3.15 (6H, m), 2.70-2.64 (5H, m), 1.94-1.70 (8H, m), 1.39 (6H, s). |
| 8 | 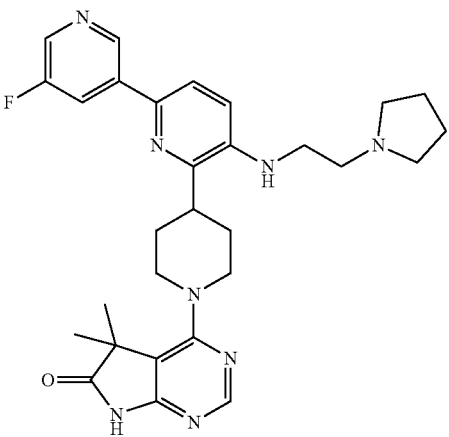 [SMILES: CC1(C)C(=O)Nc2ncnc(N3CCC(c4nc(-c5cncc(F)c5)ccc4NCCN4CCCC4)CC3)c21] | ¹H-NMR (DMSO-D₆) δ: 11.09 (1H, s), 9.02 (1H, s), 8.42 (1H, br s), 8.22 (1H, s), 8.11 (1H, d, J = 10.6 Hz), 7.78 (1H, d, J = 8.8 Hz), 7.01 (1H, d, J = 8.8 Hz), 5.79 (1H, br s), 4.49 (2H, d, J = 13.2 Hz), 3.24-3.14 (5H, m), 2.71-2.52 (6H, m), 1.94-1.69 (8H, m), 1.39 (6H, s). |
| 9 | 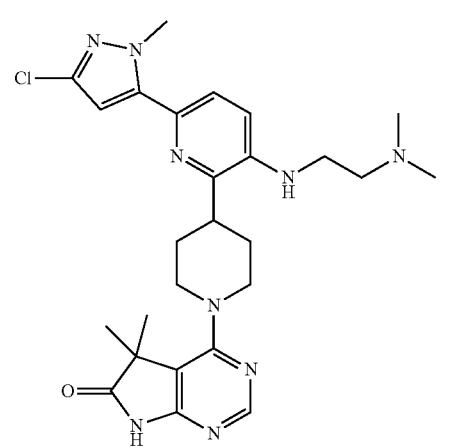 [SMILES: CN(C)CCNc1ccc(-c2cc(Cl)nn2C)nc1C1CCN(c2ncnc3c2C(C)(C)C(=O)N3)CC1] | ¹H-NMR (CDCl₃) δ: 8.33 (1H, s), 7.29 (1H, d, J = 8.5 Hz), 6.90 (1H, d, J = 8.5 Hz), 6.31 (1H, s), 4.89 (1H, s), 4.57 (2H, d, J = 12.9 Hz), 4.09 (3H, s), 3.21-3.14 (4H, m), 3.03-2.98 (1H, m), 2.67-2.62 (2H, m), 2.30 (6H, s), 2.02-1.96 (4H, m), 1.54 (6H, s). |

TABLE 1-continued

| Compound No. | Structural formula | Values of physical properties |
|---|---|---|
| 10 | | ¹H-NMR (DMSO-D₆) δ: 8.21 (1H, s), 7.51 (1H, d, J = 8.8 Hz), 7.02 (1H, d, J = 8.8 Hz), 6.99 (1H, s), 5.85 (1H, t, J = 5.4 Hz), 4.51-4.44 (2H, m), 4.09 (3H, s), 3.29-3.07 (5H, m), 2.76-2.70 (3H, m), 1.96-1.89 (2H, m), 1.80-1.67 (2H, m), 1.38 (6H, s), 0.99 (6H, d, J = 6.1 Hz). |
| 11 | | ¹H-NMR (CDCl₃) δ: 8.33 (1H, s), 7.28 (1H, d, J = 8.5 Hz), 6.91 (1H, d, J = 8.5 Hz), 6.31 (1H, s), 4.95 (1H, s), 4.61 (2H, d, J = 13.2 Hz), 4.09 (3H, s), 3.22-3.12 (4H, m), 3.07-2.98 (3H, m), 2.87-2.84 (1H, m), 2.02-1.93 (4H, m), 1.53 (6H, s), 1.12 (6H, d, J = 6.3 Hz). |
| 12 | | ¹H-NMR (DMSO-D₆) δ: 9.01 (1H, t, J = 1.5 Hz), 8.41 (1H, d, J = 2.9 Hz), 8.22 (1H, s), 8.10 (1H, ddd, 10.7, 2.9, 1.5 Hz), 7.77 (1H, d, J = 8.5 Hz), 7.01 (1H, d, J = 8.5 Hz), 5.80 (1H, t, J = 5.6 Hz), 4.53-4.46 (2H, m), 3.28-3.11 (5H, m), 2.74 (2H, t, J = 6.6 Hz), 2.57 (2H, q, J = 7.2 Hz), 1.97-1.90 (2H, m), 1.87-1.75 (2H, m), 1.40 (6H, s), 1.02 (3H, t, J = 7.2 Hz). |

TABLE 1-continued

| Compound No. | Structural formula | Values of physical properties |
|---|---|---|
| 13 | 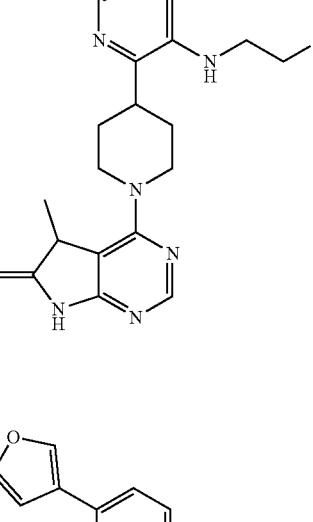 | ¹H-NMR (DMSO-D₆) δ: 10.97 (1H, s), 8.21 (1H, s), 8.17 (1H, d, J = 5.1 Hz), 7.87-7.84 (2H, m), 7.58 (1H, s), 6.99 (1H, d, J = 8.8 Hz), 5.95 (1H, t, J = 5.9 Hz), 4.56-4.49 (1H, m), 4.32-4.26 (1H, m), 3.75 (1H, q, J = 7.3 Hz), 3.33-3.15 (4H, m), 3.06-2.98 (1H, m), 2.65 (2H, t, J = 7.1 Hz), 2.53-2.46 (4H, m), 1.93-1.66 (8H, m), 1.30 (3H, d, J = 7.3 Hz). |
| 14 | 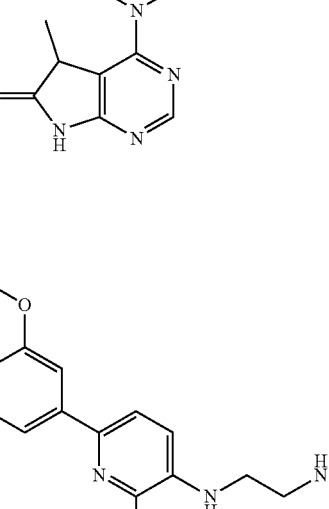 | ¹H-NMR (CDCl₃) δ: 8.34 (1H, s), 7.85 (1H, dd, J = 1.8, 0.9 Hz), 7.42 (1H, t, J = 1.8 Hz), 7.21 (1H, d, J = 8.3 Hz), 6.88 (1H, d, J = 8.3 Hz), 6.81 (1H dd, J = 1.8, 0.9 Hz), 4.70 (1H, s), 4.50 (1H, d, J = 13.4 Hz), 4.42 (1H, d, J = 13.4 Hz), 3.57 (1H, q, J = 7.6 Hz), 3.23 (2H, br s), 3.08 (1H, t, J = 11.5 Hz), 2.99-2.94 (1H, m), 2.83 (2H, dd, J = 7.0, 5.5 Hz), 2.57 (4H, m), 2.11-2.03 (5H, m), 1.80 (4H, m), 1.51 (3H, d, J = 7.6 Hz). |
| 15 | 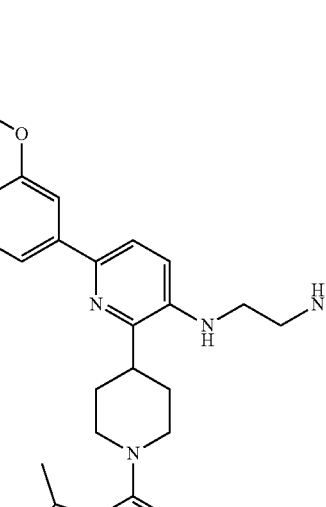 | ¹H-NMR (CDCl₃) δ: 8.74 (1H, d, J = 1.7 Hz), 8.33 (1H, s), 8.22 (1H, d, J = 2.7 Hz), 7.82 (1H, dd, J = 2.7, 1.7 Hz), 7.53 (1H, d, J = 8.3 Hz), 6.93 (1H, d, J = 8.3 Hz), 4.99 (1H, s), 4.52-4.45 (2H, m), 3.91 (3H, s), 3.58 (1H, q, J = 7.5 Hz), 3.27-3.25 (3H, m), 3.13 (1H, t, J = 12.7 Hz), 3.02 (2H, t, J = 5.4 Hz), 2.94-2.91 (1H, m), 2.18-2.04 (5H, m), 1.50 (3H, d, J = 7.5 Hz), 1.17 (6H, d, J = 6.2 Hz). |

TABLE 1-continued
| Compound No. | Structural formula | Values of physical properties |
|---|---|---|
| 16 | 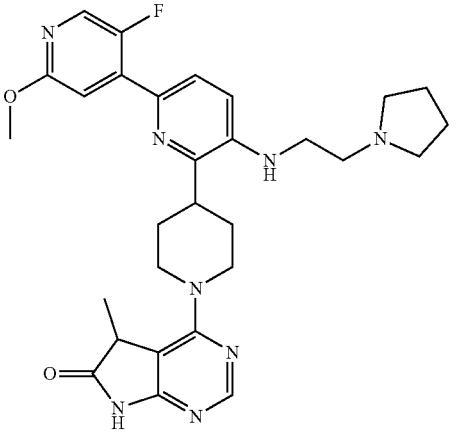 [SMILES: COc1cc(-c2ccc(NCCN3CCCC3)c(C3CCN(c4ncnc5c4C(C)C(=O)N5)CC3)n2)c(F)cn1] | ¹H-NMR (DMSO-D₆) δ: 10.96 (1H, s), 8.21 (1H, s), 8.13 (1H, d, J = 3.3 Hz), 7.65-7.62 (1H, m), 7.30 (1H, d, J = 5.9 Hz), 7.00 (1H, d, J = 8.8 Hz), 5.97-5.93 (1H, m), 4.54-4.49 (1H, m), 4.30-4.24 (1H, m), 3.81 (3H, s), 3.75 (1H, q, J = 7.4 Hz), 3.33-3.16 (6H, m), 3.05-2.98 (1H, m), 2.72-2.53 (4H, m), 1.90-1.65 (8H, m), 1.29 (3H, d, J = 7.4 Hz). |
| 17 | 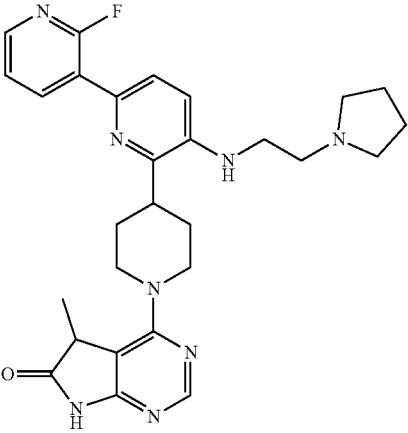 [SMILES: CC1C(=O)Nc2ncnc(N3CCC(c4nc(-c5cccnc5F)ccc4NCCN4CCCC4)CC3)c21] | ¹H-NMR (DMSO-D₆) δ: 10.96 (1H, s), 8.46-8.41 (1H, m), 8.20 (1H, s), 8.12-8.10 (1H, m), 7.58 (1H, dd, J = 8.4, 1.8 Hz), 7.42-7.38 (1H, m), 7.01 (1H, d, J = 8.4 Hz), 5.78-5.75 (1H, m), 4.54-4.49 (1H, m), 4.32-4.25 (1H, m), 3.73 (1H, q, J = 7.3 Hz), 3.34-3.16 (4H, m), 3.06-2.99 (1H, m), 2.73-2.51 (6H, m), 1.91-1.68 (8H, m), 1.29 (3H, d, J = 7.3 Hz). |
| 18 | 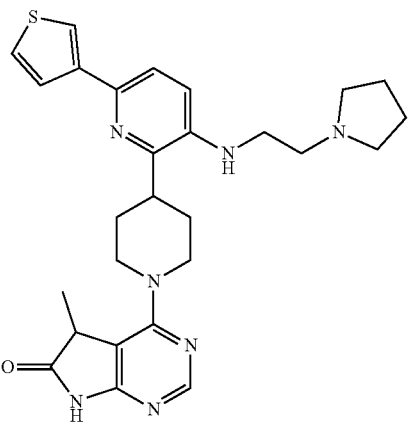 [SMILES: CC1C(=O)Nc2ncnc(N3CCC(c4nc(-c5ccsc5)ccc4NCCN4CCCC4)CC3)c21] | ¹H-NMR (CDCl₃) δ: 8.32 (1H, s), 7.66 (1H, dd, J = 3.0, 1.1 Hz), 7.59 (1H, dd, J = 3.0, 1.1 Hz), 7.38 (1H, d, J = 8.3 Hz), 7.33-7.30 (1H, m), 6.90 (1H, d, J = 8.3 Hz), 4.74 (1H, s), 4.51 (1H, d, J = 13.4 Hz), 4.41 (1H, d, J = 13.4 Hz), 3.58 (1H, q, J = 7.6 Hz), 3.27-3.20 (3H, m), 3.10 (1H, t, J = 12.6 Hz), 2.85 (2H, s), 2.58 (4H, br s), 2.17-1.98 (5H, m), 1.83-1.79 (4H, m), 1.51 (3H, d, J = 7.6 Hz). |

TABLE 1-continued

| Compound No. | Structural formula | Values of physical properties |
|---|---|---|
| 19 | | $^1$H-NMR (DMSO-D$_6$) δ: 10.96 (1H, s), 9.02-9.01 (1H, m), 8.42 (1H, d, J = 2.6 Hz), 8.21 (1H, s), 8.13-8.09 (1H, m), 7.78 (1H, d, J = 8.6 Hz), 7.00 (1H, d, J = 8.6 Hz), 5.76 (1H, t, J = 5.5 Hz), 4.54-4.49 (1H, m), 4.32-4.27 (1H, m), 3.74 (1H, q, J = 7.3 Hz), 3.30-3.11 (4H, m), 3.07-2 99 (1H, m), 2.66 (2H, t, J = 6.8 Hz), 2.55-2.50 (4H, m), 1.92-1.67 (8H, m), 1.30 (3H, d, J = 7.3 Hz). |
| 20 | | $^1$H-NMR (CDCl$_3$) δ: 8.32 (1H, s), 7.34 (1H, d, J = 8.3 Hz), 6.92 (1H, d, J = 8.3 Hz), 6.64 (1H, s), 4.99 (1H, s), 4.51-4.45 (2H, m.), 4.19 (3H, s), 3.57 (1H, q, J = 7.6 Hz), 3.22-3.18 (3H, m), 3.06-3.00 (2H, m), 2.86 (2H, t, J = 6.0 Hz), 2.60-5.57 (4H, m), 2.05-1.89 (4H, m), 1.83-1.80 (4H, m), 1.49 (3H, d, J = 7.6 Hz). |
| 21 | | $^1$H-NMR (CDCl$_3$) δ: 8.75 (1H, d, J = 2.0 Hz), 8.36 (1H, s), 8.22 (1H, d, J = 2.8 Hz), 7.82 (1H, dd, J = 2.8, 2.0 Hz), 7.54 (1H, d, J = 8.5 Hz), 6.93 (1H, d, J = 8.5 Hz), 4.82 (1H, s), 4.49-4.43 (2H, m), 3.91 (3H, s), 3.58 (1H, q, J = 7.4 Hz), 3.29-3.25 (1H, m), 3.22-3.19 (2H, m), 3.10 (1H, t, J = 11.3 Hz), 3.04-2.97 (1H, m), 2.66 (2H, t, J = 5.7 Hz), 2.32 (6H, s), 2.19-2.12 (1H, m), 2.04-2.02 (3H, m), 1.51 (3H, d, J = 7.4 Hz). |

TABLE 1-continued

| Compound No. | Structural formula | Values of physical properties |
| --- | --- | --- |
| 22 | 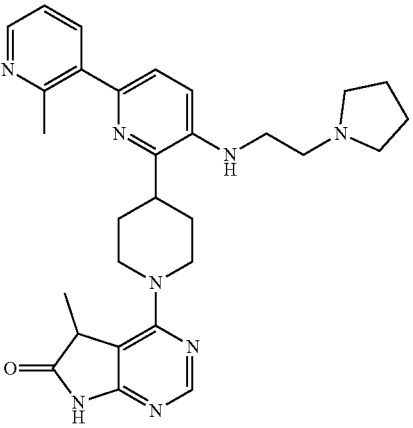 [SMILES: Cc1ncccc1-c1ccc(NCCN2CCCC2)c(C2CCN(c3ncnc4c3C(C)C(=O)N4)CC2)n1] | $^1$H-NMR (DMSO-D$_6$) δ: 10.95 (1H, s), 8.35 (1H, dd, J = 4.8, 1.7 Hz), 8.18 (1H, s), 7.70 (1H, dd, J = 7.7, 1.7 Hz), 7.27-7.21 (2H, m), 7.00 (1H, d, J = 8.4 Hz), 5.58-5.54 (1H, m), 4.50-4.43 (1H, m), 4.29-4.23 (1H, m), 3.71 (1H, q, J = 7.4 Hz), 3.28-3.12 (4H, m), 3.04-2.95 (1H, m), 2.70-2.65 (2H, m), 2.55-2.47 (4H, m), 2.51 (3H, s), 1.86-1.61 (8H m), 1.27 (3H, d, J = 7.4 Hz). |
| 23 | 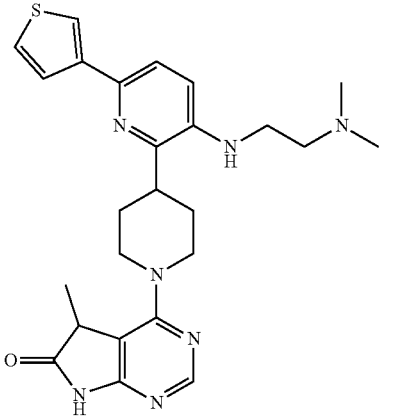 [SMILES: CC1C(=O)Nc2ncnc(N3CCC(c4nc(-c5ccsc5)ccc4NCCN(C)C)CC3)c21] | $^1$H-NMR (CDCl$_3$) δ: 8.33 (1H, s), 7.67 (1H, dd, J = 3.2, 1.2 Hz), 7.59 (1H, dd, J = 5.1, 1.2 Hz), 7.38 (1H, d, J = 8.5 Hz), 7.32 (1H, dd, J = 5.1, 3.2 Hz), 6.89 (1H, d, J = 8.5 Hz), 4.63 (1H, s), 4.49 (1H, d, J = 14.1 Hz), 4.40 (1H, d, J = 14.1 Hz), 3.59 (1H, q, J = 7.6 Hz), 3.30-3.25 (1H, m), 3.17-3.11 (3H, m), 3.02-2.96 (1H, m), 2.63 (2H, t, J = 5.7 Hz), 2.29 (6H, s), 2.17-2.11 (1H, m), 2.05-2.01 (3H, m), 1.51 (3H, d, J = 7.6 Hz). |
| 24 | 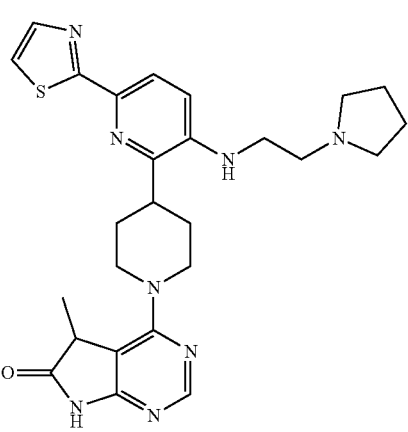 [SMILES: CC1C(=O)Nc2ncnc(N3CCC(c4nc(-c5nccs5)ccc4NCCN4CCCC4)CC3)c21] | $^1$H-NMR (DMSO-D$_6$) δ: 10.96 (1H, s), 8.21 (1H, s), 7.77-7.75 (2H, m), 7.54 (1H, d, J = 3.4 Hz), 7.00 (1H, d, J = 8.5 Hz), 5.88 (1H, t, J = 5.4 Hz), 4.52-4.46 (1H, m), 4.31-4.25 (1H, m), 3.75 (1H, q, J = 7.4 Hz), 3.30-3.00 (5H, m), 2.66 (2H, t, J = 6.8 Hz), 2.53-2.50 (4H, m), 1.90-1.82 (3H, m), 1.72-1.62 (5H, m), 1.31 (3H, d, J = 7.4 Hz). |

TABLE 1-continued

| Compound No. | Structural formula | Values of physical properties |
| --- | --- | --- |
| 25 | | $^1$H-NMR (CDCl$_3$) δ: 8.31 (1H, s), 7.87 (1H, d, J = 8.5 Hz), 7.69 (1H, s), 7.20 (1H, s), 6.91 (1H, d, J = 8.5 Hz), 5.12 (1H, s), 4.55 (1H, d, J = 13.4 Hz), 4.42 (1H, d, J = 13.4 Hz), 3.57 (1H, q, J = 7.6 Hz), 3.27-3.21 (3H, m), 3.07-2.99 (2H, m), 2.89-2.82 (2H, m), 2.59-2.56 (4H, m), 2.15-2.09 (2H, m), 2.02 (2H, d, J = 10.2 Hz), 1.82-1.81 (4H, m), 1.50 (3H, d, J = 7.6 Hz). |
| 26 | | $^1$H-NMR (DMSO-D$_6$) δ: 11.02 (1H, s), 9.04-9.04 (1H, m), 8.46-8.45 (1H, m), 8.24 (1H, s), 8.17-8.14 (1H, m), 7.84 (1H, d, J = 8.5 Hz), 7.09 (1H, d, J = 8.5 Hz), 6.17 (1H, s), 5.65 (1H, t, J = 5.1 Hz), 4.34-4.24 (2H, m), 4.21-4.15 (1H, m), 3.82-3.76 (1H, m), 3.58-3.51 (1H, m), 3.23-3.18 (2H, m), 2.68-2.62 (5H, m), 2.47-2.43 (3H, m), 1.67-1.64 (4H, m), 1.34 (3H, d, J = 7.6 Hz). |
| 27 | | $^1$H-NMR (CDCl$_3$) δ: 8.35 (1H, s), 8.09 (1H, d, J = 2.2 Hz), 7.21 (1H, d, J = 2.2 Hz), 6.47 (1H, s), 5.72 (1H, br s), 4.59-4.51 (1H, m), 4.46-4.38 (1H, m), 3.89 (3H, s), 3.66-3.49 (3H, m), 3.17-3.06 (1H, m), 2.97-2.87 (1H, m), 2.84 (2H, t, J = 5.7 Hz), 2.70-2.55 (5H, m), 2.06-2.00 (2H, m), 1.84-1.78 (4H, m), 1.78-1.69 (1H, m), 1.66-1.52 (1H, m), 1.48 (3H, d, J = 7.7 Hz) |

TABLE 1-continued
| Compound No. | Structural formula | Values of physical properties |
|---|---|---|
| 28 | 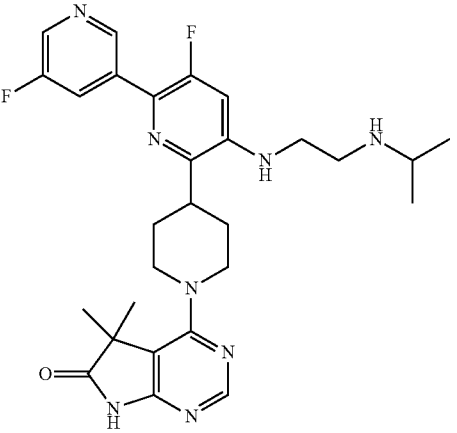 [SMILES: CC(C)NCCNc1cc(F)c(-c2cncc(F)c2)nc1C1CCN(c2ncnc3c2C(C)(C)C(=O)N3)CC1] | ¹H-NMR (DMSO-D₆) δ: 8.88 (1H, s), 8.47 (1H, d, J = 2.7 Hz), 8.21 (1H, s), 7.98-7.94 (1H, m), 6.94 (1H, d, J = 14.9 Hz), 6.22-6.16 (1H, m), 4.51-4.43 (2H, m), 3.25-3.13 (5H, m), 2.79-2.68 (3H, m), 1.97-1.89 (2H, m), 1.82-1.70 (2H, m), 1.39 (6H, s), 0.99 (6H, d, J = 6.1 Hz). |
| 29 | 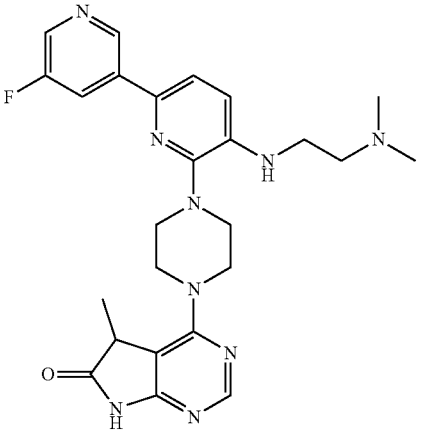 [SMILES: CC1C(=O)Nc2ncnc(N3CCN(c4nc(-c5cncc(F)c5)ccc4NCCN(C)C)CC3)c21] | ¹H-NMR (DMSO-D₆) δ: 11.03 (1H, s), 9.05-9.04 (1H, m), 8.43 (1H, d, J = 2.6 Hz), 8.24 (1H, s), 8.16-8.12 (1H, m), 7.71 (1H, d, J = 8.4 Hz), 6.99 (1H, d, J = 8.4 Hz), 5.32 (1H, t, J = 5.3 Hz), 3.91-3.84 (2H, m), 3.78 (1H, q, J = 7.5 Hz), 3.71-3.64 (2H, m), 3.24-3.11 (6H, m), 2.53 (2H, t, J = 6.2 Hz), 2.22 (6H, s), 1.31 (3H, d, J = 7.3 Hz). |
| 30 | 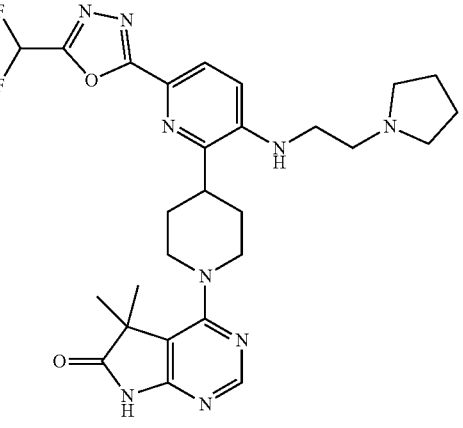 | ¹H-NMR (CDCl₃) δ: 8.34 (1H, s), 7.99 (1H, d, J = 8.5 Hz), 6.91 (1H, d, J = 8.5 Hz), 6.90 (1H, t, J = 47.3 Hz), 5.49 (1H, s), 4.60 (2H, d, J = 13.2 Hz), 3.30-3.18 (4H, m), 3.05-3.00 (1H, m), 2.89 (2H, t, J = 5.9 Hz), 2.65-2.59 (4H, m), 2.13-1.99 (4H, m), 1.85-1.81 (4H, m), 1.55 (6H, s). |

TABLE 1-continued
| Compound No. | Structural formula | Values of physical properties |
|---|---|---|
| 31 | 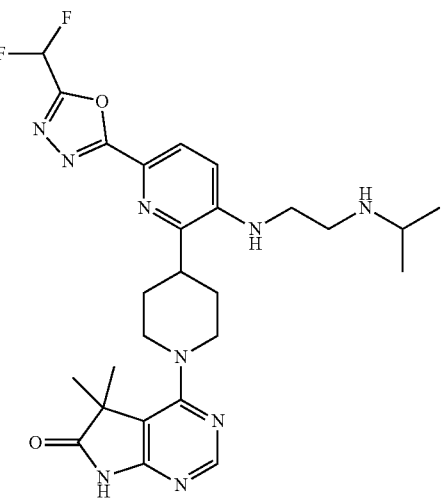 | ¹H-NMR (CDCl₃) δ: 8.31 (1H, s), 7.98 (1H, d, J = 8.5 Hz), 6.91 (1H, d, J = 8.5 Hz), 6.89 (1H, t, J = 52.1 Hz), 5.43 (1H, s), 4.60 (2H, d, J = 13.2 Hz), 3.26-3.19 (4H, m), 3.08-3.00 (3H, m), 2.91-2.85 (1H, m), 2.14-2.03 (4H, m), 1.56 (6H, s), 1.12 (6H, d, J = 6.3 Hz). |
| 32 | 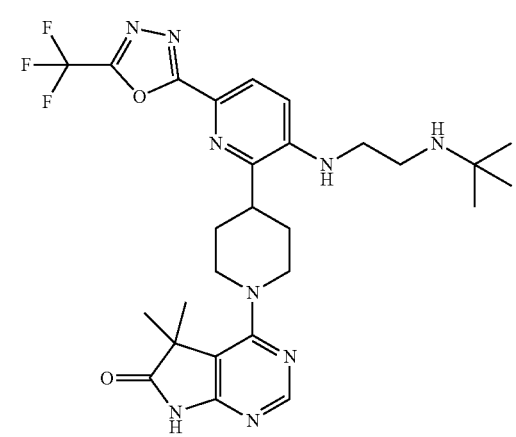 [SMILES: CC(C)(C)NCCNc1ccc(-c2nnc(C(F)(F)F)o2)nc1C1CCN(c2ncnc3c2C(C)(C)C(=O)N3)CC1] | ¹H-NMR (CDCl₃) δ: 8.33 (1H, s), 8.00 (1H, d, J = 8.5 Hz), 6.91 (1H, d, J = 8.5 Hz), 5.58 (1H, s), 4.62 (2H, d, J = 13.2 Hz), 3.23-3.19 (4H, m), 3.06-3.03 (1H, m), 2.98 (2H, t, J = 5.6 Hz), 2.10-2.03 (4H, m), 1.56 (6H, s), 1.17 (9H, s). |
| 33 | 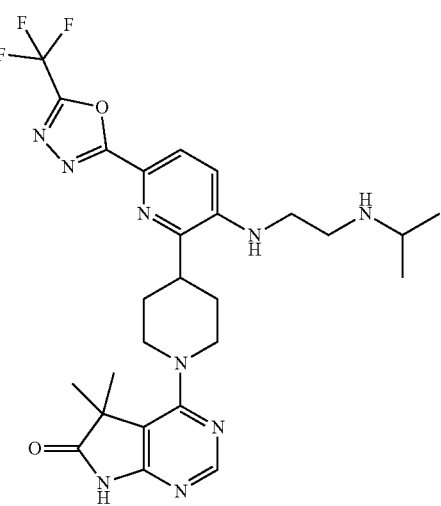 | ¹H-NMR (CDCl₃) δ: 8.34 (1H, s), 8.00 (1H, d, J = 8.5 Hz), 6.91 (1H, d, J = 8.5 Hz), 5.49 (1H, s), 4.60 (2H, d, J = 12.9 Hz), 3.26-3.19 (4H, m), 3.07-3.00 (3H, m), 2.91-2.83 (1H, m), 2.14-2.05 (4H, m), 1.56 (6H, s), 1.12 (6H, d, J = 6.1 Hz). |

TABLE 1-continued
| Compound No. | Structural formula | Values of physical properties |
|---|---|---|
| 34 | 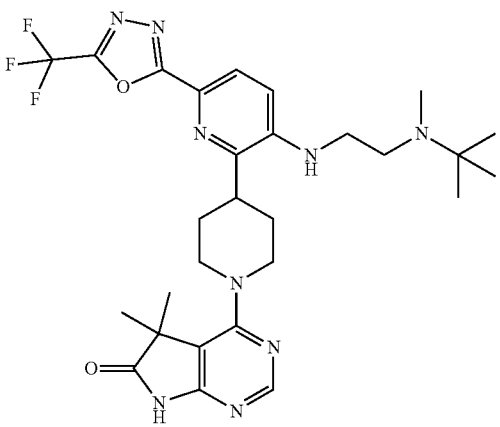 [SMILES: CN(CCNc1ccc(-c2nnc(C(F)(F)F)o2)nc1C1CCN(c2ncnc3c2C(C)(C)C(=O)N3)CC1)C(C)(C)C] | ¹H-NMR (DMSO-D₆) δ: 11.08 (1H, s), 8.20 (1H, s), 7.90 (1H, d, J = 8.8 Hz), 7.05 (1H, d, J = 8.8 Hz), 6.22 (1H, t, J = 4.9 Hz), 4.50-4.42 (2H, m), 3.27-3.09 (5H, m), 2.60-2.53 (2H, m), 2.19 (3H, s), 1.94-1.86 (2H, m), 1.82-1.69 (2H, m), 1.37 6H, s), 1.00 (9H, s). |
| 35 | 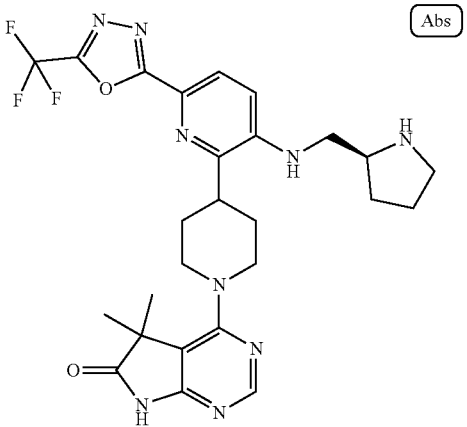 [SMILES: CC1(C)C(=O)Nc2ncnc(N3CCC(c4nc(-c5nnc(C(F)(F)F)o5)ccc4NC[C@@H]4CCCN4)CC3)c21] [Abs] | ¹H-NMR (DMSO-D₆) δ: 8.21 (1H, s), 7.88 (1H, d, J = 8.4 Hz), 7.11 (1H, d, J = 8.4 Hz), 6.44 (1H, t, J = 5.7 Hz), 4.50-4.45 (2H, m), 3.37-3.28 (1H, m), 3.22-3.07 (5H, m), 2.86-2.76 (2H, m), 1.93-1.59 (7H, m), 1.47-1.34 (1H, m), 1.39 (6H, s). |
| 36 | 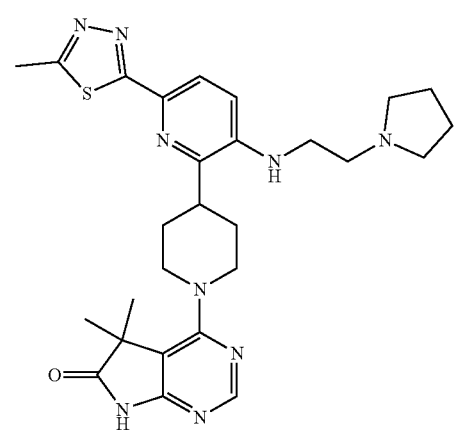 [SMILES: Cc1nnc(-c2ccc(NCCN3CCCC3)c(C3CCN(c4ncnc5c4C(C)(C)C(=O)N5)CC3)n2)s1] | ¹H-NMR (DMSO-D₆) δ: 11.10 (1H, s), 8.22 (1H, s), 7.84 (1H, d, J = 8.6 Hz), 7.03 (1H, d, J = 8.6 Hz), 6.05 (1H, t, J = 5.5 Hz), 4.50-4.43 (2H, m), 3.37-3.13 (5H, m), 2.67-2.63 (2H, m), 2.65 (3H, s), 2.53-2.47 (4H, m), 1.92-1.86 (2H, m), 1.75-1.66 (6H, m), 1.39 (6H, s). |

TABLE 1-continued
| Compound No. | Structural formula | Values of physical properties |
|---|---|---|
| 37 | 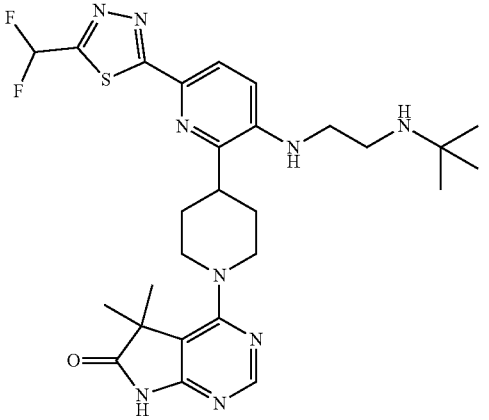 [SMILES: CC(C)(C)NCCNc1ccc(-c2nnc(C(F)F)s2)nc1C1CCN(c2ncnc3c2C(C)(C)C(=O)N3)CC1] | ¹H-NMR (DMSO-D₆) δ: 8.22 (1H, s), 7.95 (1H, d, J = 8.6 Hz), 7.50 (1H, t, J = 53.3 Hz), 7.08 1H, d, J = 8.6 Hz), 6.34 (1H, t, J = 5.5 Hz), 4.50-4.45 (2H, m), 3.37-3.14 (5H, m), 2.70 (2H, t, J = 6.8 Hz), 1.97-1.91 (2H, m), 1.77-1.66 (2H, m), 1.39 (6H, s), 1.03 (9H, s). |
| 38 | 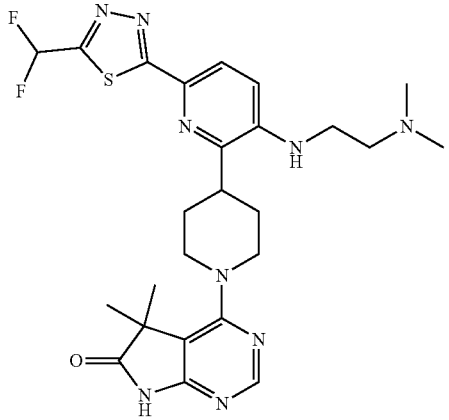 [SMILES: CN(C)CCNc1ccc(-c2nnc(C(F)F)s2)nc1C1CCN(c2ncnc3c2C(C)(C)C(=O)N3)CC1] | ¹H-NMR (DMSO-D₆) δ: 11.10 (1H, br s), 8.22 (1H, s), 7.95 (1H, d, J = 8.8 Hz), 7.49 (1H, t, J = 53.5 Hz) 7.07 (1H, d, J = 8.8 Hz), 6.25 (1H, t, J = 5.7 Hz), 4.49-4.43 (2H, m), 3.36-3.14 (5H, m), 2.50-2.46 (2H, m), 2.21 (6H, s), 1.95-1.89 (2H, m), 1.77-1.66 (2H, m), 1.40 (6H, s). |
| 39 | 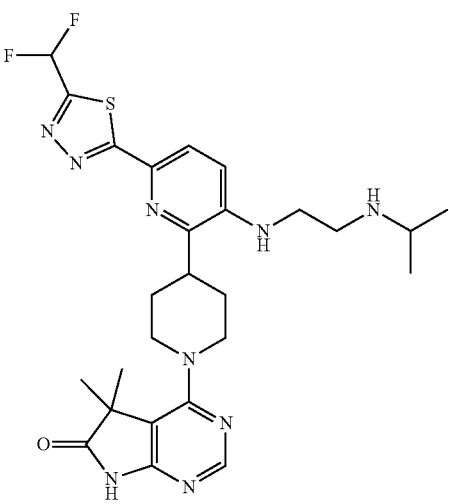 | ¹H-NMR (CDCl₃) δ: 8.37 (1H, s), 8.09 (1H, d, J = 8.5 Hz), 6.98 (1H, t, J = 53.3 Hz), 6.93 (1H, d, J = 8.5 Hz), 5.36 (1H, s), 4.60 (2H, d, J = 13.2 Hz), 3.25-3.20 (4H, m), 3.06-2.99 (3H, m), 2.92-2.83 (1H, m), 2.04-1.97 (4H, m), 1.57 (6H, s), 1.13 (6H, d, J = 6.1 Hz). |

TABLE 1-continued
| Compound No. | Structural formula | Values of physical properties |
|---|---|---|
| 40 | 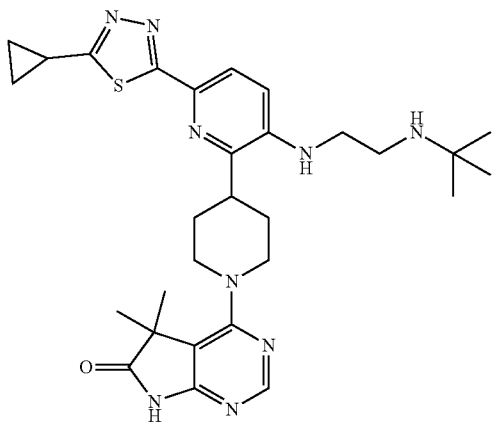 [SMILES: CC(C)(C)NCCNc1ccc(-c2nnc(C3CC3)s2)nc1C1CCN(c2ncnc3c2C(C)(C)C(=O)N3)CC1] | ¹H-NMR (DMSO-D₆) δ: 8.22 (1H, s), 7.82 (1H, d, J = 8.4 Hz), 7.03 (1H, d, J = 8.4 Hz), 6.07 (1H, t, J = 5.3 Hz), 4.50-4.45 (2H, m), 3.21-3.13 (5H, m), 2.69 (2H, t, J = 6.6 Hz), 2.47-2.41 (1H, m), 1.94-1.89 (2H, m), 1.75-1.65 (2H, m), 1.39 (6H, s), 1.18-1.14 (3H, m), 1.02 (9H, s), 1.01-0.97 (1H, m). |
| 41 | 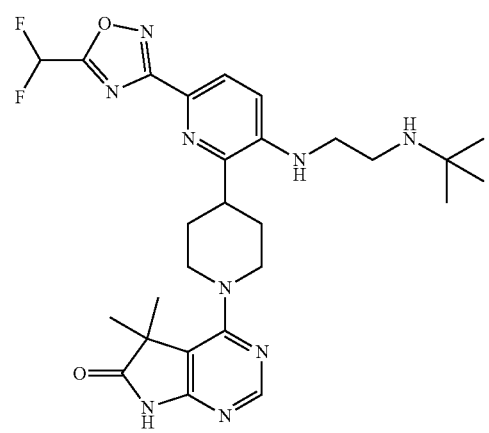 [SMILES: CC(C)(C)NCCNc1ccc(-c2noc(C(F)F)n2)nc1C1CCN(c2ncnc3c2C(C)(C)C(=O)N3)CC1] | ¹H-NMR (DMSO-D₆) δ: 8.19 (1H, s), 7.74 (1H, d, J = 8.8 Hz), 7.46 (1H, t, J = 51.7 Hz), 7.01 (1H, d, J = 8.8 Hz), 6.17 (1H, t, J = 5.3 Hz), 4.50-4.42 (2H, m), 3.26-3.08 (5H, m), 2.72-2.65 (2H, m), 1.91-1.83 (2H, m), 1.80-1.67 (2H, m), 1.36 (6H, s), 1.01 (9H, s). |
| 42 | 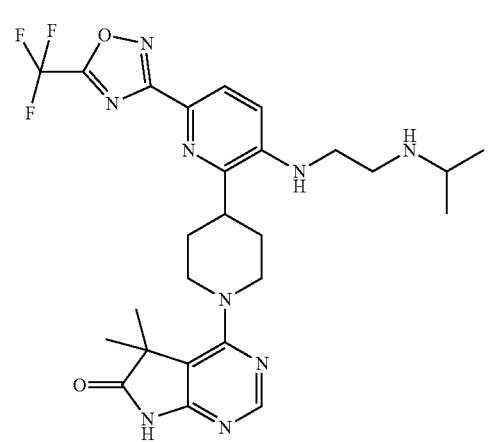 [SMILES: CC(C)NCCNc1ccc(-c2noc(C(F)(F)F)n2)nc1C1CCN(c2ncnc3c2C(C)(C)C(=O)N3)CC1] | ¹H-NMR (DMSO-D₆) δ: 8.22 (1H, s), 7.78 (1H, d, J = 8.8 Hz), 7.05 (1H, d, J = 8.8 Hz), 6.27 (1H, t, J = 5.5 Hz), 4.50-4.46 (2H, m), 3.28-3.14 (6H, m), 2.75-2.70 (2H, m), 1.91-1.87 (2H, m), 1.81-1.71 (2H, m), 1.39 (6H, s), 0.98 (6H, d, J = 6.2 Hz). |

TABLE 1-continued

| Compound No. | Structural formula | Values of physical properties |
|---|---|---|
| 43 | 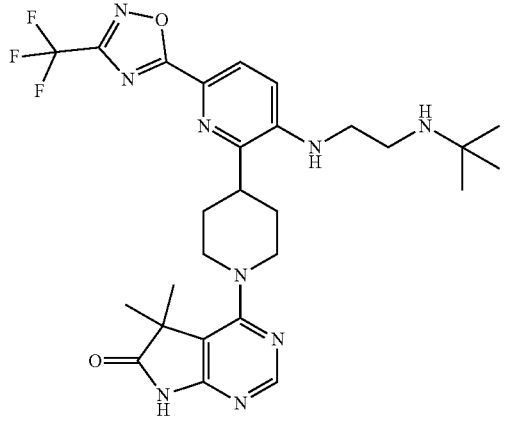 [SMILES: CC(C)(C)NCCNc1ccc(-c2nc(C(F)(F)F)no2)nc1C1CCN(c2ncnc3c2C(C)(C)C(=O)N3)CC1] | $^1$H-NMR (DMSO-D$_6$) δ: 8.21 (1H, s), 7.97 (1H, d, J = 8.4 Hz), 7.07 (1H, d, J = 8.4 Hz), 6.65 (1H, t, J = 5.5 Hz), 3.30-3.10 (2H, m), 3.26-3.13 (5H, m), 2.73-2.65 (2H, m), 1.94-1.87 (2H, m), 1.81-1.68 (2H, m), 1.37 (6H, s), 1.02 (9H, s). |
| 44 | 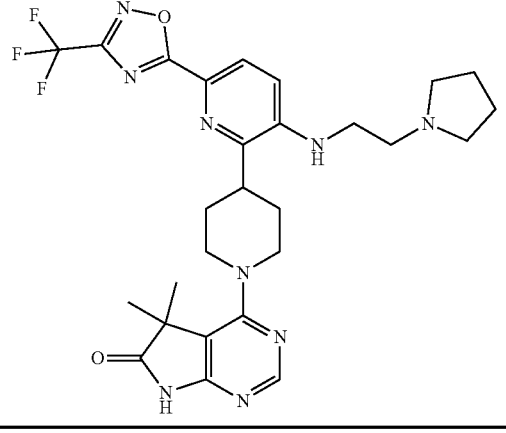 | $^1$H-NMR (DMSO-D$_6$) δ: 11.07 (1H, s), 8.21 (1H, s), 7.96 (1H, d, J = 8.4 Hz), 7.05 (1H, d, J = 8.4 Hz), 6.61 (1H, t, J = 5.5 Hz), 4.50-4.42 (2H, m), 3.39-3.22 (5H, m), 3.21-3.12 (2H, m), 2.68-2.61 (2H, m), 2.53-2.48 (2H, m), 1.93-1.85 (2H, m), 1.80-1.62 (6H, m), 1.37 (6H, s). |

Test Example 1: Confirmation of Inhibitory Effects on Akt1 Kinase Activity

Akt1 was prepared and assays of inhibitory activity of the compound according to the present invention against Akt1 kinase activity in vitro were conducted according to the method described in Biochem. J., vol. 385, pp. 399-408, 2005 and Cancer Res., vol. 68, pp. 2366-2374, 2008. In the preparation of Akt1 protein, human Akt1 tagged with the middle T antigen was expressed in an insect cell Sf9, Akt1 was prepared through affinity purification and activation by PDK1, and the resultant was stored at −80° C. until the inhibition assays of the compounds. In the inhibition assay of the compounds, Akt1 and the compound according to the present invention were subjected to pre-incubation at 25° C. for 120 minutes in a reaction buffer (15 mM Tris-HCl, pH 7.5, 0.01% Tween-20, 2 mM DTT). Subsequently, biotinylated Crosstide (biotin-KGSGSGRPRTSSFAEG, Millipore), MgCl$_2$, and ATP were added as substrates at the final concentration of 500 nM, 10 mM, and 150 μM, respectively, and the reaction was allowed to proceed at 25° C. for 60 minutes. EDTA was added to the final concentration of 40 mM to terminate the reaction, a detection liquid containing the Eu-anti-phospho-Crosstide antibody (PerkinElmer) and SureLight APC-SA (PerkinElmer) at the final concentration of 0.5 nM and 62.5 nM, respectively was added, and the reaction was allowed to proceed at room temperature for 2 hours. In the end, the fluorescence levels irradiated with an excitation light of 337 nm were assayed at two different wavelength levels (i.e., 620 nm and 665 nm) using PI-HERAstar FS (BMG LABTECH) or PHERAstar (BMG LABTECH). The level of the phosphorylation reaction was determined on the basis of the ratio of fluorescence levels at two wavelength levels, and the concentration of the compound at which phosphorylation could be inhibited by 50% was defined as the IC$_{50}$ level (nM) and shown in Table 2.

As reference compounds, conventional Comparative Example A (WO 2010/056563 (Example 31)) and Comparative Example B having inhibitory activity against Akt were used.

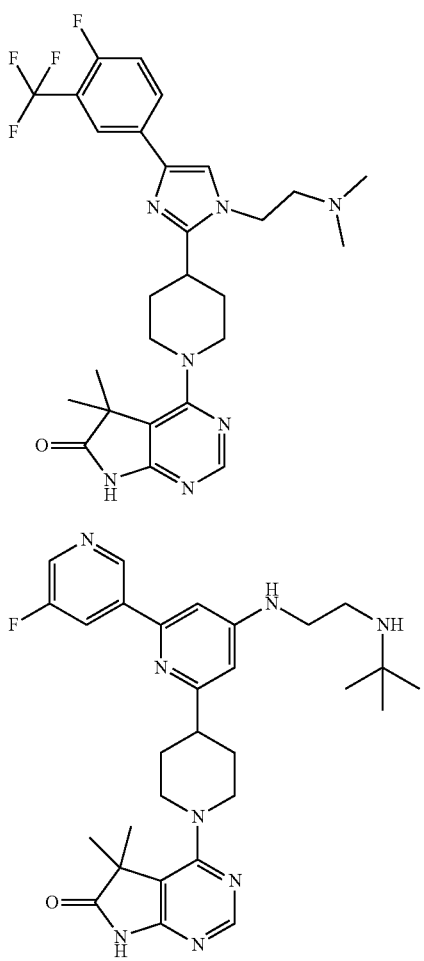

Test Example 2: Confirmation of Inhibitory Effects on Rsk1 Kinase Activity

Inhibitory activity of the compound according to the present invention on Rsk1 kinase activity in vitro was assayed using the QSS Assist™ FP assay kit (Carna Biosciences, Inc.).

In the inhibition assay of inhibitory activity of the compound, the test compound was diluted by serial dilution with dimethyl sulfoxide (DMSO). Subsequently, an Rsk1 protein, a substrate peptide (final concentration: 100 nM), magnesium chloride (final concentration: 10 mM), ATP (final concentration: 30 μM), and the solution of the test compound in DMSO (DMSO final concentration: 5%) were added to the kinase reaction buffer (20 mM HEPES (pH 7.4), 2 mM dithiothreitol, 0.01% Tween-20), and the mixture was incubated at 25° C. for 40 minutes to perform the kinase reaction. The IMAP Progressive Binding Reagent diluted to 400-fold with the IMAP Progressive Binding Buffer A (Molecular Devices, LLC) was added to terminate the kinase reaction. The reaction product was allowed to stand at room temperature in the dark for 120 minutes and assayed with the use of PHERAstar (BMG LABTECH; excitation wavelength: 485 nm; detection wavelength: 520 nm). The phosphorylation reaction level was determined based on the degree of fluorescence polarization, and the concentration of the compound at which phosphorylation could be inhibited by 50% was defined as the $IC_{50}$ level (nM) and shown in Table 3.

TABLE 2

| Compound No. | AKT inhibitory activity $IC_{50}$ (nM) |
|---|---|
| 1 | 6.8 |
| 5 | 3.5 |
| 11 | 5.8 |
| 13 | 1.4 |
| 14 | 0.5 |
| 15 | 2.1 |
| 16 | 1.9 |
| 17 | 0.6 |
| 18 | 0.5 |
| 19 | 0.4 |
| 20 | 0.6 |
| 21 | 4.0 |
| 22 | 1.8 |
| 23 | 0.7 |
| 24 | 1.9 |
| 25 | 2.7 |
| 27 | 1.6 |
| 30 | 14.5 |
| 31 | 7.6 |
| 32 | 1.4 |
| 33 | 2.5 |
| 34 | 1.0 |
| 37 | 3.3 |
| 39 | 4.1 |
| 40 | 3.6 |
| 41 | 7.2 |
| 42 | 4.8 |
| 43 | 1.0 |
| 44 | 2.6 |
| A | 52.2 |
| B | 657.0 |

TABLE 3

| Compound No. | Rsk inhibitory activity $IC_{50}$ (nM) |
|---|---|
| 1 | 1.5 |
| 2 | 1.5 |
| 5 | 0.7 |
| 6 | 1.0 |
| 7 | 1.7 |
| 8 | 1.7 |
| 9 | 1.1 |
| 10 | 0.9 |
| 11 | 0.7 |
| 12 | 1.8 |
| 13 | 1.4 |
| 14 | 1.7 |
| 15 | 1.1 |
| 16 | 0.8 |
| 17 | 1.1 |
| 18 | 1.4 |
| 19 | 0.9 |
| 20 | 0.9 |
| 21 | 1.3 |
| 23 | 1.5 |
| 27 | 1.8 |
| 30 | 1.7 |
| 31 | 1.8 |
| 32 | 0.6 |
| 33 | 1.0 |
| 34 | 0.9 |
| 35 | 1.5 |
| 37 | 0.5 |
| 38 | 0.9 |
| 39 | 0.6 |

TABLE 3-continued

| Compound No. | Rsk inhibitory activity IC$_{50}$ (nM) |
|---|---|
| 40 | 0.6 |
| 41 | 1.6 |
| 42 | 1.2 |
| 43 | 0.4 |
| 44 | 0.5 |

Test Example 3: Confirmation of Inhibitory Effects on S6K1 Kinase Activity

Inhibitory activity of the compound according to the present invention on S6K1 kinase activity in vitro was assayed using the QSS Assist™ FP assay kit (Carna Biosciences, Inc.).

In the inhibition assay for inhibitory activity of the compound, the test compound was diluted by serial dilution with dimethyl sulfoxide (DMSO). Subsequently, an S6K protein, a substrate peptide (final concentration: 100 nM), magnesium chloride (final concentration: 5 mM), ATP (final concentration: 25 μM), and the solution of the test compound in DMSO (final DMSO concentration: 5%) were added to the kinase reaction buffer (20 mM HEPES (pH 7.4), 2 mM dithiothreitol, 0.01% Tween-20), and the mixture was incubated at 25° C. for 30 minutes to perform the kinase reaction. The IMAP Progressive Binding Reagent diluted to 400-fold with the IMAP Progressive Binding Buffer A (Molecular Devices, LLC) was added thereto to terminate the kinase reaction. The reaction product was allowed to stand at room temperature in the dark for 120 minutes and assayed with the use of PHERAstar (BMG LABTECH; excitation wavelength: 485 nm; detection wavelength: 520 nm). The level of phosphorylation reaction was determined based on the degree of fluorescence polarization, and the concentration of the compound at which phosphorylation could be inhibited by 50% was defined as the IC$_{50}$ level (nM) and shown in Table 4.

TABLE 4

| Compound No. | S6K inhibitory activity IC$_{50}$ (nM) |
|---|---|
| 1 | 0.4 |
| 2 | 0.3 |
| 3 | 0.4 |
| 4 | 0.4 |
| 5 | 0.3 |
| 6 | 0.4 |
| 7 | 0.3 |
| 8 | 0.3 |
| 9 | 0.3 |
| 10 | 0.3 |
| 11 | 0.3 |
| 12 | 0.3 |
| 13 | 0.4 |
| 14 | 0.9 |
| 15 | 0.7 |
| 16 | 0.7 |
| 17 | 0.7 |
| 18 | 0.8 |
| 19 | 0.5 |
| 20 | 0.6 |
| 21 | 0.7 |
| 23 | 0.4 |
| 24 | 0.6 |
| 26 | 0.6 |
| 28 | 0.3 |
| 29 | 0.8 |
| 30 | 0.5 |
| 31 | 0.6 |
| 32 | 0.4 |
| 33 | 0.5 |
| 34 | 0.4 |
| 35 | 0.4 |
| 36 | 0.4 |
| 37 | 0.3 |
| 38 | 0.3 |
| 39 | 0.3 |
| 40 | 0.3 |
| 41 | 0.3 |
| 42 | 0.5 |
| 43 | 0.4 |
| 44 | 0.4 |

Test Example 4: Cell Growth Inhibition Study

The in vitro cell growth inhibition study using RKO cells (human colon cancer cell lines) was conducted as described below.

RKO cells (ATCC, Cat#: CRL-2577) cultured in a MEM medium (GIBCO, Cat#:10370-088) supplemented with 10% FBS, 1 mM L-glutamine (GIBCO, Cat#:25030), and 1 mM sodium pyruvate (GIBCO, Cat#:11360) were seeded in a 96-well flat bottom microplate (COSTAR, Cat#:3904) at $2 \times 10^3$ cells (150 μl) and cultured in an incubator containing 5% $CO_2$ at 37° C. for 1 day. The compound according to the present invention subjected to serial dilution with dimethyl sulfoxide or dimethyl sulfoxide alone was added to a MEM medium containing 10% FBS, 1 mM L-glutamine, and 1 mM sodium pyruvate. The resultant medium containing the compound or dimethyl sulfoxide alone was added to the RKO cells in the culture plate by 50 μl/well at the final concentration of the compound to 10, 3, 1, 0.3, 0.1, 0.03, 0.01, 0.003, and 0 μM, respectively. Another RKO cell culture plate separately prepared was allowed to stand at room temperature for 30 minutes, then 100 μl of the medium was removed, and added 50 μl of CellTiter-Glo® 2.0 Assay (Promega, Cat#:G9242) to each well. After the plates were placed in the dark for 10 minutes, the luminescence level derived from viable cells in each well was measured by the Multimode Plate Reader (PerkinElmer, EnSpire). The cells treated with the compound or dimethyl sulfoxide alone were cultured at 37° C. in an incubator containing 5% $CO_2$ for an additional 3 days. After incubation, the culture plate was placed at room temperature for 30 minutes, and 150 μl of the supernatant was removed from each well to adjust the amount of the remaining cell culture solution to 50 μl each. To 50 μl of the remaining cell culture solution, the equivalent amount of CellTiter-Glo® 2.0 Assay was added. After the cell culture plate was placed in the dark for 10 minutes, the luminescence level derived from viable cells in each well was assayed with the use of the Multimode Plate Reader. The cell growth rate was calculated by the formulae shown below and the concentration at which the cell growth rate became 50%; i.e., the concentration of the compound according to the present invention at which cell growth would be inhibited by 50% was determined ($GI_{50}$ (nM)).

Cell growth rate (%)=$(T-C_0)/(C-C_0) \times 100$, provided that $T$ is equal to or greater than $C_0(T \geq C_0)$ Cell growth rate (%)=$(T-C_0)/C_0 \times 100$, provided that $T$ is less than $C_0(T<C_0)$ $C_0$: Luminescence level in each well when the compound is added (count per second)

C: Luminescence level in each well when dimethyl sulfoxide is added alone (count per second)

T: Luminescence level in each well when the test compound is added (count per second)

As control compounds, conventional Comparative Example A (WO 2010/056563 (Example 31)) and Comparative Example B having inhibitory activity against Akt were used.

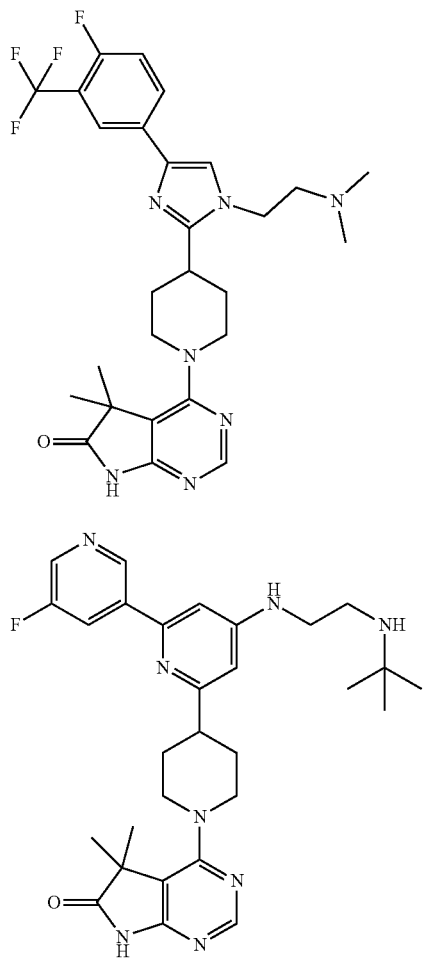

A

B

The GI$_{50}$ levels of representative compounds according to the present invention and reference compounds in RKO cells were evaluated, and the results are shown in Table 5.

TABLE 5

| Compound No | Cell growth inhibition GI$_{50}$ (nM) |
|---|---|
| 1 | 136 |
| 13 | 111 |
| 14 | 118 |
| 15 | 122 |
| 24 | 130 |
| 26 | 124 |
| 27 | 48 |
| 30 | 82 |
| 32 | 89 |
| 41 | 86 |
| 44 | 102 |

TABLE 5-continued

| Compound No | Cell growth inhibition GI$_{50}$ (nM) |
|---|---|
| A | 1048 |
| B | 2641 |

The results demonstrate that the compound according to the present invention has cell growth inhibitory activity that is significantly higher than that of a conventional piperazine derivative having Akt inhibitory activity. As a result of comparison of Compound 1 and Comparative Example B, sites of substitution in an amino acid side chain including $R_3$, $R_4$, $R_5$, and $R_6$ were found to significantly influence the cell growth inhibitory activity. A difference in activity caused by such sites of substitution is not known and thus is a surprising discovery.

Test Example 5: Cell Growth Inhibition Study

The in vitro cell growth suppression test on HEC-6 cells (endometrial cancer cell lines) was performed under the conditions described below.

HEC-6 cells (Health Science Research Resources Bank, Cell Number: JCRB1118) cultured in a MEM medium containing 15% FBS (GIBCO, Cat#: 10370) were seeded on a 384-well flat bottom microplate (CORNING, Cat#: 3571) at 500 cells/well (20 μl) and cultured in an incubator containing 5% carbon dioxide at 37° C. for 1 day. The compound according to the present invention subjected to serial dilution with dimethyl sulfoxide or dimethyl sulfoxide alone was added to a MEM medium containing 15% FBS. The resultant medium containing the compounds or dimethyl sulfoxide alone was added to the HEC-6 cells by 5 μl/well at the final concentration of the compound to 10, 3, 1, 0.3, 0.1, 0.03, 0.01, 0.003, 0.001, 0.0003, and 0 μM, respectively. Another HEC-6 cell culture plate separately prepared was placed at room temperature for 30 minutes, and 20 μl of CellTiter-Glo® 2.0 Assay (Promega, Cat#: G9243) was added to each well. The plate was shaken with a plate shaker for 10 minutes and placed in the dark for 30 minutes. Thereafter, the luminescence level derived from viable cells in each well was assayed with the use of the Multimode Plate Reader (PerkinElmer, EnVision). The cells to which the compound or dimethyl sulfoxide had been added alone were cultured at 37° C. in an incubator containing 5% carbon dioxide for an additional 3 days. After the culture, the culture product was placed at room temperature for 30 minutes, and CellTiter-Glo® 2.0 Assay was added at 25 μl/well. The plate was shaken with a plate shaker for 10 minutes and placed in the dark for 30 minutes. Thereafter, the luminescence level derived from viable cells in each well was assayed with the use of the Multimode Plate Reader. The cell growth rate was calculated by the formulae shown below and the concentration at which the cell growth rate became 50%; i.e., the concentration of the compound according to the present invention at which cell growth would be inhibited by 50% (GI$_{50}$ (nM)) was determined.

Cell growth rate (%)=$(T-C_0)/(C-C_0)\times 100$, provided that $T$ is equal to or greater than $C_0 (T \geq C_0)$ Cell growth rate (%)=$(T-C_0)/C_0 \times 100$, provided that $T$ is less than $C_0 (T<C_0)$ $C_0$: Luminescence level in each well when the compound is added (count per second)

C: Luminescence level in each well when dimethyl sulfoxide is added alone (count per second)

T: Luminescence level in each well when the test compound is added (count per second)

As reference compounds, conventional Comparative Example A (WO 2010/056563 (Example 31)) and Comparative Example B having inhibitory activity against Akt were used.

The GI$_{50}$ levels of representative compounds according to the present invention on HEC-6 cells were evaluated, and the results are shown in Table 6.

TABLE 6

| Compound No. | Cell growth inhibition GI$_{50}$ (μM) |
|---|---|
| 13 | 89 |
| 14 | 103 |
| 17 | 40 |
| 18 | 84 |
| 19 | 19 |
| 20 | 53 |
| 22 | 43 |
| 23 | 105 |
| 24 | 108 |
| 26 | 109 |
| 27 | 58 |
| 29 | 142 |
| 30 | 146 |
| 32 | 84 |
| 34 | 72 |
| 41 | 138 |
| 43 | 42 |
| 44 | 57 |
| A | 1042 |
| B | 2916 |

All publications, patents, and patent applications cited herein are incorporated herein by reference in their entirety.

The invention claimed is:

1. A compound represented by Formula (I) or a salt thereof:

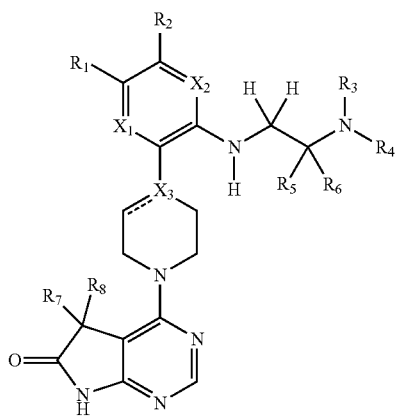

(I)

wherein
R$_1$ represents an optionally substituted 4- to 6-membered monocyclic unsaturated heterocyclic group having 1 to 3 hetero atoms selected from among N, S, and O;
R$_2$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group;
R$_3$, R$_4$, and R$_5$, which may be the same or different, each represent a hydrogen atom, a C1-C6 alkyl group, a C1-C6 haloalkyl group, or a C3-C6 cycloalkyl group; or R$_3$ and R$_4$, together with a nitrogen atom to which they are bound, form a 4- to 6-membered monocyclic saturated heterocycle having 1 to 3 hetero atoms selected from among N, S, and O, and R$_5$ represents a hydrogen atom, a C1-C6 alkyl group, a C1-C6 haloalkyl group, or a C3-C6 cycloalkyl group; or R$_4$ and R$_5$, together with a nitrogen atom to which they are bound and a carbon atom adjacent thereto, form a 4- to 6-membered monocyclic saturated heterocycle having 1 to 3 hetero atoms selected from among N, S, and O, and R$_3$ represents a hydrogen atom, a C1-C6 alkyl group, a C1-C6 haloalkyl group, or a C3-C6 cycloalkyl group;
R$_6$ represents a hydrogen atom, a C1-C6 alkyl group, a C1-C6 haloalkyl group, or a C3-C6 cycloalkyl group;
R$_7$ and R$_8$, which may be the same or different, each represent a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group; or R$_7$ and R$_8$, together with a carbon atom to which they are bound, form a C3-C10 cycloalkyl group;
X$_1$ and X$_2$, which may be the same or different, each represent N or CR$_9$, and R$_9$ represents a hydrogen atom, a halogen atom, a hydroxyl group, an amino group, a cyano group, a nitro group, a C1-C6 alkyl group, a C1-C6 haloalkyl group, a C2-C6 alkenyl group, a C2-C6 alkynyl group, or a C3-C6 cycloalkyl group; and
X$_3$ represents N or CH when a broken line (-----) indicates a single bond, or C when a broken line indicates a double bond, provided that at least either one of X$_1$ or X$_2$ represents N.

2. The compound or the salt thereof according to claim 1, wherein R$_1$ represents a 4- to 6-membered monocyclic unsaturated heterocyclic group having 1 to 3 hetero atoms selected from among N, S, and O, which may comprise 1 to 3 substituents selected from among a halogen atom, a C1-C6 alkyl group, a C1-C6 haloalkyl group, a C1-C6 alkoxy group, and a C3-C10 cycloalkyl group.

3. The compound or the salt thereof according to claim 1, wherein R$_2$ represents a hydrogen atom or a halogen atom, R$_6$ represents a hydrogen atom, R$_7$ represents a C1-C6 alkyl group, R$_8$ represents a hydrogen atom or a C1-C6 alkyl group, X$_1$ represents N or CR$_9$, R$_9$ represents a hydrogen atom or a halogen atom, and X$_2$ represents N or CH.

4. The compound or the salt thereof according to claim 1, wherein R$_1$ represents a furanyl group, a thienyl group, a thiazolyl group, a thiadiazolyl group, an oxazolyl group, an oxadiazolyl group, a pyridinyl group, or a pyrazolyl group, which may comprise 1 to 3 substituents selected from among a halogen atom, a C1-C6 alkyl group, a C1-C6 haloalkyl group, a C1-C6 alkoxy group, and a C3-C10 cycloalkyl group.

5. The compound or the salt thereof according to claim 1, wherein R$_3$, R$_4$, and R$_5$, which may be the same or different, each represent a hydrogen atom or a C1-C6 alkyl group; or R$_3$ and R$_4$, together with a nitrogen atom to which they are bound, form a 4- to 6-membered monocyclic saturated heterocycle having a nitrogen atom, and R$_5$ represents a hydrogen atom or a C1-C6 alkyl group; or R$_4$ and R$_5$, together with a nitrogen atom to which they are bound and a carbon atom adjacent thereto, form a 4- to 6-membered monocyclic saturated heterocycle having a nitrogen atom, and R$_3$ represents a hydrogen atom or a C1-C6 alkyl group.

6. The compound or the salt thereof according to claim 1, wherein R$_1$ represents a pyridinyl group having a halogen atom or a C1-C6 alkoxy group, a pyrazolyl group having a C1-C6 alkyl group and a C1-C6 haloalkyl group, an oxadiazolyl group having a C1-C6 haloalkyl group, or an unsubstituted furanyl group or thiazolyl group, $R_2$, $R_5$ and $R_6$ each represent a hydrogen atom, $R_3$ represents a hydrogen atom, and $R_4$ represents a C1-C6 alkyl group; or $R_3$ and $R_4$, together with a nitrogen atom to which they are bound, form a 4- to 6-membered monocyclic saturated heterocycle having a nitrogen atom, $R_7$ represents a C1-C6 alkyl group, $R_8$ represents a hydrogen atom or a C1-C6 alkyl group, and $X_1$ and $X_2$, which may be different from each other, each represent N or CH; and a broken line (-----) indicates a single bond and $X_3$ represents CH.

7. The compound or the salt thereof according to claim 6, wherein $R_1$ represents a pyrazolyl group having a C1-C6 alkyl group and a C1-C6 haloalkyl group, or an oxadiazolyl group having a C1-C6 haloalkyl group.

8. The compound or the salt thereof according to claim 1, wherein the compound is selected from the compounds indicated below:

4-(4-(6-(5-(difluoromethyl)-1,3,4-oxadiazol-2-yl)-3-((2-(pyrrolidin-1-yl)ethyl)amino)pyridin-2-yl)piperidin-1-yl)-5,5-dimethyl-5H-pyrrolo[2,3-d]pyrimidin-6(7H)-one;

4-(4-(3-((2-(tert-butylamino)ethyl)amino)-6-(5-(trifluoromethyl)-1,3,4-oxadiazol-2-yl)pyridin-2-yl)piperidin-1-yl)-5,5-dimethyl-5H-pyrrolo[2,3-d]pyrimidin-6(7H)-one; and 4-(4-(3-((2-(tert-butyl amino)ethyl)amino)-6-(5-(difluoromethyl)-1,2,4-oxadiazol-3-yl)pyridin-2-yl)piperidin-1-yl)-5,5-dimethyl-5H-pyrrolo[2,3-d]pyrimidin-6(7H)-one.

9. A pharmaceutical composition for the treatment of a tumor comprising, as an active ingredient, the compound or the salt thereof according to claim 1.

10. A method for the treatment of a tumor comprising administering an effective amount of the compound or the salt thereof according to claim 1 to a patient in need thereof.

* * * * *